United States Patent
O'Shea et al.

(10) Patent No.: US 9,913,866 B2
(45) Date of Patent: Mar. 13, 2018

(54) SELECTIVE CELL TARGETING USING ADENOVIRUS AND CHEMICAL DIMERS

(71) Applicant: Salk Institute for Biological Studies, La Jolla, CA (US)

(72) Inventors: Clodagh O'Shea, San Diego, CA (US); Shigeki Miyake-Stoner, La Jolla, CA (US); Colin Powers, San Diego, CA (US)

(73) Assignee: Salk Institute for Biological Studies, La Jolla, CA (US)

( * ) Notice: Subject to any disclaimer, the term of this patent is extended or adjusted under 35 U.S.C. 154(b) by 516 days.

(21) Appl. No.: 14/485,472

(22) Filed: Sep. 12, 2014

(65) Prior Publication Data

US 2015/0017127 A1 Jan. 15, 2015

Related U.S. Application Data

(63) Continuation of application No. PCT/US2013/031002, filed on Mar. 13, 2013.

(60) Provisional application No. 61/610,416, filed on Mar. 13, 2012.

(51) Int. Cl.
| | |
|---|---|
| *A61K 35/76* | (2015.01) |
| *C12N 7/00* | (2006.01) |
| *C12N 15/861* | (2006.01) |
| *A61K 35/761* | (2015.01) |
| *C12N 15/86* | (2006.01) |

(52) U.S. Cl.
CPC .............. *A61K 35/761* (2013.01); *C12N 7/00* (2013.01); *C12N 15/86* (2013.01); *C07K 2319/20* (2013.01); *C12N 2710/10034* (2013.01); *C12N 2710/10052* (2013.01); *C12N 2710/10345* (2013.01)

(58) Field of Classification Search
CPC ................. C12N 15/86; C12N 2710/10345; C12N 7/00; C12N 2710/10034; C12N 2710/10052; C07K 2319/20; A61K 35/761

See application file for complete search history.

(56) References Cited

U.S. PATENT DOCUMENTS 6,506,379 B1 * 1/2003 Clackson ............. C07K 14/715
424/93.21
6,984,635 B1 1/2006 Schreiber et al.

FOREIGN PATENT DOCUMENTS

| EP | 1413586 | * | 4/2004 |
| WO | WO 2012-024350 | | 2/2012 |

OTHER PUBLICATIONS

Belousova et al Journal of Virology, 2002, 8621-8631.*
Belousova et al Journal of Virology, 2002, 8621,-8631.*
O'Shea, C., et al., (Embo J, 24(6): 1211-21 (2005).*
Fang et al (Molecular Therapy vol. 15 No. 6, 1153-1159).*
Galsgow et al (PLoS One, 2009, 4, 12, e8355, 1-12.*
Behar, G., et al., FEBS Journal, 2009, 276(14): p. 3881-3893.*
Waehler et al (Nature Review, 2007, 8, 573-587.*
Chen et al Proc. Natl. Acad. Sci. USA , 1995, 4947-4951.*
NCBI accession No. CV110986/ BF118061, dated Jan. 2011, pp. 1-3.*
Bayle et al Chem Biol. 2006; 13(1):99-10.*
Chong et al., "A System for Small-Molecule Control of Conditionally Replication-Competent Adenoviral Vectors," *Mol Ther* 5(2):195-203, 2002.
Waehler et al., "Engineering targeted viral vectors for gene therapy," *Nat Rev Genet* 8(8):573-587, 2007.
Belousova et al., "Modulation of Adenovirus Vector Tropism via Incorporation of Polypeptide Ligands into the Fiber Protein," *J Virol* 76(17):8621-8631, 2002.
Bayle et al., "Rapamycin Analogs with Differential Binding Specificity Permit Orthogonal Control of Protein Activity," *Chem Biol* 13:99-107, 2006.
Chen et al., "Identification of an 11-kDa FKBP12-rapamycin-binding domain within the 289-kDa FKBP12-rapamycin-associated protein and characterization of a critical serine residue," *Proc Natl Acad Sci USA* 92:4947-4951, 1995.
Glasgow et al., "A Strategy for Adenovirus Vector Targeting with a Secreted Single Chain Antibody," *PLoS One,* vol. 4:e8355, 2009.
Verheije et al., "Retargeting of Viruses to Generate Oncolytic Agents," *Adv. Virol.,* vol. 2012:1-15, 2012.

* cited by examiner

*Primary Examiner* — Anoop K Singh
(74) *Attorney, Agent, or Firm* — Klarquist Sparkman, LLP

(57) ABSTRACT

Compositions and methods for retargeting adenovirus to a cell using chemical dimers are described. In particular, a recombinant adenovirus comprising a nucleic acid comprising a capsid-dimerizing agent binder conjugate and a ligand-dimerizing agent binder conjugate is provided.

10 Claims, 37 Drawing Sheets

Rapamycin

AP21967

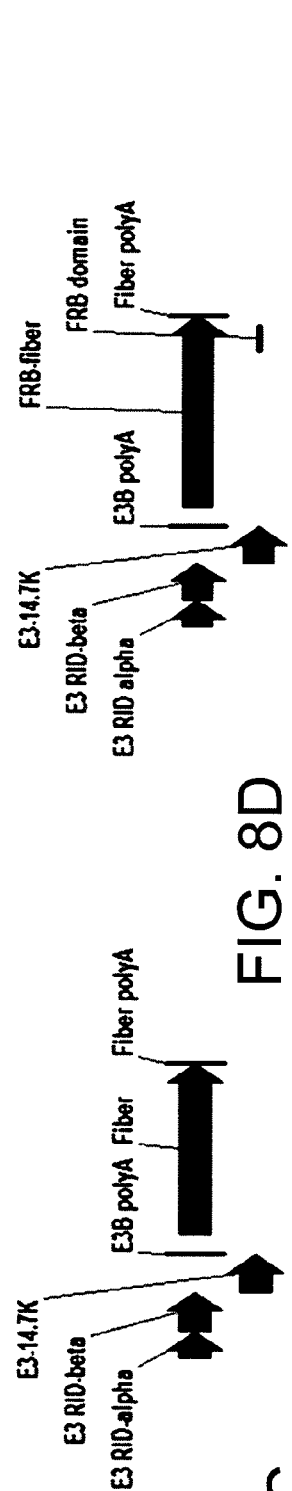
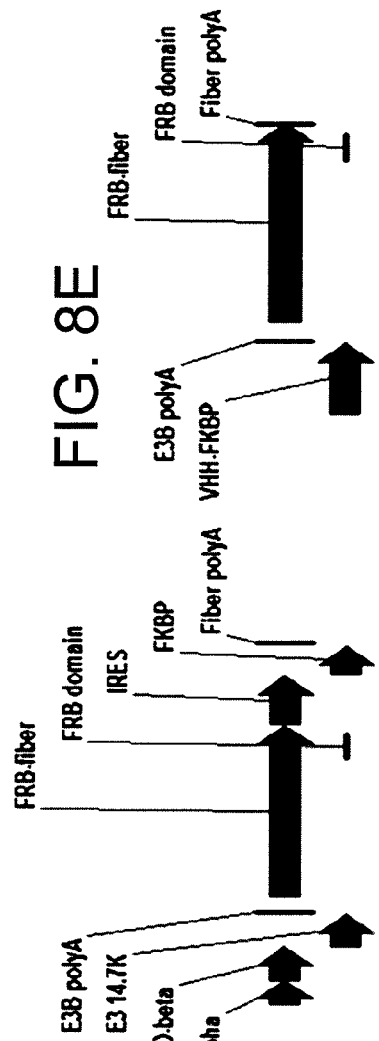
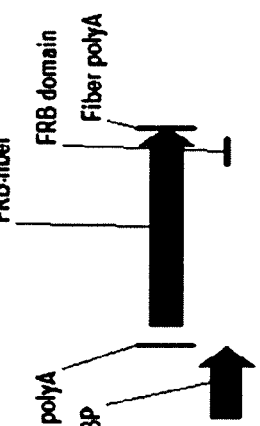
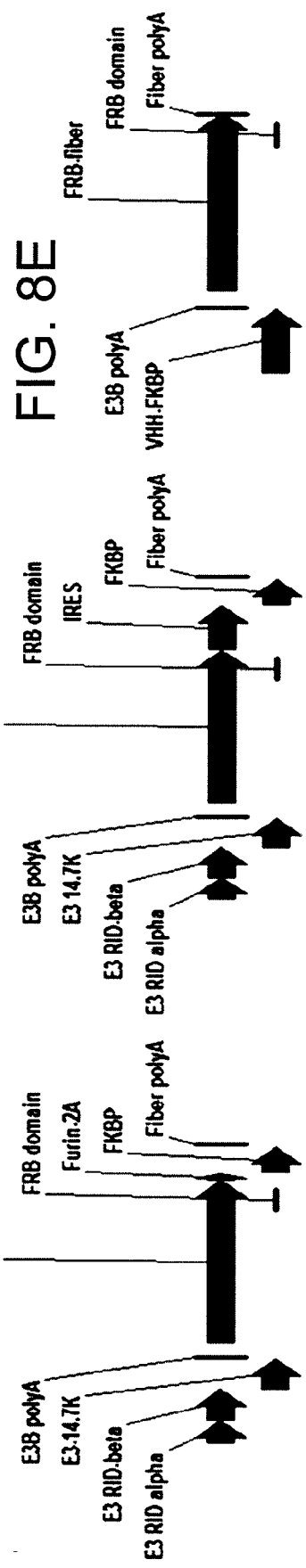
FIG. 8A FIG. 8B FIG. 8C FIG. 8D FIG. 8E Rapamycin [nM]

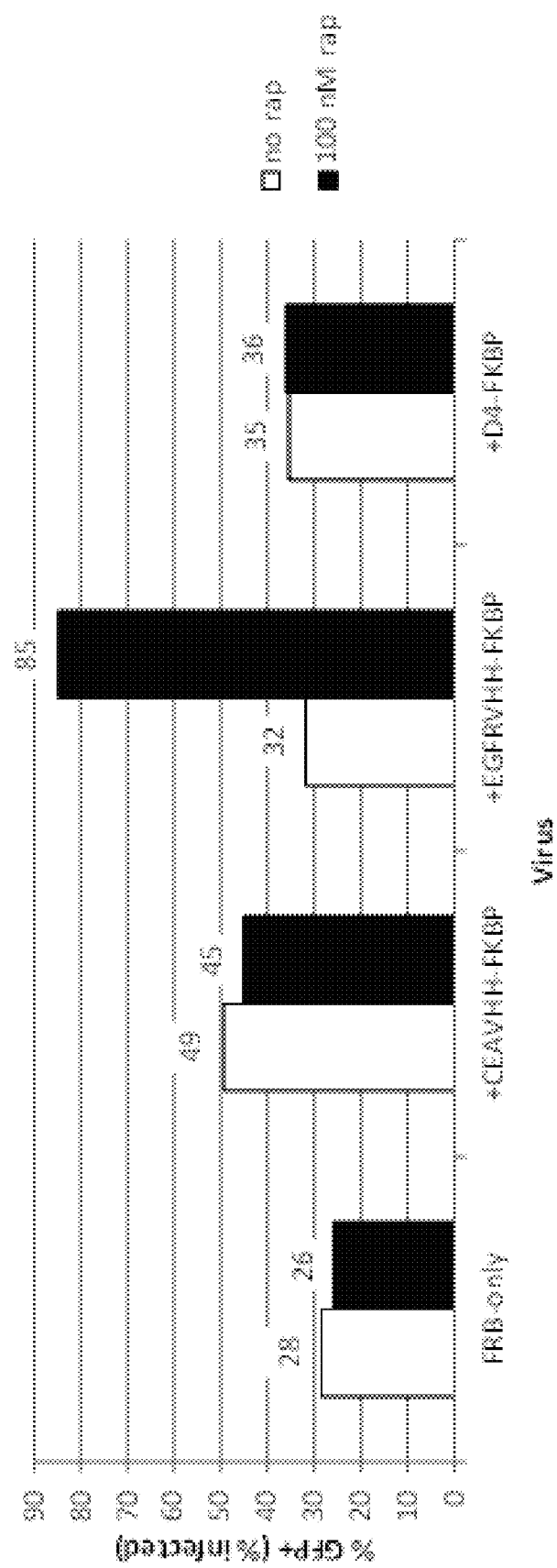

SELECTIVE CELL TARGETING USING ADENOVIRUS AND CHEMICAL DIMERS

CROSS REFERENCE TO RELATED APPLICATIONS

This is a continuation of International Application No. PCT/US2013/031002, filed Mar. 13, 2013, published in English under PCT Article 21(2), which claims the benefit of U.S. Provisional Application No. 61/610,416 filed Mar. 13, 2012. The above-listed applications are hereby incorporated by reference in their entirety.

REFERENCE TO SEQUENCE LISTING

The Sequence Listing is submitted as an ASCII text file, created on Sep. 4, 2014, 762 KB, which is incorporated by reference herein.

BACKGROUND

Cancer is a debilitating disease that accounts for more than half a million deaths each year. There is a profound need for more effective, selective and safe treatments for cancer. Existing treatments for this pervasive, life threatening disease, such as chemotherapy and surgery, rarely eliminate all malignant cells, and often exhibit deleterious side-effects that can outweigh therapeutic benefit.

One approach that has the potential to address many of the shortcomings of current cancer treatments is oncolytic adenoviral therapy (Pesonen, S. et al., *Molecular Pharmaceutics*,. 8(1): p. 12-28 (2010)). These viruses are designed to replicate specifically in cancer cells, but leave normal cells unharmed. One way to engineer tumor selectivity is to target adenovirus infection to receptors upregulated on tumor cells, for example EGFR family members (Zhang H, Berezov A, Wang Q, Zhang G, Drebin J, Murali R, et al. ErbB receptors: from oncogenes to targeted cancer therapies. J Clin Invest. 2007; 117(8):2051-8. PMCID: 1934579), CEACAM (Li H J, Everts M, Pereboeva L, Komarova S, Idan A, Curiel D T, et al. Adenovirus tumor targeting and hepatic untargeting by a coxsackie/adenovirus receptor ectodomain anti-carcinoembryonic antigen bispecific adapter. Cancer Res. 2007; 67(11):5354-61), EpCAM (Haisma H J, Pinedo H M, Rijswijk A, der Meulen-Muileman I, Sosnowski B A, Ying W, et al. Tumor-specific gene transfer via an adenoviral vector targeted to the pan-carcinoma antigen EpCAM. Gene Ther. 1999; 6(8):1469-7), and HLA-A1/MAGE-A1 (de Vrij J, Uil T G, van den Hengel S K, Cramer S J, Koppers-Lalic D, Verweij M C, et al. Adenovirus targeting to HLA-A1/MAGE-A1-positive tumor cells by fusing a single-chain T-cell receptor with minor capsid protein IX. Gene Ther. 2008; 15(13):978-89). For a review of various strategies of adenovirus targeting, see Noureddini S C and Curiel D T (Genetic targeting strategies for adenovirus. Mol Pharm. 2005; 2(5):341-7; Nicklin S A, Wu E, Nemerow G R, Baker A H. The influence of adenovirus fiber structure and function on vector development for gene therapy. Mol Ther. 2005; 12(3):384-93).

Adenovirus (Ad) is a self-replicating biological machine. It consists of a linear double-stranded 36 kb DNA genome sheathed in a protein coat. Ad requires a human host cell to replicate. It invades and hijacks the cellular replicative machinery to reproduce and upon assembly induces lytic cell death to escape the cell and spread and invade surrounding cells (FIG. 1). No ab initio system has come close to mimicking the autonomy and efficiency of Ad, however, Applicants have developed new strategies to systematically manipulate the Ad genome to create novel adenoviruses. Henceforth, with the ability to manipulate the Ad genome, Applicants can take the virus by the horns and redesign it to perform the functions of tumor-specific infection, replication, and cell killing.

Currently, adenoviral vectors rely on a single cellular receptor for their uptake, which significantly limits their therapeutic potential. Ad5 infection is mediated primarily through interactions between the fiber protein on the outer viral capsid and the coxsackie and adenovirus receptor (CAR) on human epithelial cells. Unfortunately, many cancer cells do not express CAR, such as mesenchymal and deadly metastatic tumor cells. Since viral replication/killing is limited by the ability to infect cells, there is a need for viruses that infect tumor cells via receptors other than CAR, ideally those specifically upregulated on tumor cells. The present invention addresses these and other needs in the art by providing viral compositions and methods that chemically link viral capsids via chemical adapters to a broad variety of cellular receptors. Provided herein is a novel, inducible, genetically encoded chemical adapter system that retargets infection to multiple cell types, and is not lost upon viral replication. The compositions provided herein can be used to customize an oncolytic virus to target different cellular receptors over the course of infection.

SUMMARY

In one aspect, a recombinant nucleic acid encoding a capsid-dimerizing agent binder conjugate and a ligand-dimerizing agent binder conjugate are provided.

In another aspect, a recombinant adenovirus including a recombinant nucleic acid provided herein including embodiments thereof is provided.

In another aspect, a recombinant adenovirus including a capsid-dimerizing agent binder conjugate is provided.

In another aspect, a cell including a recombinant adenovirus provided herein including embodiments thereof is provided.

In another aspect, a method of forming an adenoviral cancer cell targeting construct is provided. The method includes infecting a cell with a recombinant adenovirus provided herein, thereby forming an adenoviral infected cell. The adenoviral infected cell is allowed to express the recombinant nucleic acid, thereby forming a ligand-dimerizing agent binder conjugate and a recombinant adenovirus including a capsid-dimerizing agent binder conjugate. The recombinant adenovirus and the ligand-dimerizing agent binder conjugate are contacted with a dimerizing agent. The recombinant adenovirus and the ligand-dimerizing agent binder conjugate are allowed to bind to the dimerizing agent, thereby forming the adenoviral cancer cell targeting construct.

In another aspect, a method of targeting a cell is provided. The method includes contacting a cell with a recombinant adenovirus provided herein including embodiments thereof.

In another aspect, a method of targeting a cancer cell in a cancer patient is provided. The method includes administering to a cancer patient a recombinant adenovirus provided herein. The recombinant adenovirus is allowed to infect a cell in the cancer patient, thereby forming an adenoviral infected cell. The adenoviral infected cell is allowed to express the recombinant nucleic acid, thereby forming a ligand-dimerizing agent binder conjugate and a recombinant adenovirus including a capsid-dimerizing agent binder conjugate. The cancer patient is administered with a dimerizing agent. The recombinant adenovirus and the ligand-dimerizing agent binder conjugate are allowed to bind to the dimerizing agent, thereby forming an adenoviral cancer cell targeting construct. The adenoviral cancer cell targeting construct is allowed to bind to a cancer cell, thereby targeting the cancer cell in the cancer patient.

In another aspect, a method of targeting a cell is provided. The method includes contacting a first cell with a recombinant adenovirus provided herein. The recombinant adenovirus is allowed to infect the first cell, thereby forming an adenoviral infected cell. The adenoviral infected cell is allowed to express the recombinant nucleic acid, thereby forming a ligand-dimerizing agent binder conjugate and a recombinant adenovirus comprising a capsid-dimerizing agent binder conjugate. The ligand-dimerizing agent binder conjugate and the recombinant adenovirus are contacted with a dimerizing agent. The recombinant adenovirus and the ligand-dimerizing agent binder conjugate are allowed to bind to the dimerizing agent, thereby forming an adenoviral cell targeting construct. The adenoviral cell targeting construct is allowed to bind to a second cell, thereby targeting the cell.

BRIEF DESCRIPTION OF THE DRAWINGS

FIG. 3A upper panel: The Ad genome is organized into early (E1-4) and late (L1-5) transcription units that express multiple genes via alternative splicing. Arrows represent multi-gene transcriptional units used by the adenovirus with functional organization reminiscent of operons. The genome is split into transcriptional and functional units ('parts') and cloned into plasmids (FIG. 3A lower panel). The Library of parts includes mutants, alternate serotypes and transgenes. Systematic multi-site specific in vitro re-assembly (Adsembly or Ad-SLIC) and reconstitution of virus is performed. FIG. 3B: the Adenovirus genome (FIG. 3B top panel) is separated into components (FIG. 3B second panel from top). Mutagenesis is performed on individual vectors to build library parts (FIG. 3B third panel form the top) and the virus is assembled in vitro (FIG. 3B bottom panel) to generate novel adenoviruses.

FIG. 7A: Western blot using anti-fiber antibody 4D2 (Abcam) on lysates from Ad-122 and Wt Ad5 infected 293 E4 cells 48 h p.i. FIG. 7B: Bright field and GFP fluorescence images of 293 E4 cells infected with Ad-122 48 h p.i. showing significant CPE.

FIGS. 8A-8E. Genetic configurations to express FRB-Fiber and FKBP from Ad5 E3 region. FIG. 8A: Wild-type Ad5 E3 region. FIG. 8B: FRB insertion into fiber gene. FIG. 8C: Co-translational expression of FKBP using Furin-2A auto-cleavage sequence. FIG. 8 D: Co-transcriptional expression of FKBP using IRES element on fiber transcript. FIG. 8E: Replacement of E3B encoded proteins (RIDα, RIDβ, 14.7k) with FKBP.

FIG. 10A: Model from 'top down' view. FIG. 10B: Model from 'side' view, showing that the binding interface of the VHH is facing away from the virus particle if it is fused to the N-terminus of FKBP.

FIG. 13 left panel represents infections with undiluted viral supernatant; FIG. 13 right panel represents infections with 1/16 dilution of viral supernatant.

FIG. 14 left panel represents infections with undiluted viral supernatant; FIG. 14 right panel represents infections with 1/8 dilution of viral supernatant.

FIG. 15 left panel represents infections with undiluted viral supernatant; FIG. 15 right panel represents infections with 1/8 dilution of viral supernatant.

FIG. 16 left panel represents infections with undiluted viral supernatant; FIG. 16 right panel represents infections with 1/4 dilution of viral supernatant.

FIG. 17 left panel represents infections with undiluted viral supernatant; FIG. 17 right panel represents infections with 1/8 dilution of viral supernatant.

FIG. 21A: Adenovirus with genetically encoded FRB domain insertion in fiber, and EGFRVHH-FKBP fusion protein prepared in the presence or absence of 50 nM rapamycin and used to infect MDA MB 453 cells with or without shRNA-mediated EGFR knockdown. FIG. 21B: Adenovirus with only genetically encoded FRB domain insertion in fiber, prepared in the presence or absence of 50 nM rapamycin and used to infect MDA MB 453 cells with or without shRNA-mediated EGFR knockdown. FIG. 21C: Verification of stable, shRNA-mediated EGFR knockdown in MDA MB 453 cells by protein immunoblot.

FIGS. 23A-23H. Targeted infection of cell lines by control Ad, or by Ad encoding ligands fused to FKBP. The viruses encoded either the CEACAM single domain antibody fragment fused to FKBP (CEAVHH-FKBP), the EGFR single domain antibody fragment fused to FKBP (EGFRVHH-FKBP), or domain 4 of protective antigen fused to FKBP (D4-FKBP). The adenoviruses were prepared in the presence or absence of 100 nM rapamycin by infection of 293 E4 cells, and supernatant was used to infect the targeted cell lines: FIG. 23A shows infection of MDA MB231. FIG. 23B shows infection of MDA MB453. FIG. 23C shows infection of MDA MB468. FIG. 23D shows infection of HS578T. FIG. 23E shows infection of BT474. FIG. 23F shows infection of MCF7. FIG. 23G shows infection of CHO K1. FIG. 23H shows infection of CHO R1.1. Numbers on top of the columns represent % of GFP (i.e. infected) cells.

FIG. 24A shows infection of MDA MB453. FIG. 24B shows infection of MDA MB468. FIG. 24C shows infection of MDA HS578T. FIG. 24D shows infection of MDA MCF7. Numbers on top of the columns represent % of GFP (i.e. infected) cells.

FIG. 27A upper panel shows infection of MDA MB231. FIG. 27A middle panel shows infection of MDA MB453. FIG. 27A lower panel shows infection of MDA MB468. FIG. 27B upper panel shows infection of HS578T. FIG. 27B middle panel shows infection of BT474. FIG. 27B lower panel shows infection of MCF7. FIG. 27C upper panel shows infection of CHO K1. FIG. 27C lower panel shows infection of CHO R1.1. Numbers on top of the columns represent % of GFP (i.e. infected) cells.

DETAILED DESCRIPTION

I. Definitions

Figure 1:
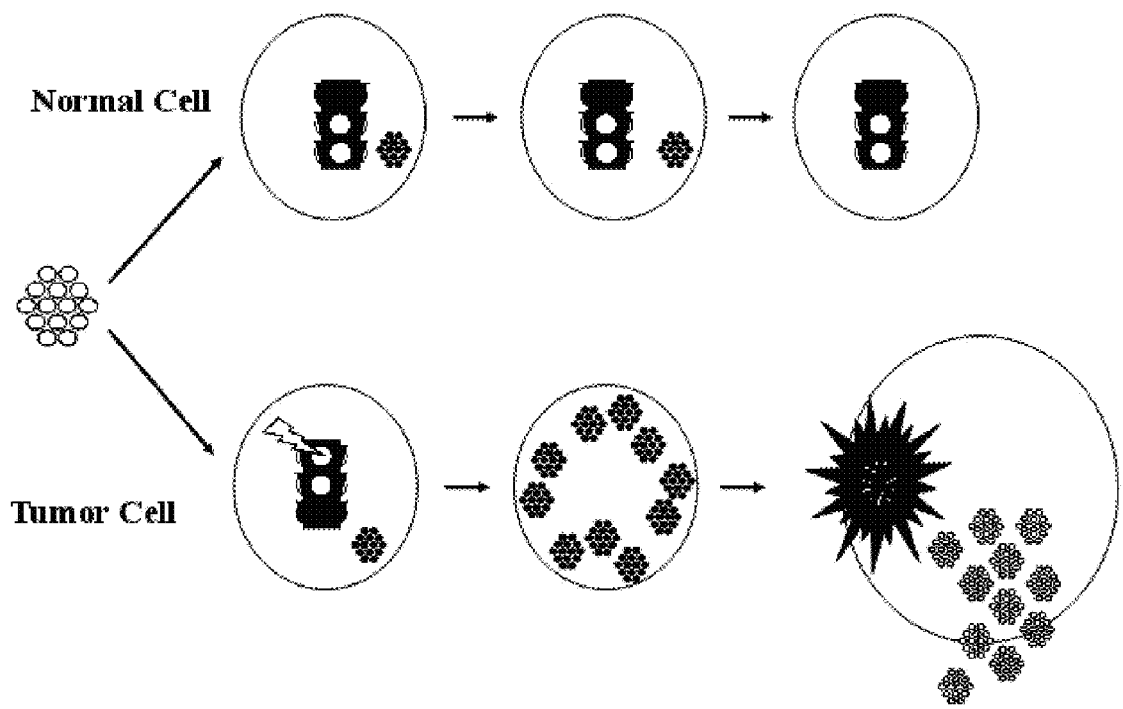
FIG. 1. General rationale of oncolytic viral cancer therapy.

"Nucleic acid" refers to deoxyribonucleotides or ribonucleotides and polymers thereof in either single- or double-stranded form, and complements thereof. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

The terms "Ad5" and "Adenoviral genome" as used herein refer to the nucleic sequence as set forth in SEQ ID NO: 108.

Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); Rossolini et al., *Mol. Cell. Probes* 8:91-98 (1994)). The term nucleic acid is used interchangeably with gene, cDNA, mRNA, oligonucleotide, and polynucleotide.

A particular nucleic acid sequence also implicitly encompasses "splice variants." Similarly, a particular protein encoded by a nucleic acid implicitly encompasses any protein encoded by a splice variant of that nucleic acid. "Splice variants," as the name suggests, are products of alternative splicing of a gene. After transcription, an initial nucleic acid transcript may be spliced such that different (alternate) nucleic acid splice products encode different polypeptides. Mechanisms for the production of splice variants vary, but include alternate splicing of exons. Alternate polypeptides derived from the same nucleic acid by read-through transcription are also encompassed by this definition. Any products of a splicing reaction, including recombinant forms of the splice products, are included in this definition. An example of potassium channel splice variants is discussed in Leicher, et al., *J. Biol. Chem.* 273(52):35095-35101 (1998).

Construction of suitable vectors containing the desired therapeutic gene coding and control sequences may employ standard ligation and restriction techniques, which are well understood in the art (see Maniatis et al., in Molecular Cloning: A Laboratory Manual, Cold Spring Harbor Laboratory, New York (1982)). Isolated plasmids, DNA sequences, or synthesized oligonucleotides may be cleaved, tailored, and re-ligated in the form desired.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are near each other, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

The terms "identical" or percent "identity," in the context of two or more nucleic acids or polypeptide sequences, refer to two or more sequences or subsequences that are the same or have a specified percentage of amino acid residues or nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection (see, e.g., NCBI web site or the like). Such sequences are then said to be "substantially identical." This definition also refers to, or may be applied to, the compliment of a test sequence. The definition also includes sequences that have deletions and/or additions, as well as those that have substitutions. As described below, the preferred algorithms can account for gaps and the like. Preferably, identity exists over a region that is at least about 25 amino acids or nucleotides in length, or more preferably over a region that is 50-100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds. 1995 supplement)).

A preferred example of algorithm that is suitable for determining percent sequence identity and sequence similarity are the BLAST and BLAST 2.0 algorithms, which are described in Altschul et al., *Nuc. Acids Res.* 25:3389-3402 (1977) and Altschul et al., *J. Mol. Biol.* 215:403-410 (1990), respectively. BLAST and BLAST 2.0 are used, with the parameters described herein, to determine percent sequence identity for the nucleic acids and proteins of the invention. Software for performing BLAST analyses is publicly available through the National Center for Biotechnology Information, as known in the art. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, *Proc. Natl. Acad. Sci. USA* 89:10915 (1989)) alignments (B) of 50, expectation (E) of 10, M=5, N=−4, and a comparison of both strands.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence with respect to the expression product, but not with respect to actual probe sequences.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, *Proteins* (1984)).

The term "recombinant" when used with reference, e.g., to a cell, virus, nucleic acid, protein, or vector, indicates that the cell, virus, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all.

The phrase "stringent hybridization conditions" refers to conditions under which a probe will hybridize to its target subsequence, typically in a complex mixture of nucleic acids, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may also be achieved with the addition of destabilizing agents such as formamide. For selective or specific hybridization, a positive signal is at least two times background, preferably 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C.

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency. Additional guidelines for determining hybridization parameters are provided in numerous reference, e.g., and *Current Protocols in Molecular Biology*, ed. Ausubel, et al., John Wiley & Sons.

For PCR, a temperature of about 36° C. is typical for low stringency amplification, although annealing temperatures may vary between about 32° C. and 48° C. depending on primer length. For high stringency PCR amplification, a temperature of about 62° C. is typical, although high stringency annealing temperatures can range from about 50° C. to about 65° C., depending on the primer length and specificity. Typical cycle conditions for both high and low stringency amplifications include a denaturation phase of 90° C.-95° C. for 30 sec-2 min., an annealing phase lasting 30 sec.-2 min., and an extension phase of about 72° C. for 1-2 min. Protocols and guidelines for low and high stringency amplification reactions are provided, e.g., in Innis et al. (1990) *PCR Protocols, A Guide to Methods and Applications*, Academic Press, Inc. N.Y.).

The terms "transfection", "transduction", "transfecting" or "transducing" can be used interchangeably and are defined as a process of introducing a nucleic acid molecule or a protein to a cell. Nucleic acids are introduced to a cell using non-viral or viral-based methods. The nucleic acid molecule can be a sequence encoding complete proteins or functional portions thereof. Typically, a nucleic acid vector, comprising the elements necessary for protein expression (e.g., a promoter, transcription start site, etc.). Non-viral methods of transfection include any appropriate method that does not use viral DNA or viral particles as a delivery system to introduce the nucleic acid molecule into the cell. Exemplary non-viral transfection methods include calcium phosphate transfection, liposomal transfection, nucleofection, sonoporation, transfection through heat shock, magnetifection and electroporation. For viral-based methods, any useful viral vector can be used in the methods described herein. Examples of viral vectors include, but are not limited to retroviral, adenoviral, lentiviral and adeno-associated viral vectors. In some aspects, the nucleic acid molecules are introduced into a cell using a adenoviral vector following standard procedures well known in the art. The terms "transfection" or "transduction" also refer to introducing proteins into a cell from the external environment. Typically, transduction or transfection of a protein relies on attachment of a peptide or protein capable of crossing the cell membrane to the protein of interest. See, e.g., Ford et al. (2001) *Gene Therapy* 8:1-4 and Prochiantz (2007) *Nat. Methods* 4:119-20.

Expression of a transfected gene can occur transiently or stably in a host cell. During "transient expression" the transfected nucleic acid is not integrated into the host cell genome, and is not transferred to the daughter cell during cell division. Since its expression is restricted to the transfected cell, expression of the gene is lost over time. In contrast, stable expression of a transfected gene can occur when the gene is co-transfected with another gene that confers a selection advantage to the transfected cell. Such a selection advantage may be a resistance towards a certain toxin that is presented to the cell. Expression of a transfected gene can further be accomplished by transposon-mediated insertion into to the host genome. During transposon-mediated insertion, the gene is positioned in a predictable manner between two transposon linker sequences that allow insertion into the host genome as well as subsequent excision.

"FKBP" or an "FKBP protein or polypeptide" as referred to herein includes any of the naturally-occurring forms of the FKBP protein, or variants thereof that maintain FKBP protein activity (e.g. within at least 50%, 80%, 90%, 95%, 96%, 97%, 98%, 99% or 100% activity compared to FKBP). In some embodiments, variants have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring FKBP protein as set forth in SEQ ID NO:66.

"FRB" or an "FRB protein or polypeptide" as referred to herein includes any of the naturally-occurring forms of the FRB protein, or variants thereof that maintain FRB protein activity (e.g. within at least 50%, 80%, 90%, 95%, 96%, 97%, 98%, 99% or 100% activity compared to FRB). In some embodiments, variants have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring FRB protein as set forth in SEQ ID NO:69.

"EGFR" refers to the epidermal growth factor receptor corresponding to the amino acid sequence as set forth in SEQ ID NO:21.

"VHH" refers to a single domain antibody consisting of a single monomeric variable antibody domain that is capable of selectively binding to a specific antigen (e.g. EGFR). VHH single-domain antibodies may be engineered from heavy-chain antibodies found in camelids. The terms VHH or VHH are used interchangeably throughout and are used according to their common meaning in the art. An "EGFR VHH" or "a EGFR VHH protein" as provided herein refers to a VHH single domain antibody specifically binding to EGFR. In some embodiments, the EGFR VHH has the sequence set forth in SEQ ID NO: 4. In further embodiments, EGFR VHH is operably linked to FKBP to form a ligand-dimerizing agent binder conjugate. In some further embodiments, the ligand-dimerizing agent binder conjugate has the sequence set forth in SEQ ID NO: 6.

"CEA" or CEACAM5" as provided herein refers to carcinoembryonic antigen-related cell adhesion molecule 5 also known in the art as CD66. "CEA VHH" or "a CEA VHH protein" as provided herein refers to a VHH single domain antibody specifically binding to CEA. In some embodiments, the CEA VHH has the sequence set forth in SEQ ID NO: 1. In further embodiments, the CEA VHH is operably linked to FKBP to form a ligand-dimerizing agent binder conjugate. In some further embodiments, the ligand-dimerizing agent binder conjugate has the amino acid sequence set forth in SEQ ID NO: 3.

A "protective antigen domain 4 (D4) protein" provided herein refers to the *Bacillus anthracis* protective antigen domain 4 as set forth in SEQ ID NO: 94. In some embodiments, D4 is operably linked to FKBP to form a ligand-dimerizing agent binder conjugate. In some further embodiments, the ligand-dimerizing agent binder conjugate has the amino acid sequence set forth in SEQ ID NO: 9.

A "control" sample or value refers to a sample that serves as a reference, usually a known reference, for comparison to a test sample. For example, a test sample can be taken from a test condition, e.g., in the presence of a test compound, and compared to samples from known conditions, e.g., in the absence of the test compound (negative control), or in the presence of a known compound (positive control). A control can also represent an average value gathered from a number of tests or results. One of skill in the art will recognize that controls can be designed for assessment of any number of parameters. For example, a control can be devised to compare therapeutic benefit based on pharmacological data (e.g., half-life) or therapeutic measures (e.g., comparison of side effects). One of skill in the art will understand which controls are valuable in a given situation and be able to analyze data based on comparisons to control values. Controls are also valuable for determining the significance of data. For example, if values for a given parameter are widely variant in controls, variation in test samples will not be considered as significant.

As used herein, the term "cancer" refers to all types of cancer, neoplasm, or malignant tumors found in mammals, including leukemia, carcinomas and sarcomas. Exemplary cancers include cancer of the brain, breast, cervix, colon, head & neck, liver, kidney, lung, non-small cell lung, melanoma, mesothelioma, ovary, sarcoma, stomach, uterus and Medulloblastoma. Additional examples include, Hodgkin's Disease, Non-Hodgkin's Lymphoma, multiple myeloma, neuroblastoma, ovarian cancer, rhabdomyosarcoma, primary thrombocytosis, primary macroglobulinemia, primary brain tumors, cancer, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, endometrial cancer, adrenal cortical cancer, neoplasms of the endocrine and exocrine pancreas, and prostate cancer.

The term "leukemia" refers broadly to progressive, malignant diseases of the blood-forming organs and is generally characterized by a distorted proliferation and development of leukocytes and their precursors in the blood and bone marrow. Leukemia is generally clinically classified on the basis of (1) the duration and character of the disease-acute or chronic; (2) the type of cell involved; myeloid (myelogenous), lymphoid (lymphogenous), or monocytic; and (3) the increase or non-increase in the number abnormal cells in the blood-leukemic or aleukemic (subleukemic). The $P_{388}$ leukemia model is widely accepted as being predictive of in vivo anti-leukemic activity. It is believed that a compound that tests positive in the $P_{388}$ assay will generally exhibit some level of anti-leukemic activity in vivo regardless of the type of leukemia being treated. Accordingly, the present invention includes a method of treating leukemia, and, preferably, a method of treating acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, multiple myeloma, plasmacytic leukemia, promyelocytic leukemia, Rieder cell leukemia, Schilling's leukemia, stem cell leukemia, subleukemic leukemia, and undifferentiated cell leukemia.

The term "sarcoma" generally refers to a tumor which is made up of a substance like the embryonic connective tissue and is generally composed of closely packed cells embedded in a fibrillar or homogeneous substance. Sarcomas which can be treated with a combination of antineoplastic thiol-binding mitochondrial oxidant and an anticancer agent include a chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, and telangiectaltic sarcoma.

The term "melanoma" is taken to mean a tumor arising from the melanocytic system of the skin and other organs. Melanomas which can be treated with a combination of antineoplastic thiol-binding mitochondrial oxidant and an anticancer agent include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma, subungal melanoma, and superficial spreading melanoma.

The term "carcinoma" refers to a malignant new growth made up of epithelial cells tending to infiltrate the surrounding tissues and give rise to metastases. Exemplary carcinomas which can be treated with a combination of antineoplastic thiol-binding mitochondrial oxidant and an anticancer agent include, for example, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatiniforni carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypemephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, nasopharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tuberous carcinoma, verrucous carcinoma, and carcinoma villosum.

By "therapeutically effective dose or amount" herein is meant a dose that produces effects for which it is administered. The exact dose and formulation will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); *Remington: The Science and Practice of Pharmacy*, 20th Edition, Gennaro, Editor (2003), and Pickar, *Dosage Calculations* (1999)).

The term "pharmaceutically acceptable salts" or "pharmaceutically acceptable carrier" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, e.g., Berge et al., *Journal of Pharmaceutical Science* 66:1-19 (1977)). Certain specific compounds of the present invention contain both basic and acidic functionalities that allow the compounds to be converted into either base or acid addition salts. Other pharmaceutically acceptable carriers known to those of skill in the art are suitable for the present invention.

A "subject," "individual," or "patient," is used interchangeably herein, which refers to a vertebrate, preferably a mammal, more preferably a human. Mammals include, but are not limited to, murine, simian, human, farm animals, sport animals, and pets. Tissues, cells and their progeny of a biological entity obtained in vitro or cultured in vitro are also encompassed.

II. Compositions

Provided herein, inter alia, are adenoviral compositions useful for infecting a broad variety of different cell types (e.g. cancer cells). For example, the compositions provided herein may be used to retarget adenovirus infection to receptors upregulated on tumor cells (e.g. EGFR, CEA, ErbB). Using the compositions provided herein including embodiments thereof, the heterogeneity of tumors can be overcome by designing recombinant adenoviruses that are able to infect tumor cells through more than one receptor. The viral compositions provided herein express polypeptide binding pairs (as listed in Table 2, e.g. FKBP and FRB) capable of dimerizing in the presence of a chemical dimerizing agent (e.g. rapamycin) and thereby forming a ternary complex. The ternary complex enables the virus to bind to a specific cellular surface receptor. The components of the ternary complex may completely or partially be encoded by the adenoviral genome and are therefore not lost during viral replication providing for the ability of the virus of subsequent re-infection. Thus, in one aspect, a recombinant nucleic acid encoding a capsid-dimerizing agent binder conjugate and a ligand-dimerizing agent binder conjugate are provided. The capsid-dimerizing agent binder conjugate includes a dimerizing agent binder (e.g. FRB) operably linked to a viral capsid protein (e.g. fiber). A dimerizing agent binder as provided herein is an agent capable of binding a dimerizing agent. A dimerizing agent binder includes without limitation a protein, a compound or a small molecule. In some embodiments, the dimerizing agent binder is a FRB protein. Non limiting examples of dimerizing agent binders are set forth in Table 2 provided herein. Binding of the dimerizing agent binder to the dimerizing agent may occur through non-covalent intermolecular interactions such as hydrogen bonding, electrostatic interactions, hydrophobic and Van der Waals forces. The capsid-dimerizing agent binder conjugate includes a viral capsid protein. The term capsid refers to any component (e.g. capsid proteins or polypeptides) forming the shell of a virus, wherein the capsid can include one or more of these components. The capsid includes any appropriate structural components of the viral shell. In some embodiments, the capsid protein is an adenoviral capsid protein. Non-limiting examples of capsid proteins are L3 II (hexon) (e.g. encoding major structural proteins that form the triangular faces of the capsid), L1 IIIa (e.g. encoding minor structural proteins that help to stabilize the capsid), L2 III (penton) (e.g. encoding major structural proteins that form the vertex of the capsid where the fiber protrudes), L2 pVII (e.g. encoding core structural proteins with homology to histone H3 and associate with viral DNA in the capsid), and L5 IV (Fiber) (e.g. encoding major structural proteins that extend from the penton base and are responsible for receptor binding). In some embodiments, the adenoviral capsid protein is a fiber protein.

Upon expression in a cell the dimerizing agent binder and the viral capsid protein form a capsid-dimerizing agent binder conjugate, which is capable of binding to a dimerizing agent (e.g. rapamycin) through the dimerizing agent binder (e.g. FRB) and is incorporated into the viral capsid by the capsid protein (e.g. fiber). Thus, in some embodiments, the capsid-dimerizing agent binder conjugate includes a capsid protein and a dimerizing agent binder. In other embodiments, the capsid protein is operably linked to the dimerizing agent binder. Through binding to the dimerizing agent the capsid-dimerizing agent binder conjugate may connect to the ligand-dimerizing agent binder conjugate. The ligand-dimerizing agent binder conjugate includes a cell surface receptor-specific ligand (e.g. EGFR VHH) operably linked to a second dimerizing agent binder (e.g. FKBP). A ligand as provided herein is a protein with the capability of binding a molecule expressed on the surface of a cell. Non-limiting examples of ligands and corresponding cellular receptors are set forth in Table 3. In some embodiments, the ligand is a EGFR VHH protein. In a further embodiment, the dimerizing agent binder is FKBP. In some embodiments, the ligand is a CEA VHH protein. In a further embodiment, the dimerizing agent binder is FKBP. In some embodiments, the ligand is a protective antigen domain 4 (D4) protein. In a further embodiment, the dimerizing agent binder is FKBP. In some embodiments, the ligand-dimerizing agent binder conjugate includes a ligand and a dimerizing agent binder. In some embodiments, the ligand is operably linked to the dimerizing agent binder. In some embodiments, the ligand is an antibody. In some further embodiments, the antibody is a single domain antibody. In some embodiments, a plurality of ligands is operably linked to the dimerizing agent binder, wherein the plurality of ligands are individually different. The plurality of ligands may be operably linked to one or both termini of the dimerizing agent binder. In some embodiments, the plurality of ligands is operably linked in tandem to one or both termini of the dimerizing agent binder. In some embodiments, the dimerizing agent binder is an immunophilin protein. In some further embodiments, the immunophilin protein is a FKBP protein. In some further embodiments, the FKBP protein is a human FKBP protein. In some further embodiments, the human FKBP protein is FKBP12. In other embodiments, the ligand is capable of binding a cell. In other embodiments, the cell is a tumor cell.

Provided herein, inter alia, are recombinant adenoviruses expressing the recombinant nucleic acid described above. Thus, in another aspect, a recombinant adenovirus including a recombinant nucleic acid provided herein including embodiments thereof is provided. In some embodiments, the adenovirus is a replication incompetent adenovirus. In other embodiments, the adenovirus is a replication competent adenovirus. Where the adenovirus is a replication competent adenovirus, the adenovirus is capable of infecting a cell by binding to a specific cellular surface receptor (e.g. EGFR), replicating inside said cell thereby producing new viral progeny capable of infecting additional cells. In contrast, a replication incompetent adenovirus, is capable of entering a cell by binding to a specific cellular receptor and expressing the adenoviral genome inside said cell. However, a replication incompetent virus lacks genes necessary to produce new viral progeny and therefore is not capable of subsequent infection of additional cells.

In another aspect, a recombinant adenovirus including a capsid-dimerizing agent binder conjugate is provided. As described above a capsid-dimerizing agent binder conjugate includes a capsid protein (e.g. fiber) operably linked to a dimerizing agent binder (e.g. FRB). The binding of the dimerizing agent binder (e.g. FRB) to the dimerizing agent (e.g. rapamycin) therefore connects the recombinant adenovirus to the dimerizing agent. Thus, the recombinant adenovirus including a capsid-dimerizing agent binder conjugate may be bound to a dimerizing agent. A dimerizing agent as provided herein is an agent capable of binding a dimerizing agent binder of a capsid-dimerizing agent binder conjugate and a dimerizing agent binder of a ligand-dimerizing agent binder conjugate. In some embodiments, the dimerizing agent binds a dimerizing agent binder of a capsid-dimerizing agent binder conjugate. The dimerizing agent may bind a dimerizing agent binder of a ligand-dimerizing agent binder conjugate and a dimerizing agent binder of a ligand-dimerizing agent binder conjugate. Thus, in some embodiments, the dimerizing agent is further bound to a ligand-dimerizing agent binder conjugate. A dimerizing agent may bind the dimerizing agent binder through non-covalent intermolecular interactions such as hydrogen bonding, electrostatic interactions, hydrophobic and Van der Waals forces. In some embodiments, the dimerizing agent binds covalently to the dimerizing agent binder. The dimerizing agent as provided herein may be a naturally occurring substance (e.g. rapamycin, abscisic acid) or a synthetic substance (e.g. a small molecule, a compound). Examples of dimerizing agents according to the invention provided herein are listed in Table 2. In some embodiments, the dimerizing agent is a compound. In some further embodiments, the compound is rapamycin. Rapamycin refers, in the customary sense, to CAS Registry No. 53123-88-9. Rapamycin inhibits the mTOR kinase and is used as an immunosuppressing agent and anti-cancer treatment. In some further embodiments, the dimerizing agent is a rapalog. A rapalog as provided herein is a rapamycin analog does not inhibit cellular mTOR kinase activity. In some further embodiment, the rapalog is AP21967. In some embodiments, the dimerizing agent is an anti-cancer drug.

As described above, the compositions provided herein include a recombinant adenovirus including a recombinant nucleic acid including a capsid-dimerizing agent binder and a ligand-dimerizing agent binder conjugate. Therefore, the recombinant adenovirus may further include a ligand-dimerizing agent binder conjugate. In other embodiments, the ligand-dimerizing agent binder conjugate is ectopically expressed. Wherein the ligand-dimerizing agent binder conjugate is ectopically expressed, the nucleic acid encoding the ligand-dimerizing agent binder conjugate does not form part of the recombinant nucleic acid included in the recombinant adenovirus. Where the ligand-dimerizing agent binder conjugate is ectopically expressed it may be encoded by the genome of the cell infected with the recombinant adenovirus.

In some embodiments, the recombinant adenovirus includes a plurality of ligand-dimerizing agent binder conjugates, wherein each ligand-dimerizing agent binder conjugate may be different. For example where the recombinant adenovirus includes a plurality of ligand-dimerizing agent binder conjugates, the recombinant adenovirus may include a first ligand-dimerizing agent binder conjugate, a second ligand-dimerizing agent binder conjugate and a third ligand-dimerizing agent binder conjugate with each ligand-dimerizing agent binder conjugate being different. Thus, the first ligand-dimerizing agent binder conjugate may include a first ligand and a first dimerizing agent binder, the second ligand-dimerizing agent binder conjugate may include a second ligand and a second dimerizing agent binder, wherein the first ligand is different from the second ligand and the first dimerizing agent binder is the same or different from the second dimerizing agent binder. For example, the first ligand-EGFR VHH may be operably linked to the first dimerizing agent binder FKBP and the second ligand CEA VHH may be operably linked to the second dimerizing agent binder AB1 or FKBP.

Moreover, the recombinant adenovirus may include a plurality of capsid-dimerizing agent binder conjugates, wherein each capsid-dimerizing agent binder conjugate may be different. For example where the recombinant adenovirus includes a plurality of capsid-dimerizing agent binder conjugates, the recombinant adenovirus may include a first capsid-dimerizing agent binder conjugate, a second capsid-dimerizing agent binder conjugate and a third capsid-dimerizing agent binder conjugate with each capsid-dimerizing agent binder conjugate being different. Thus, the first capsid-dimerizing agent binder conjugate may include a first capsid protein and a first dimerizing agent binder, the second capsid-dimerizing agent binder conjugate may include a second capsid protein and a second dimerizing agent binder, wherein the first and second capsid protein may be the same or different and the first and second dimerizing agent binder may the same or different. For example, the first capsid protein fiber may be operably linked to the first dimerizing agent binder FRB and the second capsid protein fiber may be operably linked to the second dimerizing agent binder PYL1. Thus, in one embodiment, the recombinant adenovirus includes a first capsid-dimerizing agent binder conjugate (e.g. fiber/FRB), a first ligand-dimerizing agent binder conjugate (e.g. EGFR VHH/FKBP), a second capsid-dimerizing agent binder conjugate (e.g. fiber/PYL1) and a second ligand-dimerizing agent binder conjugate (e.g. CEA VHH/AB1). In the presence of a first dimerizing agent (i.e. rapamycin) the first capsid-dimerizing agent binder conjugate and the first ligand-dimerizing agent binder conjugate are connected through the binding of FRB and FKBP to rapamycin. In the presence of a second dimerizing agent (i.e. abscisic acid) the second capsid-dimerizing agent binder conjugate and the second ligand-dimerizing agent binder conjugate are connected through the binding of AB1 and Pyl1 to abscisic acid. Therefore, in the presence of rapamycin the recombinant adenovirus infects cells expressing the EGF receptor and in the presence of abscisic acid the same virus may infect cells expressing CEA. Thus, the same recombinant adenovirus is capable of infecting different cell types depending on the presence of dimerizing agent administered.

In another aspect, a cell including a recombinant adenovirus provided herein including embodiments thereof is provided. In some embodiments, the cell is a cancer cell in a cancer patient. In other embodiments, the cell is a non-cancer cell in a cancer patient. In some embodiments, the cell is a cell in an organism. In some further embodiments, the organism is a mammal. In some further embodiments, the mammal is a human. In other embodiments, the cell is a cell in a culture vessel. In some further embodiments, the cell is a transformed cell.

III. Methods

In another aspect, a method of forming an adenoviral cancer cell targeting construct is provided. The method includes infecting a cell with a recombinant adenovirus provided herein, thereby forming an adenoviral infected cell. The adenoviral infected cell is allowed to express the recombinant nucleic acid, thereby forming a ligand-dimerizing agent binder conjugate and a recombinant adenovirus including a capsid-dimerizing agent binder conjugate. The recombinant adenovirus and the ligand-dimerizing agent binder conjugate are contacted with a dimerizing agent. The recombinant adenovirus and the ligand-dimerizing agent binder conjugate are allowed to bind to the dimerizing agent, thereby forming the adenoviral cancer cell targeting construct. As described above, the recombinant nucleic acid may include a plurality of capsid-dimerizing agent binder conjugates and ligand-dimerizing agent binder conjugates, thereby enabling the adenovirus expressing the recombinant nucleic acid to bind to plurality of different cellular surface receptors.

In another aspect, a method of targeting a cell is provided. The method includes contacting a cell with a recombinant adenovirus provided herein including embodiments thereof. In some embodiments, the cell is a cancer cell.

In another aspect, a method of targeting a cancer cell in a cancer patient is provided. The method includes administering to a cancer patient a recombinant adenovirus provided herein. The recombinant adenovirus is allowed to infect a cell in the cancer patient, thereby forming an adenoviral infected cell. The adenoviral infected cell is allowed to express the recombinant nucleic acid, thereby forming a ligand-dimerizing agent binder conjugate and a recombinant adenovirus including a capsid-dimerizing agent binder conjugate. The cancer patient is administered with a dimerizing agent. The recombinant adenovirus and the ligand-dimerizing agent binder conjugate are allowed to bind to the dimerizing agent, thereby forming an adenoviral cancer cell targeting construct. The adenoviral cancer cell targeting construct is allowed to bind to a cancer cell, thereby targeting the cancer cell in the cancer patient. In some embodiments, the cell is a cancer cell. In other embodiments, the cell is a non-cancer cell.

In another aspect, a method of targeting a cell is provided. The method includes contacting a first cell with a recombinant adenovirus provided herein. The recombinant adenovirus is allowed to infect the first cell, thereby forming an adenoviral infected cell. The adenoviral infected cell is allowed to express the recombinant nucleic acid, thereby forming a ligand-dimerizing agent binder conjugate and a recombinant adenovirus comprising a capsid-dimerizing agent binder conjugate. The ligand-dimerizing agent binder conjugate and the recombinant adenovirus are contacted with a dimerizing agent. The recombinant adenovirus and the ligand-dimerizing agent binder conjugate are allowed to bind to the dimerizing agent, thereby forming an adenoviral cell targeting construct. The adenoviral cell targeting construct is allowed to bind to a second cell, thereby targeting said cell. In some embodiments, the first cell and the second cell form part of an organism.

IV. Specific Embodiments

Cancer is a debilitating disease that accounts for more than half a million deaths each year. There is a profound need for more effective, selective and safe treatments for cancer. Existing treatments for this pervasive, life threatening disease, such as chemotherapy and surgery, rarely eliminate all malignant cells, and often exhibit deleterious side-effects that can outweigh therapeutic benefit. The present invention provides powerful recombinant viruses that are capable of infecting tumor cells via disparate receptors. These viruses will enable a new safe form of effective, self-amplifying therapy that breaks the paradigm of systemic genotoxic treatments for cancer.

One approach that has the potential to address many of the shortcomings of current cancer treatments is oncolytic adenoviral therapy (Pesonen, S. et al., *Molecular Pharmaceutics*, 8(1): p. 12-28 (2010)). These viruses are designed to replicate specifically in cancer cells, but leave normal cells unharmed. This selectivity can be engineered by exploiting the functional overlap between adenoviral, early onco-proteins, such as E1A, and tumor mutations in the Rb tumor suppressor pathway which drives deregulated cell cycle entry and pathological DNA replication (Poznic, M., *J Biosci*, 34(2): p. 305-12 (2009)).

Adenovirus (Ad) is a self-replicating biological machine. It consists of a linear double-stranded 36 kb DNA genome sheathed in a protein coat. Ad requires a human host cell to replicate. It invades and hijacks the cellular replicative machinery to reproduce and upon assembly induces lytic cell death to escape the cell and spread and invade surrounding cells (FIG. 1). No ab initio system has come close to mimicking the autonomy and efficiency of Ad, however, Applicants have developed two new strategies to systematically manipulate the Ad genome to create novel adenoviruses as described in published application PCT/US2011/048006, which is herein incorporated in its entirety and for all purposes. Henceforth, with the ability to manipulate the Ad genome, Applicants can take the virus by the horns and redesign it to perform the functions of tumor-specific infection, replication, and cell killing.

Currently, adenoviral vectors rely on a single cellular receptor for their uptake, which significantly limits their therapeutic potential. Ad5 infection is mediated primarily through interactions between the fiber protein on the outer viral capsid and the coxsackie and adenovirus receptor (CAR) on human epithelial cells. Unfortunately, many cancer cells do not express CAR, such as mesenchymal and deadly metastatic tumor cells. Since viral replication/killing will be limited by the ability to infect cells, Applicants need viruses that infect tumor cells via receptors other than CAR, ideally those specifically upregulated on tumor cells. Provided herein are genetically-encoded switchable targeting moieties that enable Ad5 to infect cancer cells regardless of their CAR-expression. Applicants used a known property of the cancer drug rapamycin (rap) to dimerize heterologous proteins with FKBP and FRB domains and engineered viruses that express a FRB-fiber capsid protein fusion together with retargeting ligands fused to FKBP. These viruses are induced to infect any cell type via multiple retargeting ligands upon rap treatment. This represents a rational and powerful combination of chemical and viral weapons as a novel cancer therapy. In addition, a major goal is to overcome tumor heterogeneity by engineering viruses that are able to infect tumor cells through more than one more mechanism and receptor. Applicants achieved this by using a known property of the cancer drug rapamycin (rap) to dimerize heterologous proteins with FKBP and FRB domains. Rapamycin inhibits the mTOR kinase and is used as an immunosuppressing agent and anti-cancer treatment. By engineering FRB mutations, rapalogs of rapamycin that do not inhibit cellular mTOR kinase activity can also be used to induce infection of any cell type upon administration of a rapalog. These viruses can be induced to infect any cell type via multiple retargeting ligands upon rap treatment.

Cancer continues to be an intractable disease without safe and reliably effective treatments. In the last century, Applicants' knowledge about the origins of cancer and cancer biology has greatly advanced. However, despite Applicants' new understanding of cancer as a genetic disease, the standard of care for non-resectable disseminated disease remains genotoxic therapies, such as chemotherapy and irradiation, which often have intolerable and toxic side-effects. While drugs have been developed to target oncogenic proteins, Applicants have nothing to treat the genetic loss of tumor-suppressors. One approach to treat these cancers is oncolytic viral cancer therapy (FIG. 1) (Pesonen, S. et al., *Molecular Pharmaceutics*, 8(1): p. 12-28 (2010)).

Figure 2:
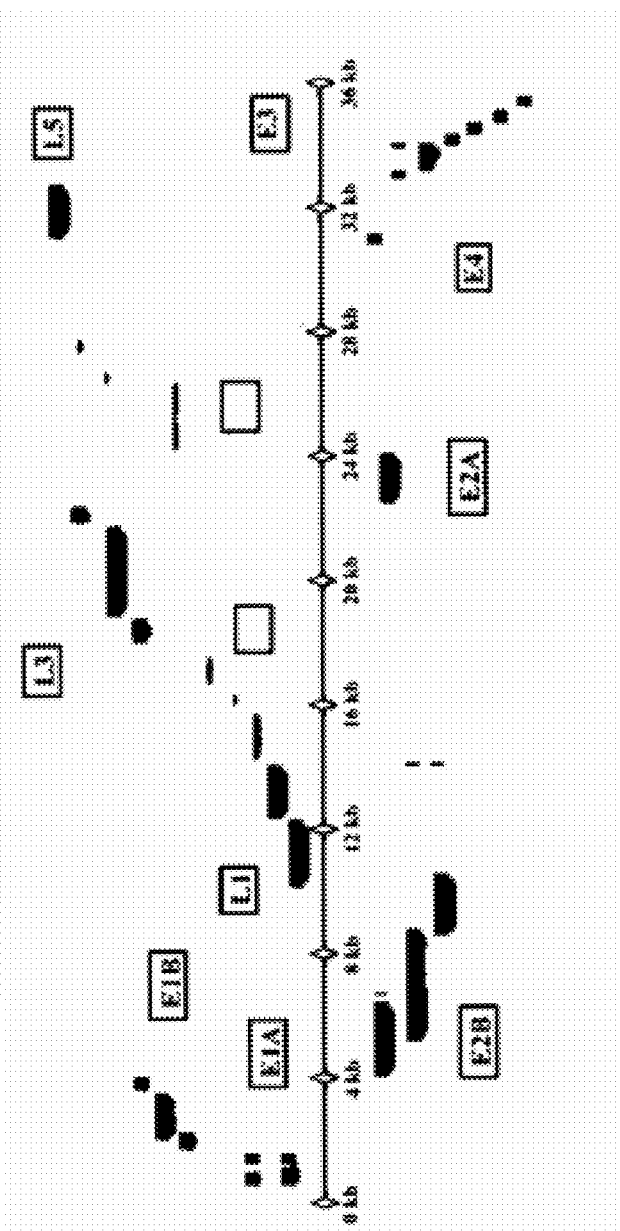
FIG. 2. Structural features of adenovirus and a map of the adenovirus genome with transcriptional units in boxes and labeled genes.
Figure 2:
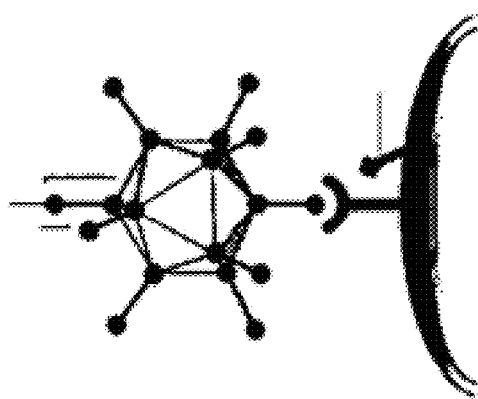
Figure 3A:
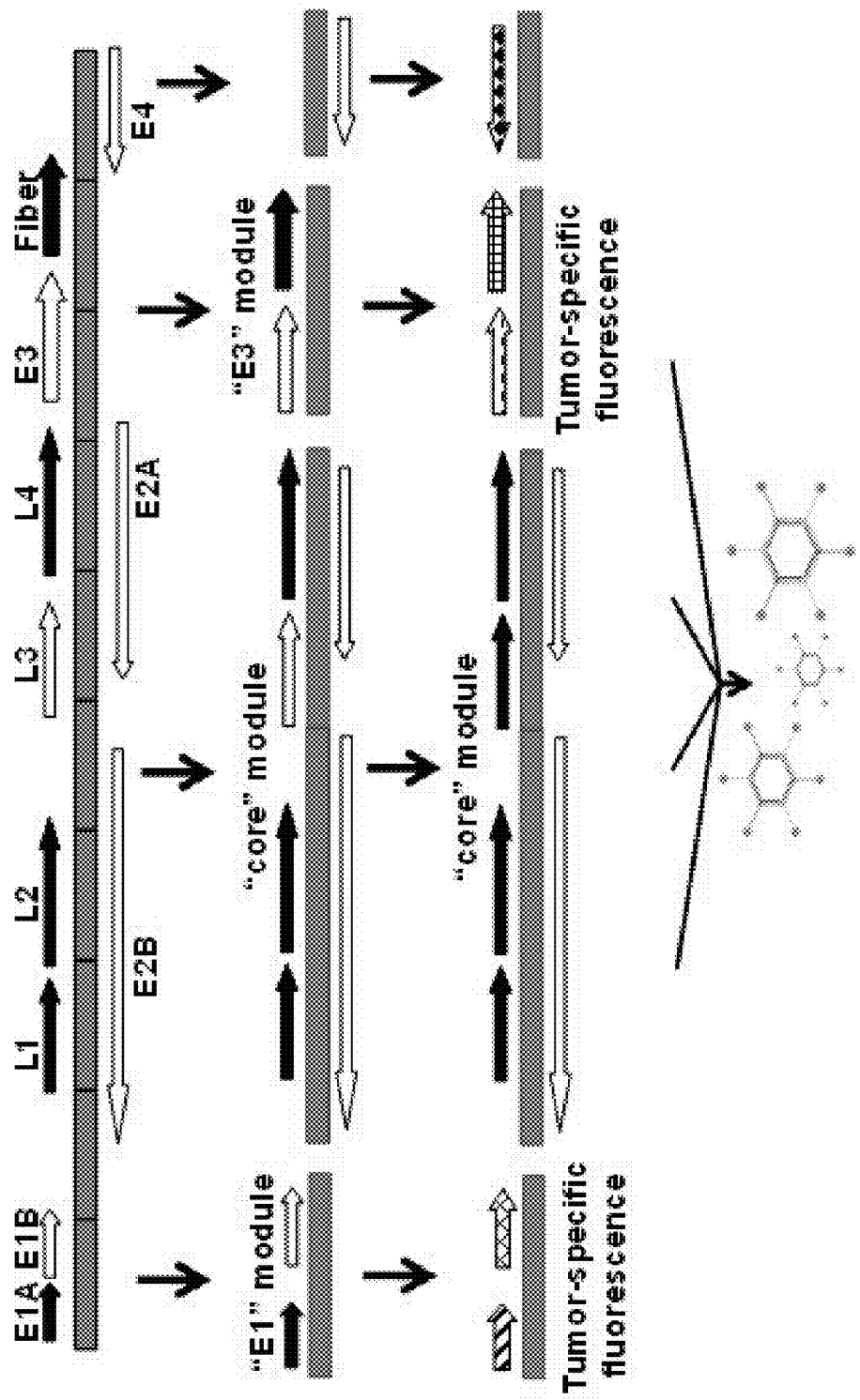
FIGS. 3A-3B. Outline of the Adsembly and Ad-SlicR adenovirus genome manipulation strategies developed by Applicants.
Figure 3B:
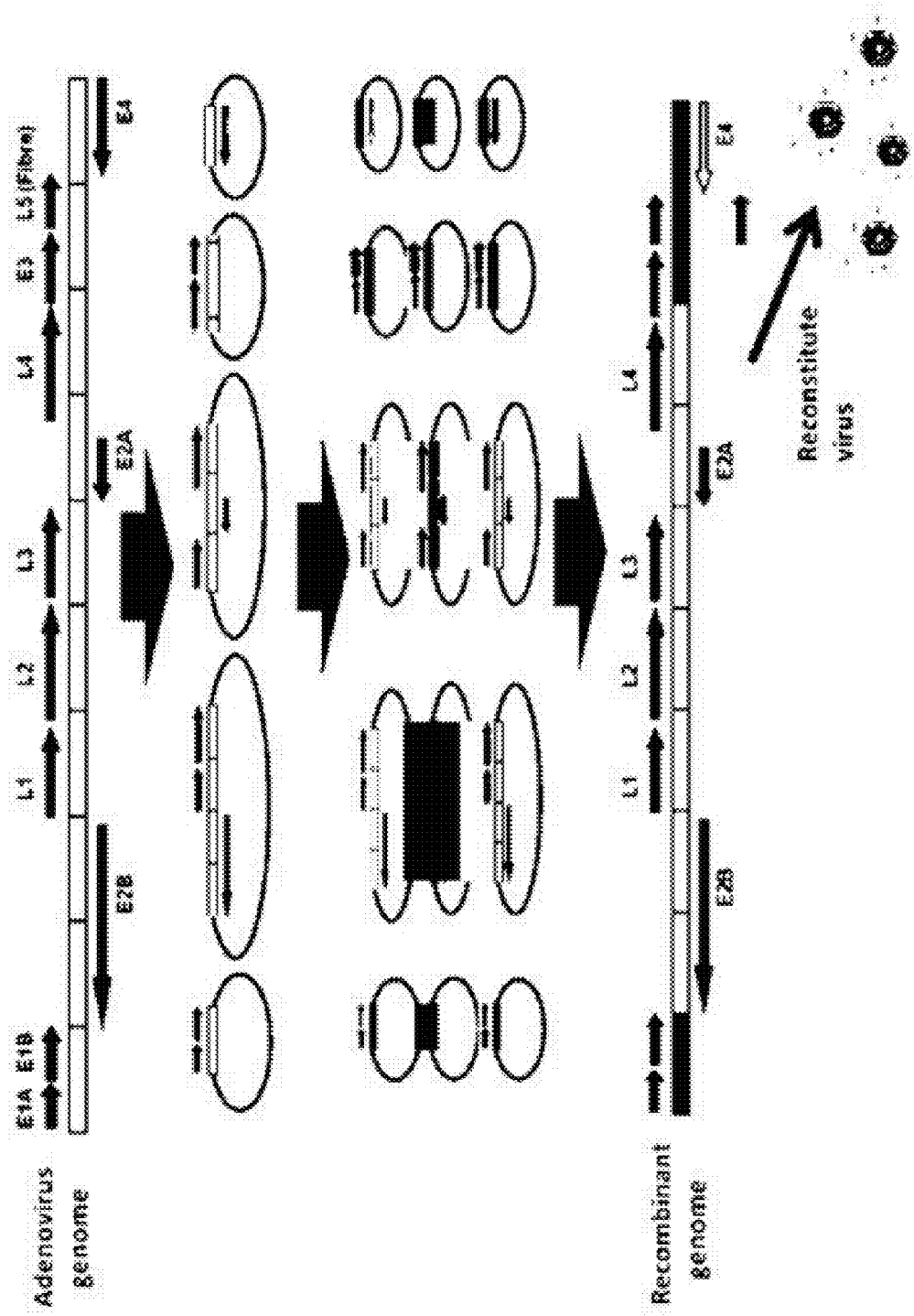
Figure 4:
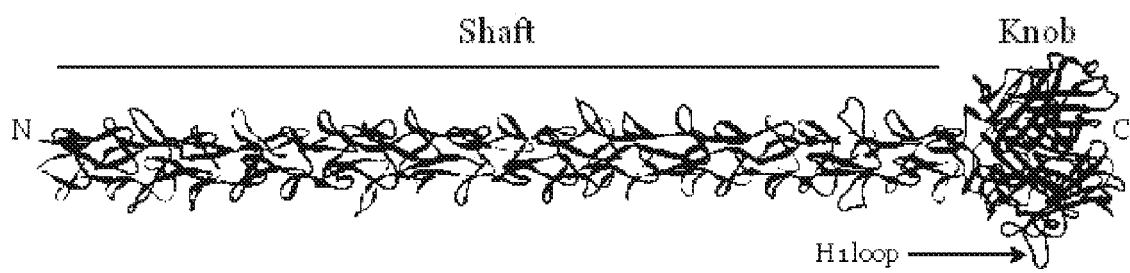
FIG. 4. Ribbon representation of the adenovirus fiber protein trimer. The N terminus (left) is bound to the surface of the capsid, with the C-terminal knob domain farthest away from the virus core. The flexible H1 loop the knob domain has been used for peptides insertions to impart new properties to fiber.

Adenovirus (Ad) has been studied for more than half a century, and has contributed significantly to Applicants' understanding of key mechanisms at the heart of mammalian cell biology such as splicing, critical growth regulatory hubs, transcription, and the cell cycle. Ad is a small double-stranded 36 kb DNA virus, sheathed in a protein capsid coat (FIG. 2). Ad particles primarily interact with host cells through protein interactions between the knob-domain of fiber on the surface of the capsid and a cell surface molecule (FIG. 2). Serotype 5 of adenovirus species C (Ad5) infects cells via fiber interactions with coxsackievirus and adenovirus receptor (CAR), primarily found at epithelial cell junctions Like all viruses, it is entirely dependent on host cells for its propagation. After depositing its genome into the host cell nucleus, a program is coordinated by virus proteins to activate the cell cycle in quiescent cells in order to replicate virus DNA. At the end of the Ad5 life cycle, after progeny virions have been assembled in the cell nucleus, the membranes of the cell are lysed, releasing the next generation of viruses.

Manipulating Adenovirus Tropism

Ad5 infection is mostly limited to cells that have CAR, which is expressed along with cadherin at epithelial cell tight junctions (Tomko, R. P. et al., *Proceedings of the National Academy of Sciences*, 94(7): p. 3352-3356 (2009); Bergelson, J. M., et al., *Science*, 275(5304): p. 1320-1323 (1997)). Unfortunately, it is metastases that kill most cancer patients, in which an epithelial to mesenchymal transition (EMT) results in downregulation of cadherin and CAR, instigating invasion and spread to distant sites (Anders, M., et al., *Br J Cancer*, 100(2): p. 352-9 (2009)). Thus, many malignant cells do not express CAR and are not susceptible to infection by Ad5 (Anders, M., et al., *Br J Cancer*, 100(2): p. 352-9 (2009); Dietel, M., et al., *Journal of Molecular Medicine*, 89(6): p. 621-630 (2011); Matsumoto, K., et al., *Urology*, 66(2): p. 441-446 (2005)). A number of approaches have been taken to retarget Ad5 to different cellular receptors, including: chemical modification of purified adenovirus particles and infection with recombinant divalent "bridging" proteins to form complexes between fiber and receptor (reviewed in (Rein, D. T., M. Breidenbach, and D. T. Curiel, *Future Oncology*, 2(1): p. 137-143 (2006))). The disadvantage of these approaches is the restriction to the first round of infection, since following virus replication the chemical/recombinant targeting moiety is lost. This drawback can be overcome by directly modifying the fiber gene to encode targeting sequences, however this approach is not systematic because Applicants cannot predict the folding of de novo sequences and the correct assembly with virus particles. To date, this approach has only been useful for the insertion of small peptides.

Adsembly and AdSLIC are Enabling Technologies to Systematically Design New Optimized Adenoviruses from Libraries of Genomic Building Blocks and Heterologous Parts The potential of adenoviral vectors in several applications is hindered by the ability to engineer and combine multiple genetic modifications rapidly and systematically. To systematically re-design adenovirus as an oncolytic agent, Tools are needed to enable precise modification of its components. The 36 kb Ad5 genome is difficult to manipulate due to its size and abundance of restriction enzyme recognition (RER) sites. To date, a majority of recombinant Ads have been limited to the backbones that were digested and selected for fewer RER sites in the 1980s, and continue to remain due to the legacy of shuttle vectors. These backbones have accumulated a number of mutations distant from wild type sequences. Traditional cloning techniques with complex sequences are still time consuming and not systematic.

To overcome the limitations of Ad5 and current methodologies, Applicants have developed two new technologies, named 'Adsembly' and 'AdSlicR', which enable the rapid de novo assembly of adenoviral genomes in vitro from genomic component parts and heterologous elements in a single hour. Using a bioinformatics approach, Applicants split the adenoviral genome (36 kb) into 5 units, based on evolutionarily conserved sequences between species, transcriptional and functional modules. Each of these 5 units comprise compatible sections of a genomic building "parts library", the functions and diversity of which can be altered by engineering mutations or heterologous elements and further expanded by adding equivalent units from disparate adenovirus serotypes, mutants and species. In order to create a new adenovirus with unique properties, one of each of the units is selected from the library and rapidly reassembled into a complete genome in vitro using Adsembly or Ad-SlicR. Adsembly can be used to assemble a novel genome (in 1 hour) via multi-site specific recombination, which upon transfection, self-excises from a plasmid backbone and replicates to produce novel viruses. Ad-SlicR, which utilizes the same library genome building blocks, is a complementary strategy to erase inserted recombination sequences for more potent viral replication (if necessary) and clinical use. The ease of manipulation of multiple genomic fragments as small modular plasmid units and the systematic approach of these technologies now allows for rapid and precise construction of novel adenoviruses.

Adenovirus Targeting: A Genetically Encoded Switch

Oncolytic viral therapy has the potential to destroy a tumor mass of unlimited size, but only if the virus crosses the tumor vasculature and infection spreads from one cell to another. The fiber of Ad5 recognizes the epithelial cell junction molecule CAR (Tomko, R. P. et al., *Proceedings of the National Academy of Sciences*, 94(7): p. 3352-3356 (2009); Bergelson, J. M., et al., *Science*, 275(5304): p. 1320-1323 (1997)), which is expressed in variable levels on tumors (Rein, D. T., M. Breidenbach, and D. T. Curiel, *Future Oncology*, 2(1): p. 137-143 (2006); Dmitriev, I., et al., *J. Virol.*, 72(12): p. 9706-9713 (1998); Bauerschmitz, G. J., S. D. Barker, and A. Hemminki, *Int J Oncol*, 21(6): p. 1161-74 (2002); Breidenbach, M., et al., *Hum Gene Ther.*, 15(5): p. 509-18 (2004); Cripe, T. P., et al., *Cancer Res*, 61(7): p. 2953-60 (2001); Fechner, H., et al., *Gene Ther*, 7(22): p. 1954-68 (2000); Hemmi, S., et al., *Hum Gene Ther*, 9(16): p. 2363-73 (1998); Hemminki, A. and R. D. Alvarez, *BioDrugs*, 16(2): p. 77-87 (2002); Kanerva, A., et al., *Clin Cancer Res*, 8(1): p. 275-80 (2002); Li, Y., et al., *Cancer Res*, 59(2): p. 325-30 (1999); Miller, C. R., et al., *Cancer Res*, 58(24): p. 5738-48 (1998); Rein, D. T., et al., *Int J Cancer*, 111(5): p. 698-704 (2004)) and the loss of which is associated with increased metastasis (Anders, M., et al., *Br J Cancer*, 100(2): p. 352-9 (2009); Dietel, M., et al., *Journal of Molecular Medicine*, 89(6): p. 621-630 (2011); Matsumoto, K., et al., *Urology*, 66(2): p. 441-446 (2005)). Ad5 is not a naturally blood-borne virus and does not actively target and cross the vasculature. Both of these factors limit the potential of adenoviral vectors for gene expression and therapy.

Figure 6:
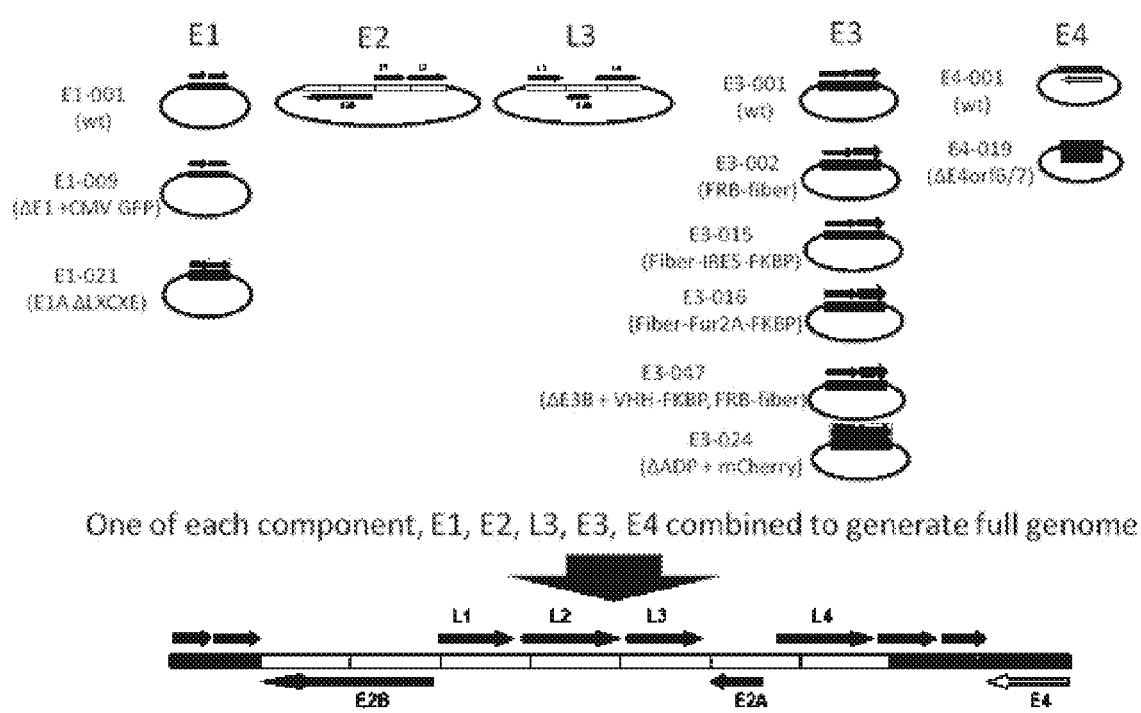
FIG. 6. Genome assembly strategy utilizing the building and combination of components to systematically create combination mutations in novel adenoviruses.

Attempts to retarget adenoviral uptake include the use of chemical adapters that link viral capsids to retargeting ligands. One example is fiber biotinylation to provide a chemical linker for high affinity binding to avidin-retargeting ligands (Liu, Y., P. Valadon, and J. Schnitzer, *Virology Journal*, 7(1): p. 316 (2010)). However, retargeting is only achieved with exogenous virus, since the chemical modifications are lost upon viral replication. Genetically encoding retargeting adapter fusions to viral coat proteins is desirable, but also more challenging. Unfortunately, the incorporation of large ligands in capsid proteins disrupts their folding/assembly (Belousova, N., et al., *J. Virol.*, 76(17): p. 8621-8631 (2002)). To avoid misfolding, smaller polypeptides can be inserted into the fiber H1 loop (FIG. 6) (Belousova, N., et al., *J Virol*, 76(17): p. 8621-31 (2002)). For example, RGD peptides enhance integrin-assisted uptake, but are not sufficient to alter viral tropism. Fiber fusions to single chain antibodies (scFVs) are attractive as well, but the former require processing in the ER/cytosol while fiber assembles in the nucleus (Kontermann, R. E., *Curr Opin Mol Ther*, 12(2): p. 176-83 (2010)). Thus, despite ongoing efforts to retarget infection, in vivo studies and gains have been disappointing (Waehler, R., S. J. Russell, and D. T. Curiel, *Nat Rev Genet*, 8(8): p. 573-87 (2007)).

An ideal virus would cross the blood/endothelium layer and infect tumor cells via disparate receptors. The ideal system would be a genetically encoded chemical adapter that could be used to switch viral tropism within the body via any multiple retargeting moieties, without compromising viral replication and safety. Provided herein is a novel, inducible, genetically encoded chemical adapter system that retargets infection to multiple cell types, and is not lost upon viral replication. The present invention therefore overcomes the limitations of prior approaches and has several advantages. Any unanticipated toxicities associated with receptor-retargeting can be stopped by drug withdrawal. In addition, multiple retargeting ligands can be expressed within a single virus to target tumor cell receptors (e.g. EGFR) and the vasculature (e.g. Von Willebrand factor/transferrin).

Figure 7A:
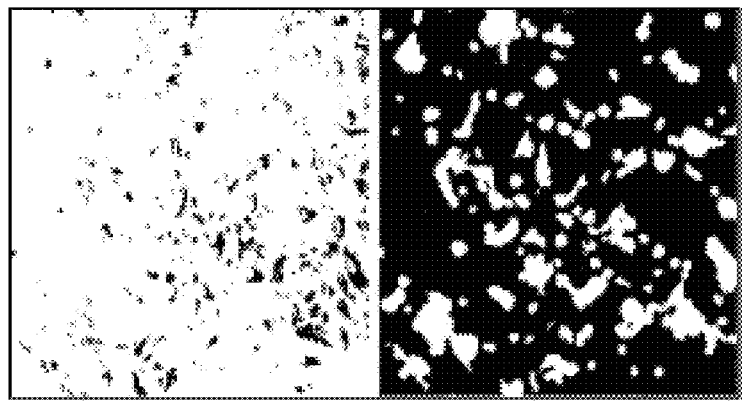
FIGS. 7A-7B. Ad 122 is a viable adenovirus expressing fiber with the FRB insertion. Ad-122 is a viable adenovirus expressing fiber with the FRB insertion.
Figure 7B:
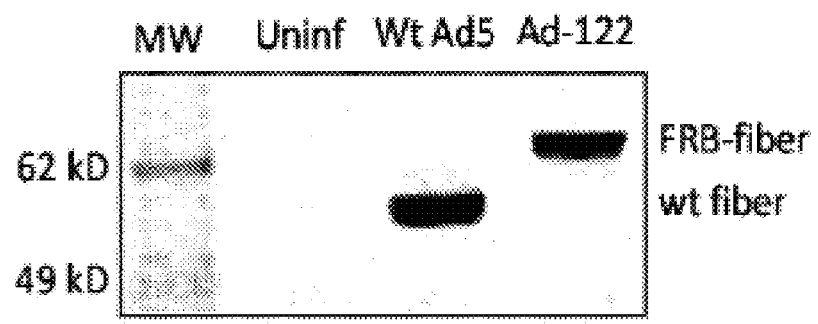

Applicants retargeted the adenovirus viral coat protein fiber to alternate cellular receptors using a known property of the immunosuppressive and anti-tumor drug rapamycin (rap; FIG. 7). Rapamycin can be used to induce heterodimers of heterologous proteins if one is fused to FKBP domains (e.g. a retargeting ligand) and the other (e.g. fiber) to the FRB domain of mTOR (Chen, J., et al., *Proc Natl Acad Sci USA*, 92(11): p. 4947-51 (1995)). Upon treatment with rap, fiber will heterodimerize with the retargeting ligand enabling the virus to infect the cell type of choice. Rapamycin is a macrolide antibiotic that is FDA approved and has ideal pharmacokinetic profiles in mammals. The high affinity and stability of rap-induced heterodimerization has been used with great success in several applications including phage display of receptor-ligand complexes (de Wildt, R. M., et al., *Proc Natl Acad Sci USA*, 99(13): p. 8530-5 (2002)), transcriptional activation and reconstitution of bi-functional proteins (Clackson, T., *Chem Biol Drug Des*, 67(6): p. 440-2 (2006)). A novel application of this system is provided, which also takes advantage of Applicants' previous studies of rap as a rational combination with oncolytic viruses (O'Shea, C., et al., *Embo J*, 24(6): p. 1211-21 (2005)).

Develop a Genetically Encoded Small Molecule-Controlled System for Retargeting Adenovirus to Tumor Cell Receptors The reliance of current adenoviral vectors on a single cellular receptor for their uptake limits their therapeutic potential via systemic delivery. To overcome this problem, Applicants designed novel Ads with the rapamycin-induced, genetically encoded FRB/FKBP heterodimer to enable retargeting of adenovirus to tumor cell receptors. Ultimately, this system enables targeting of receptors in angiogenic tumor vasculature to eliminate aggressive tumors (e.g. TEMs, TVMs), and upregulated markers in high-risk tumors such as breast cancer (e.g. EGFR, HER2, TfR).

Insertion of FRB Domain into Fiber H1 Loop

Figure 5:
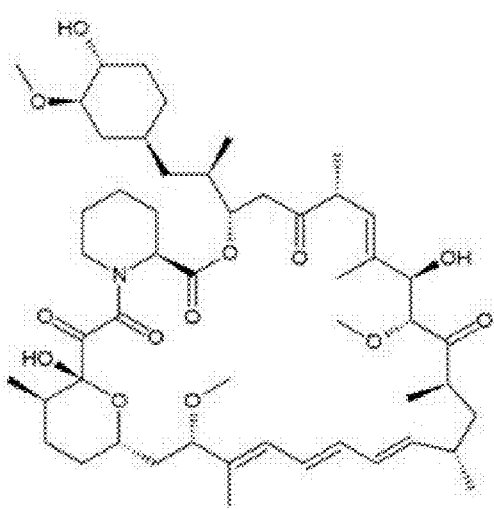
FIG. 5. Structure of immunosuppressive anti-tumor drug and antibiotic rapamycin and rapalog AP21967.
Figure 5:
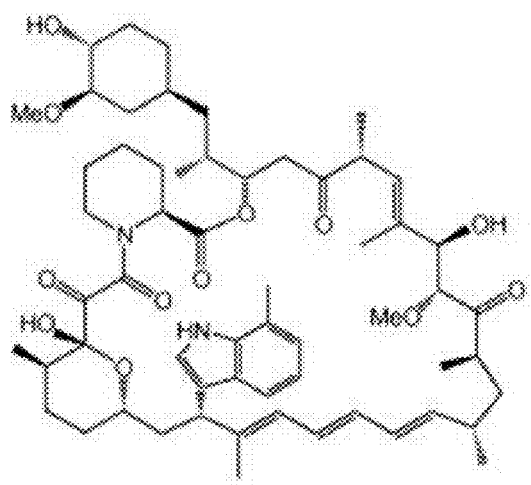

The fiber protein which infers tropism to adenovirus is generally not permissible to large insertions or modifications, because the correct folding and assembly of fiber trimers into adenovirus particles are critical for viable progeny. To date, insertion of sequences in the C-terminal Ad5 fiber knob-domain has been effectively limited to peptides (Belousova, N., et al., *J. Virol.*, 76(17): p. 8621-8631 (2002)). Using Adsembly (described in FIG. 5) the 90 amino acid FRB domain was inserted into the flexible H1 loop of fiber, which accommodates insertions of up to 100 amino acids without deleterious effects (Belousova, N., et al., *J. Virol.*, 76(17): p. 8621-8631 (2002)).

Experimental Approach

Figure 9:
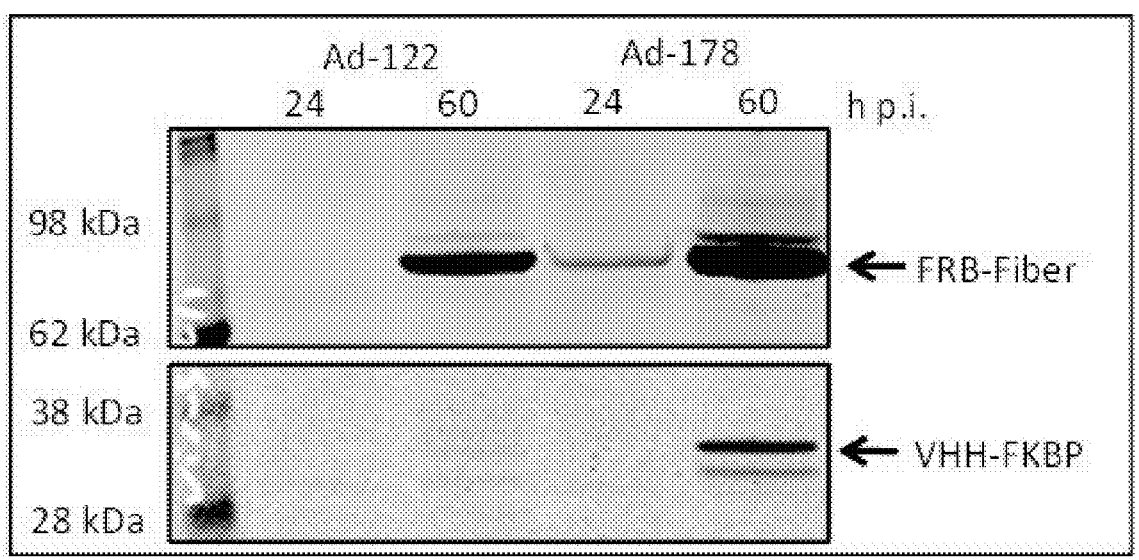
FIG. 9. AD-178 expresses FKBP during infection. Lysates collected from infected 293 E4 cells 24 and 60 h p.i. and probed with anti-fiber (top panel of FIG. 9) and anti-FKBP antibody ab2918 (Abcam; bottom panel of FIG. 9).

The wild type E3 component plasmid, $E_{3\text{-}001}$, (Table 1) from the genome parts library which Applicants designed was used as the template for insertion of the FRB sequence into the fiber gene. $E_{3\text{-}001}$ was PCR amplified to generate a product with SLIC-compatible ends for insertion between fiber Thr546 and Pro567. The 90 aa FRB domain of mTOR (Glu2025-Gln2114) was PCR amplified from mTOR cDNA and combined via SLIC to generate E3-002 (FIG. 8). Wild-type E2, L3, and E4 components were combined with E3-002 and E1-009 (containing a CMV-driven GFP gene) using the Adsembly strategy to generate the Ad-122 genome (FIG. 8). Applicants transfected the Ad-122 genome into 293 E4 cells, and harvested virus. Unlike the insertion of many large ligands such as TfR, FRB did not inhibit viral replication or assembly and robust infection as evidenced by GFP fluorescence from the E1 reporter and observed cytopathic effect (CPE). I confirmed expression of FRB-fiber by Western blot as indicated by predicted migration of FRB-fiber (72.4 kDa) versus wt fiber (61.6 kDa; FIG. 9).

Expression of FKBP Retargeting Moieties from Adenovirus Genome

The expression of FKBP from the virus genome would ideally have similar timing and levels matching that of fiber, to enable efficient dimerization with fiber in the presence of rap. Applicants adopted several strategies to express FKBP from the genome as summarized in FIG. 10.

Experimental Approach

Figures 10A, 10B:
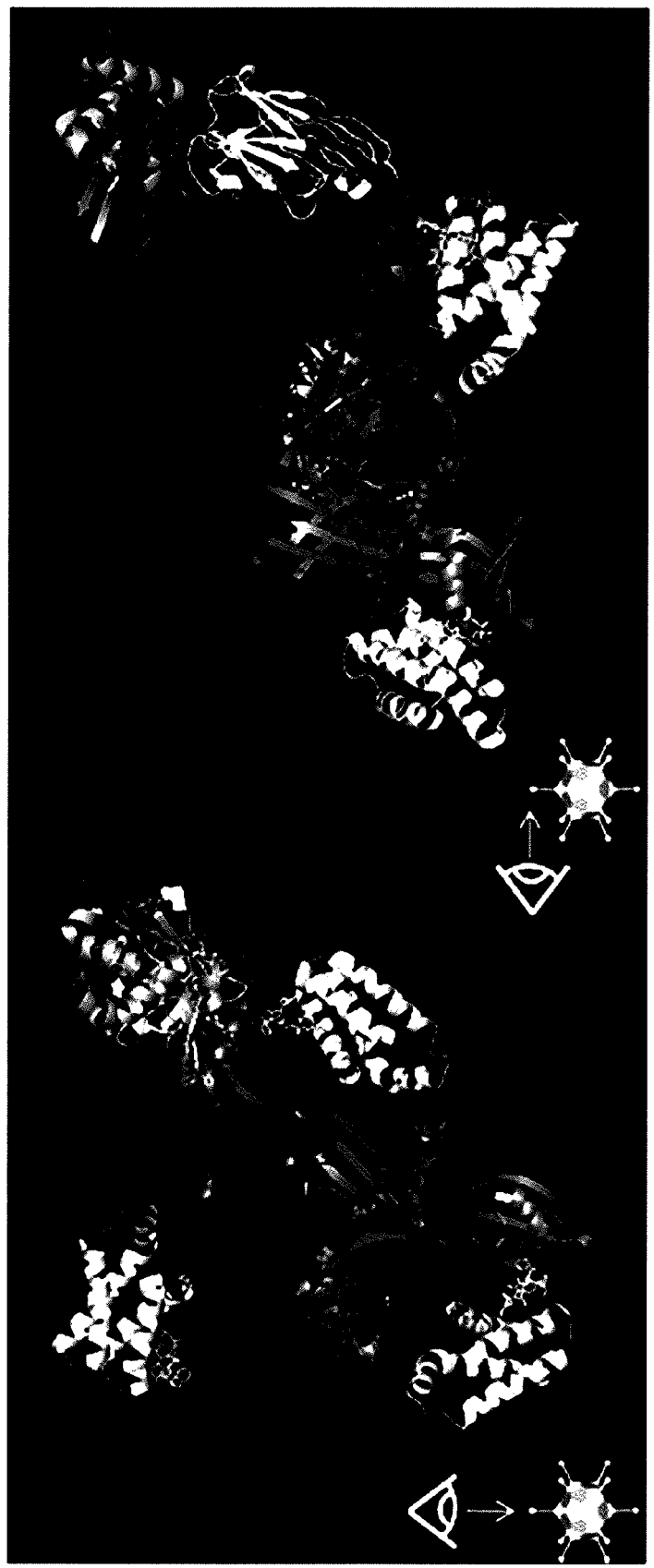
FIGS. 10A-10B. Ribbon model of FRB-fiber knob-domain in complex with rapamycin/VHH-FKBP and VHH target. Ad5 knob trimer (PDB ID 1KNB) with FRB domain in complex with FKBP (PDB ID 1NSG) as a C-terminal fusion of VHH, binding its target (PDB ID 3EBA).

The E3-002 plasmid, carrying the FRB insertion in fiber, was used as the template to introduce the sequences necessary for the strategies summarized in FIG. 10. The first approach was to express FKBP from the adenovirus genome by co-translationally expressing it from the fiber transcript (FIG. 10C). The FKBP sequence was placed downstream of the fiber coding sequence following an inserted Furin-2a sequence. The Furin-2a sequence is an optimized Furin protease recognition site followed by the foot-and-mouth disease virus 2a auto-cleavage site (Fang, J., et al., *Mol Ther*, 15(6): p. 1153-1159 (2007)). It should generate two distinct polypeptides in equimolar amount; the FRB-Fiber molecule with a residual arginine on its C-terminus, and the FKBP protein with residual proline on its N-terminus.

Figure 11:
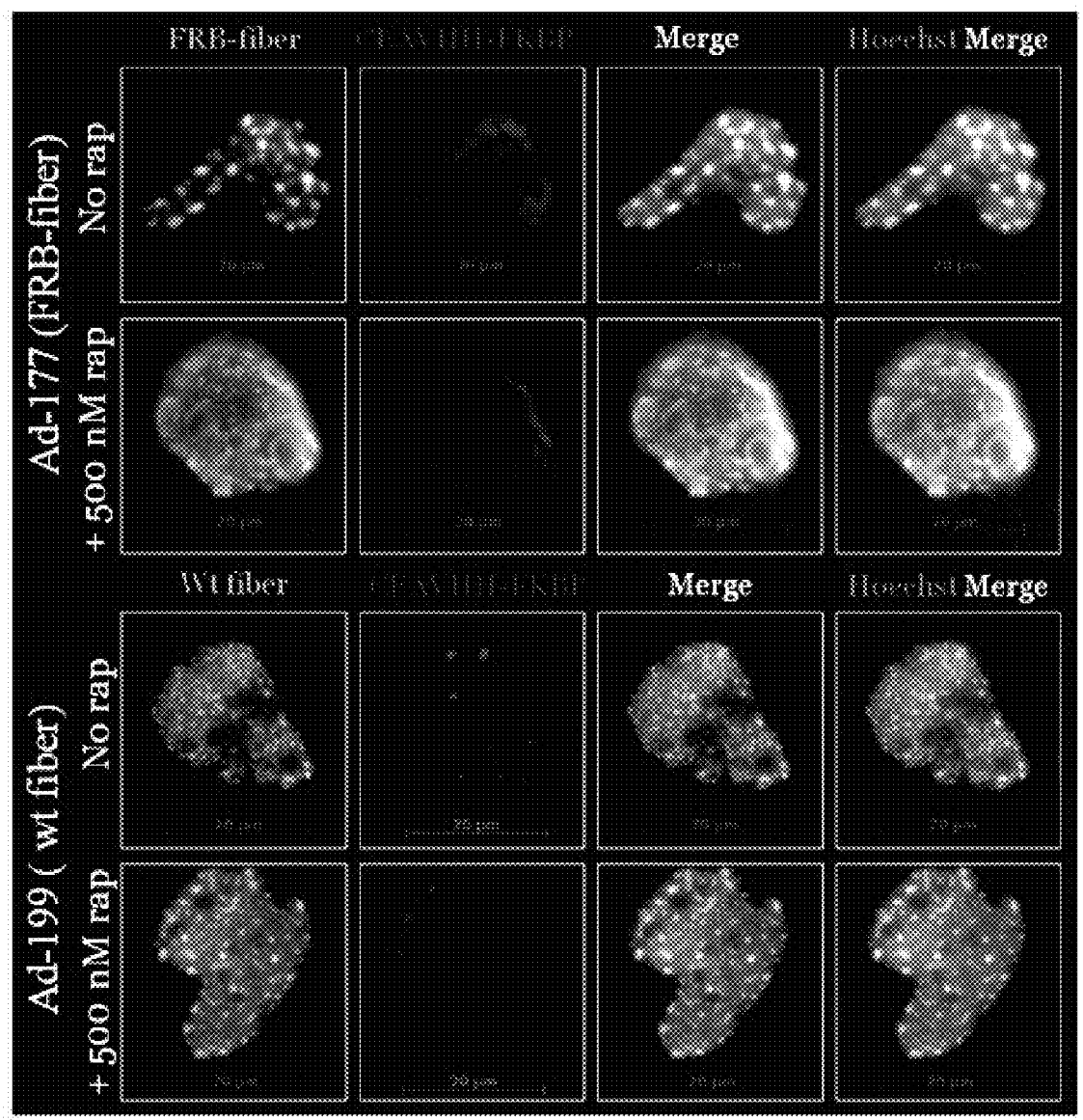
FIG. 11. Immunofluorescence to detect fiber and CEAVHH-FKBP localization in infected 293 E4 cells. 293 E4 cells infected with either Ad-177 (CEAVHH-FKBP, FRB-fiber) or Ad-199 (CEAVHH-FKBP, wt fiber) and 500 nM rap or solvent only (EtOH) added 30 h p.i. Cells fixed at 36 h and stained with anti-fiber antibody 4D2 or anti-FBKP antibody ab2918 (Abcam).
Figure 12:
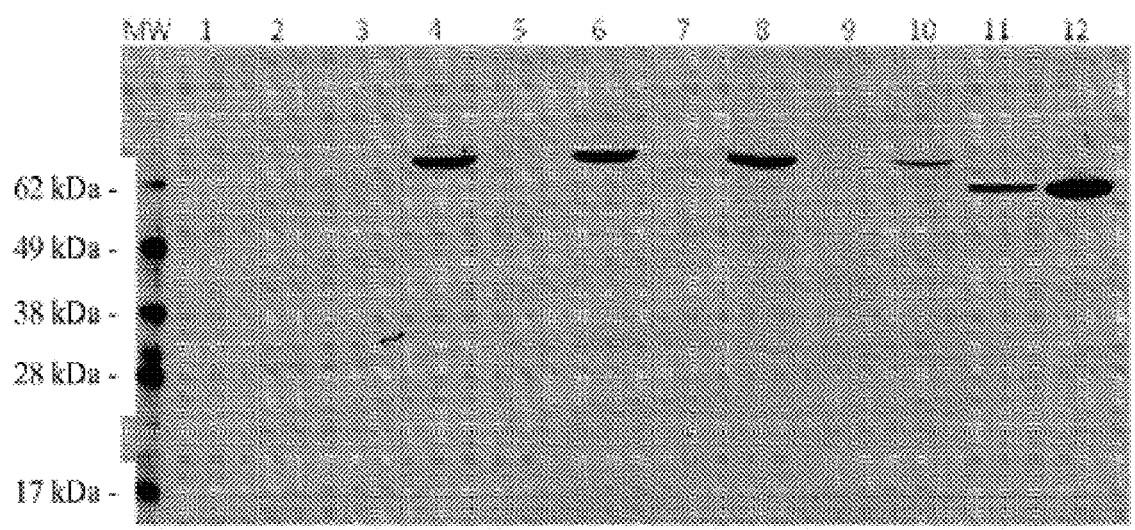
FIG. 12. FKBP fusion protein does not detectibly accumulate when controlled by 5' IRES on fiber gene. 293 E4 cells infected with recombinant adenoviruses. Cells harvested, and soluble proteins probed for fiber and FKBP expression by immunoblot. Top panel: FRB-fiber accumulates during infection. Bottom panel: VHH-FKBP (~32 kDa) is not detectible.
Figure 12:
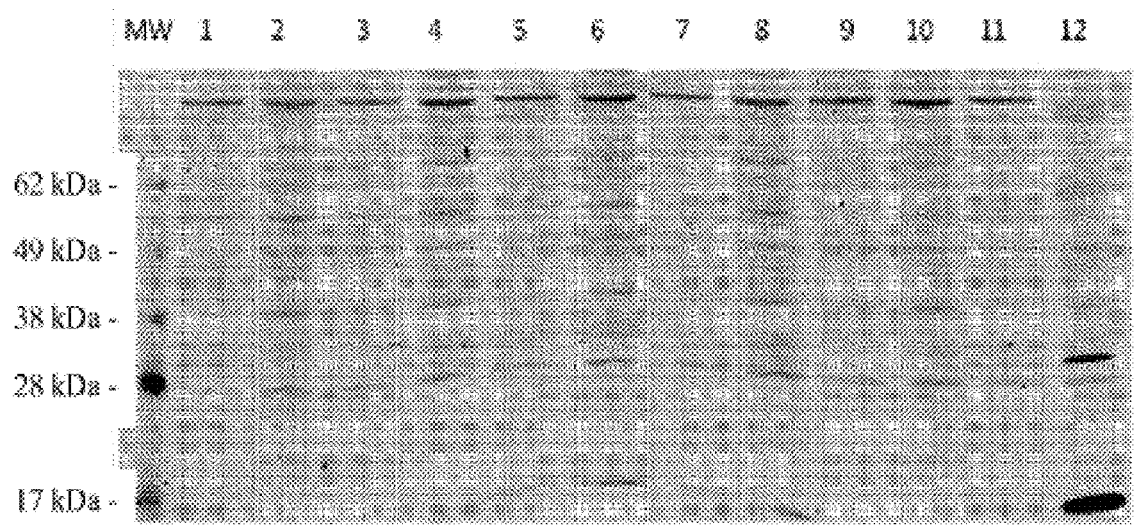

The sequence was cloned successfully, generating E3-016, and used the Adsembly strategy to create a full length genome with E1-009, E3-016 and wild type E2, L3, and E4. Similar to the preparation of Ad-122, the isolated supernatant was applied to 293 E4 cells, but there was no productive viral replication indicated by either fluorescence or CPE. Therefore, an alternative approach was used to express FKBP using an IRES element inserted on the 3' end of the fiber gene before the polyA sequence used for the fiber transcript (FIG. 10D). The E3 component (E3-015) was cloned successfully, and generated a complete genome using E1-009, E3-015 and wildtype E2, L3, and E4 (FIG. 8). This virus was able to replicate in 293 E4 cells, however no FKBP expression could be detected by Western blot as late as 60 h p.i., indicating that the efficiency of an IRES on the fiber transcript is not ideal to express FKBP. The final approach was to utilize adenovirus transcriptional architecture to express FKBP. Since the genes in the E3 transcription unit of adenovirus are dispensable for virus replication in cell culture, the sequence on the E3B transcript encoding RIDα, RIDβ, and 14.7k was replaced with FKBP. The E3 component (E3-048) was cloned and used Adsembly with E1-009, wild type E2, L3, and E4 to generate Ad-178 (FIG. 8). This virus was able to replicate in 293 E4 cells, as evidenced by fluorescence and CPE. Western blot analysis of infected cell lysates revealed that the FKBP protein accumulated in infected 293 E4 cells (FIG. 11). Therefore, this strategy was used to create novel viruses that express FRB-fiber and FKBP retargeting moieties.

Targeting Moieties for Fusion to FKBP

Figure 13:
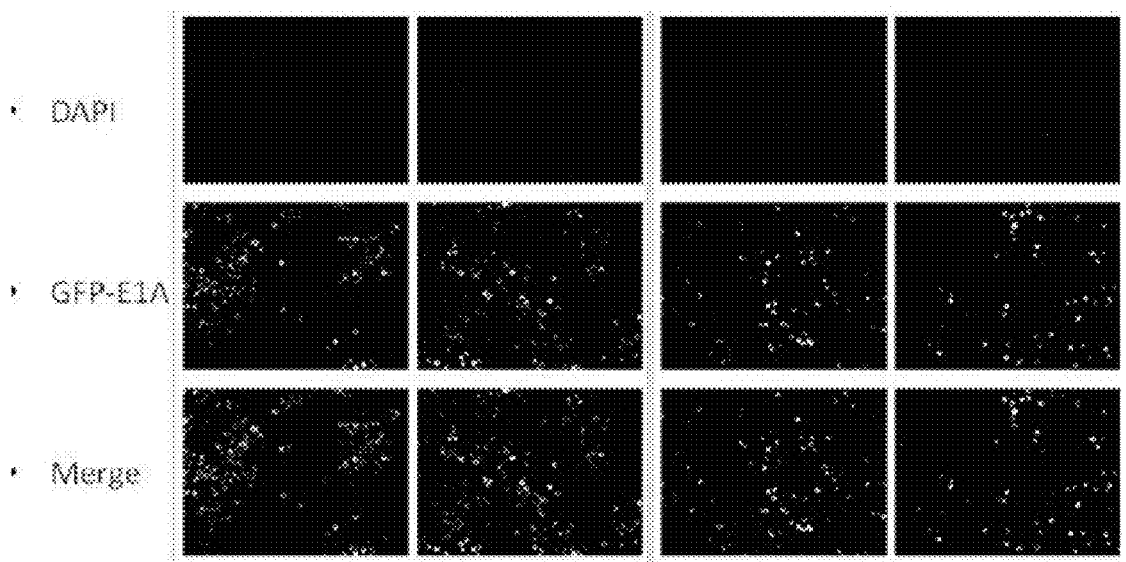
FIG. 13. Representative IMAGEXPRESS™ images of rapamycin-induced EGFR-retargeted Ad5 infection of MDA MB 468. Ad-178 expressing a GFP-reporter was prepared in the presence or absence of 500 nM rapamycin by infection of 293 E4 cells, and supernatant was used to infect MDA MB 468 in culture.

An ideal targeting protein for fusion to FKBP is a stable molecule with strong affinity for a specific cancer cell surface molecule. A number of approaches were explored including: BN peptide, EGF peptide, TGFα, anthrax toxin PA, Tf, F3 peptide, and VEGF (Table 3). As a proof of principle, VHHs, were first explored as described below. A similar experimental approach will be adapted for other retargeting moieties listed in Table 3. A class of proteins which best fits these criteria are the heavy chain domains (VHH) from single-domain antibodies (sdAbs). Camelids and sharks encode sdAbs which have specificity for their specific target from one variable chain domain, instead of the two (conventionally) that most other mammals have (e.g. rodents, humans) (Kontermann, R. E., *Curr Opin Mol Ther*, 12(2): p. 176-83 (2010)). Although small single-chain variable fragments (scFVs) have been more widely used, the smaller and more stable VHHs have the distinct advantage of not requiring post-translational disulfide bond formation to function. FKBP was fused to VHHs with specificity to cancer cell receptors to impart ideal adenovirus targeting. To demonstrate this effect with the rap-inducible retargeting system, recently identified VHHs with specificity to carcinoembryonic antigen-related cell adhesion molecule 5 (CEA also CEACAM5) (Vaneycken, I., et al., *Journal of Nuclear Medicine*, 51(7): p. 1099-1106 (2010); Behar, G., et al., *FEBS Journal*, 276(14): p. 3881-3893 (2009)), a biomarker for gastrointestinal, breast, lung and ovarian carcinomas (Duffy, M. J., *Clin Chem*, 47(4): p. 624-630 (2001)), and epidermal growth factor receptor (EGFR) (Gainkam, L. O., et al., *Journal of nuclear medicine: official publication, Society of Nuclear Medicine*, 49(5): p. 788-95 (2008)), upregulated in many cancers of epithelial origin such as breast, head and neck, prostate, lung, and skin are used. Based on the structural modeling (FIG. 13), the VHH domains (CEAVHH, EGFRVHH) are fused to the N terminus of FKBP for the least steric hindrance for VHH/target interactions and the FKBP/rap/FRB dimerization interface.

The gene sequences encoding CEAVHH and EGFRVHH were human codon optimized and synthesized by Blue Heron Biotechnologies based on protein sequences identified by Behar et al. and Roovers et al., respectively (Behar, G., et al., *FEBS Journal*, 276(14): p. 3881-3893 (2009); Roovers, R., et al., *Cancer Immunology*, Immunotherapy, 56(3): p. 303-317 (2007)). Using SLIC, the VHH sequences were fused to the N-terminus of FKBP with an inserted GSGSGST linker sequence. These fusion proteins were cloned into E3 components with the approach described in herein to generate Ad-177 and Ad-178 (Table 1). FIG. 11 shows the expression the EGFRVHH-FKBP fusion protein from the Ad-178 infected cells, which is similar to CEAVHH-FKBP expression from Ad-177 (data not shown). The gene sequence encoding PA domain 4 were human codon optimized and synthesized by Blue Heron Biotechnologies based on Uniprot accession P13423. Using SLIC, the PA domain 4 was fused to the N-terminus of FKBP with an inserted GSGSGST linker sequence. This fusion protein was cloned into an E3 component with the approach described in herein to generate Ad-281 (Table 1).

Figure 14:
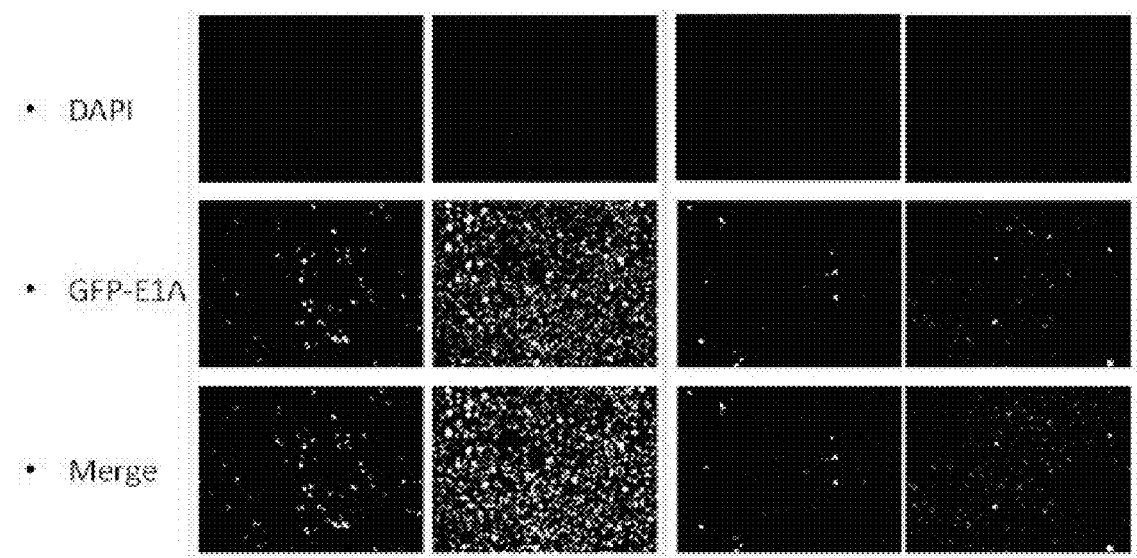
FIG. 14. Representative IMAGEXPRESS™ images of rapamycin-induced EGFR-retargeted Ad5 infection of MDA MB 453. Ad-178 expressing a GFP-reporter was prepared in the presence or absence of 500 nM rapamycin by infection of 293 E4 cells, and supernatant was used to infect MDA MB 453 in culture.
Figure 15:
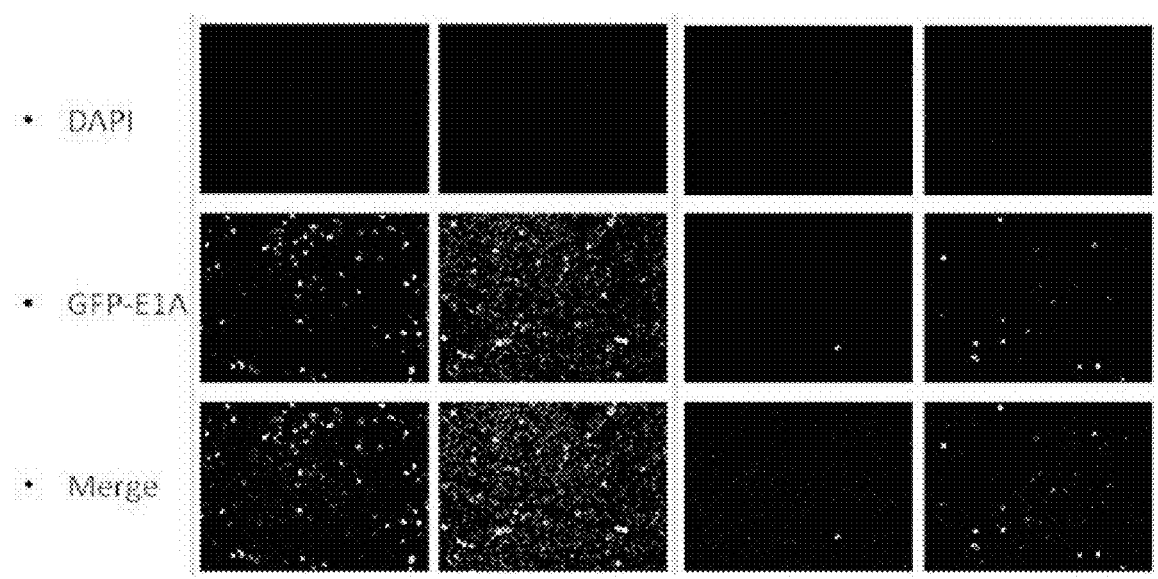
FIG. 15. Representative IMAGEXPRESS™ images of rapamycin-induced EGFR-retargeted Ad5 infection of MDA MB 231. Ad-178 expressing a GFP-reporter was prepared in the presence or absence of 500 nM rapamycin by infection of 293 E4 cells, and supernatant was used to infect MDA MB 231 in culture.
Figure 16:
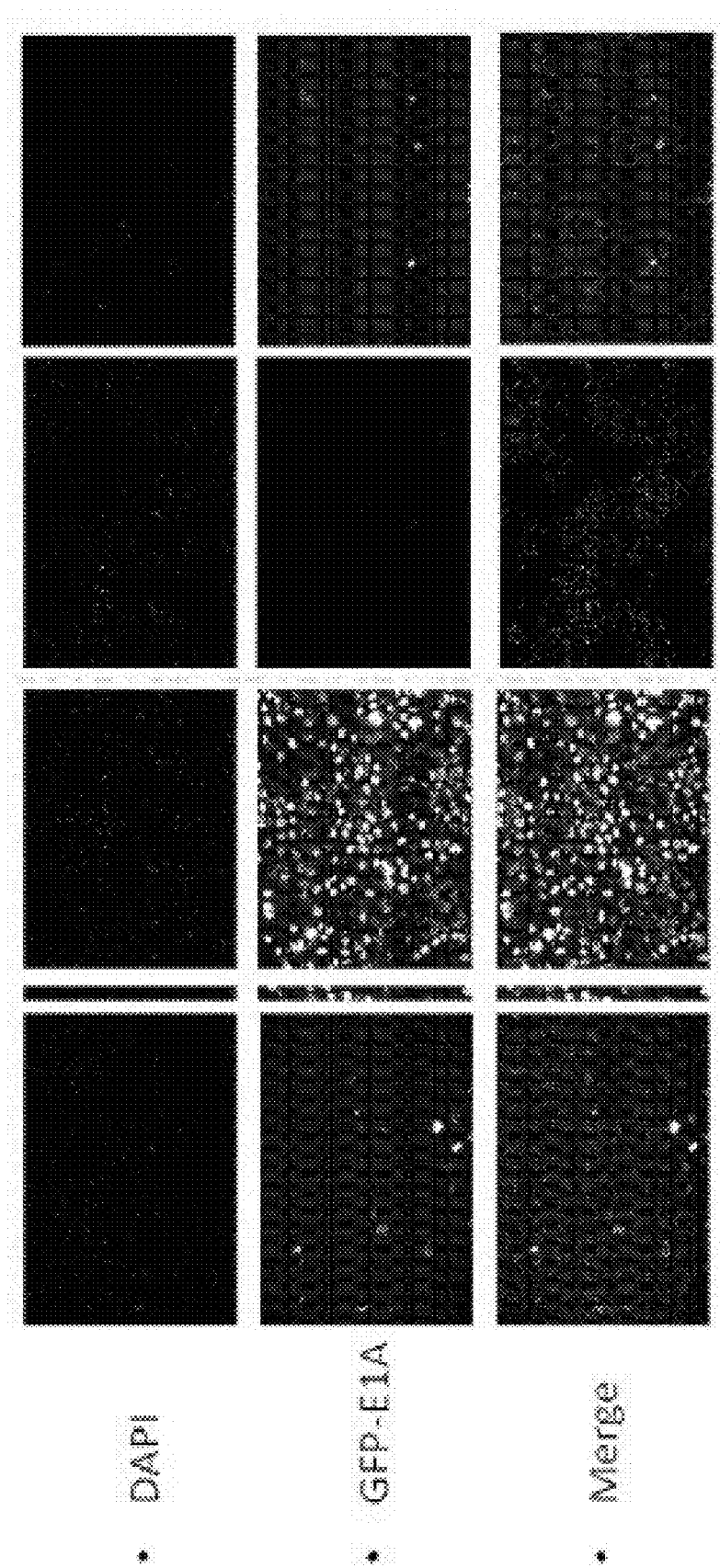
FIG. 16. Representative IMAGEXPRESS™ images of rapamycin-induced EGFR-retargeted Ad5 infection of HS578T. Ad-178 expressing a GFP-reporter was prepared in the presence or absence of 500 nM rapamycin by infection of 293 E4 cells, and supernatant was used to infect HS578T in culture.
Figure 17:
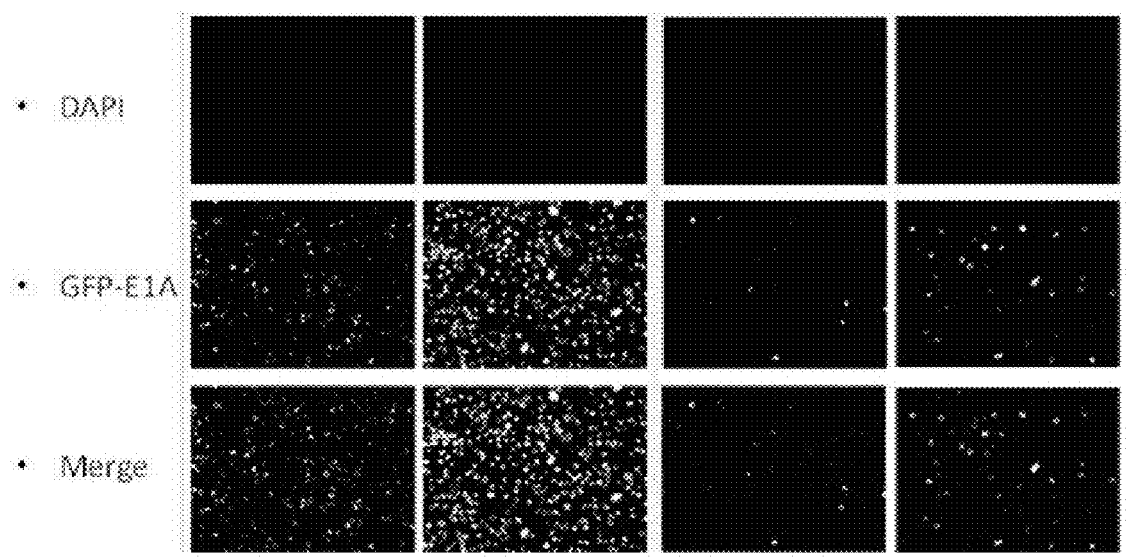
FIG. 17. Representative IMAGEXPRESS™ images of rapamycin-induced EGFR-retargeted Ad5 infection of U87. Ad-178 expressing a GFP-reporter was prepared in the presence or absence of 500 nM rapamycin by infection of 293 E4 cells, and supernatant was used to infect U87 in culture.
Figure 18:
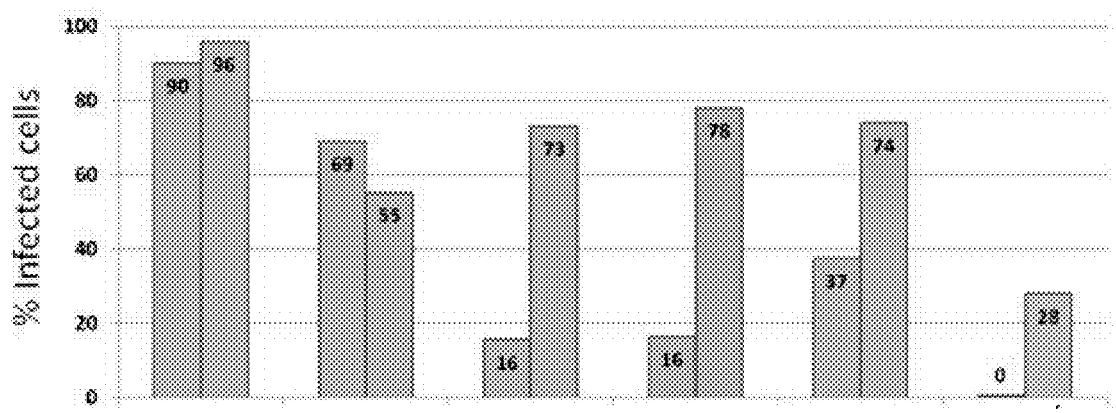
FIG. 18. Infection of a panel of breast cancer cell lines by rapamycin-induced EGFR-retargeted adenovirus. Ad-178 expressing a GFP-reporter was prepared in the presence or absence of 500 nM rapamycin by infection of 293 E4 cells, and supernatant was diluted 50-fold used to infect cells in culture. % infected cells determined 24 h p.i. by IMAGEXPRESS™ analysis of GFP positive nuclei. Each pair of columns in the histogram shows infection of a breast cancer cell line with Ad-178 expressing a GFP-reporter prepared in the absence (left column) or in the presence (right column) of rapamycin. The histogram shows from left to right infection of MDA MB468 cells (90% without rapamycin; 96% plus rapamycin), MDA MB415 cells (69% without rapamycin; 55% plus rapamycin), MDA MB453 (16% without rapamycin; 73% plus rapamycin), MDA MB231 (16% without rapamycin; 78% plus rapamycin), BTS49 (37% without rapamycin; 74% plus rapamycin), and HS578 (0% without rapamycin; 28% plus rapamycin), respectively.
Figure 19:
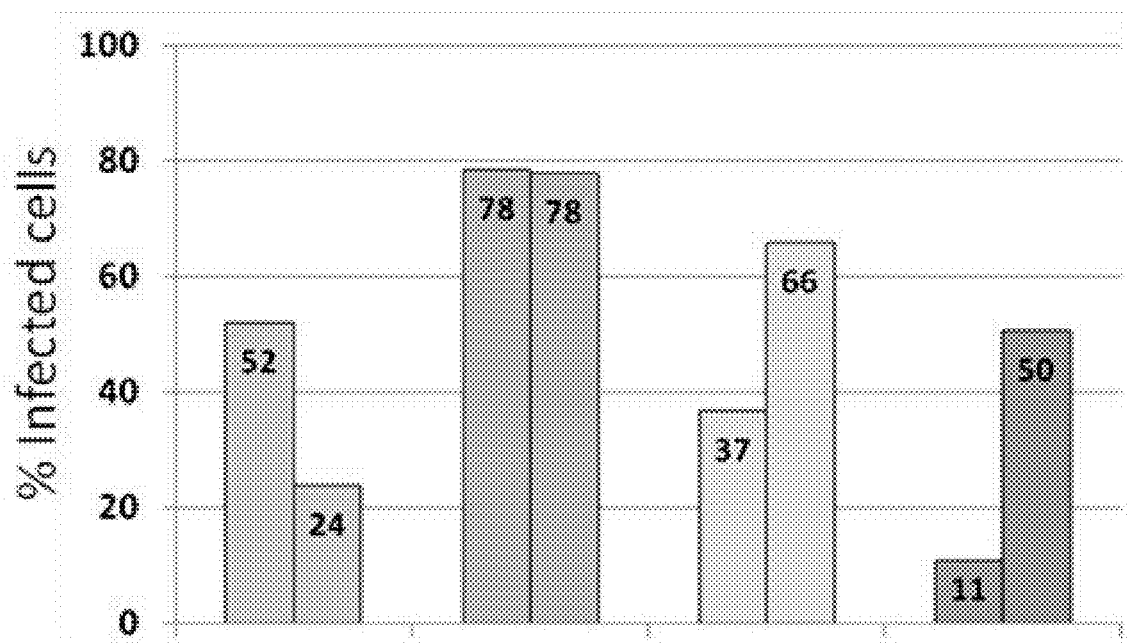
FIG. 19. Infection of a panel of cancer cell lines by rapamycin-induced EGFR-retargeted adenovirus. An Ad-178 expressing a GFP-reporter was prepared in the presence or absence of 500 nM rapamycin by infection of 293 E4 cells, and supernatant was diluted 50-fold used to infect different cancer cells in culture. % infected cells determined 24 h p.i. by IMAGEXPRESS™ analysis of GFP positive nuclei. Each pair of columns in the histogram shows infection of a cancer cell line with Ad-178 expressing a GFP-reporter prepared in the absence (left column) or in the presence (right column) of rapamycin. The histogram shows from left to right infection of U2OS osteosarcoma cell line (52% without rapamycin; 24% plus rapamycin), H1299 lung carcinoma cell line (78% without rapamycin; 78% plus rapamycin), A549 lung carcinoma cell line (37% without rapamycin; 66% plus rapamycin), and U87 glioblastoma cell line (11% without rapamycin; 50% plus rapamycin), respectively.
Figure 20:
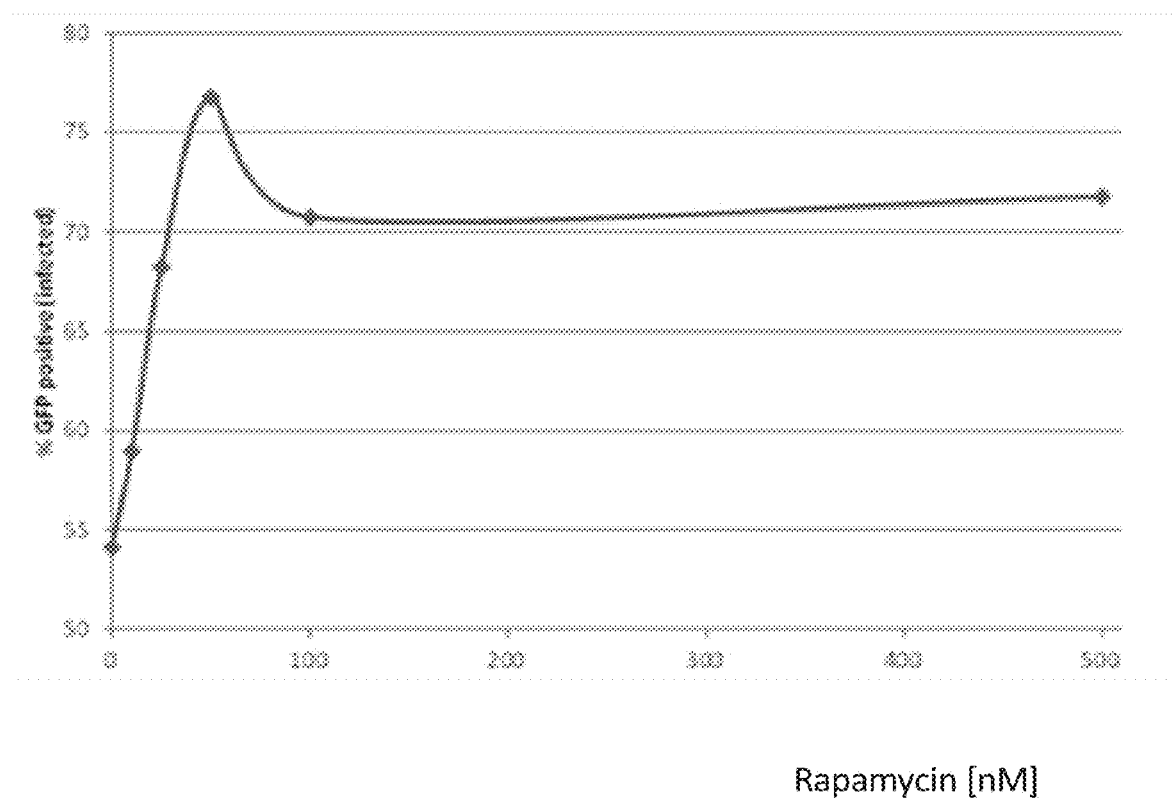
FIG. 20. Rapamycin concentration optimization for EGFR-retargeting with Ad-178 to infect MDA MB 453. Ad-178 expressing a GFP-reporter was prepared in the presence or absence of various rapamycin concentration during infection of 293 E4 cells, and supernatant was used to infect MDA MB 453 cells in culture. % infected cells determined 24 h p.i. by FACS analysis of GFP positive cells. Percent GFP positive cells were 54.13% at 0 nM rap, 58.96% at 10 nM rap, 68.23% at 25 nM rap, 76.75% at 50 nM rap, 70.73% at 100 nM rap, and 71.76% at 500 nM rap, respectively.
Figure 21A:
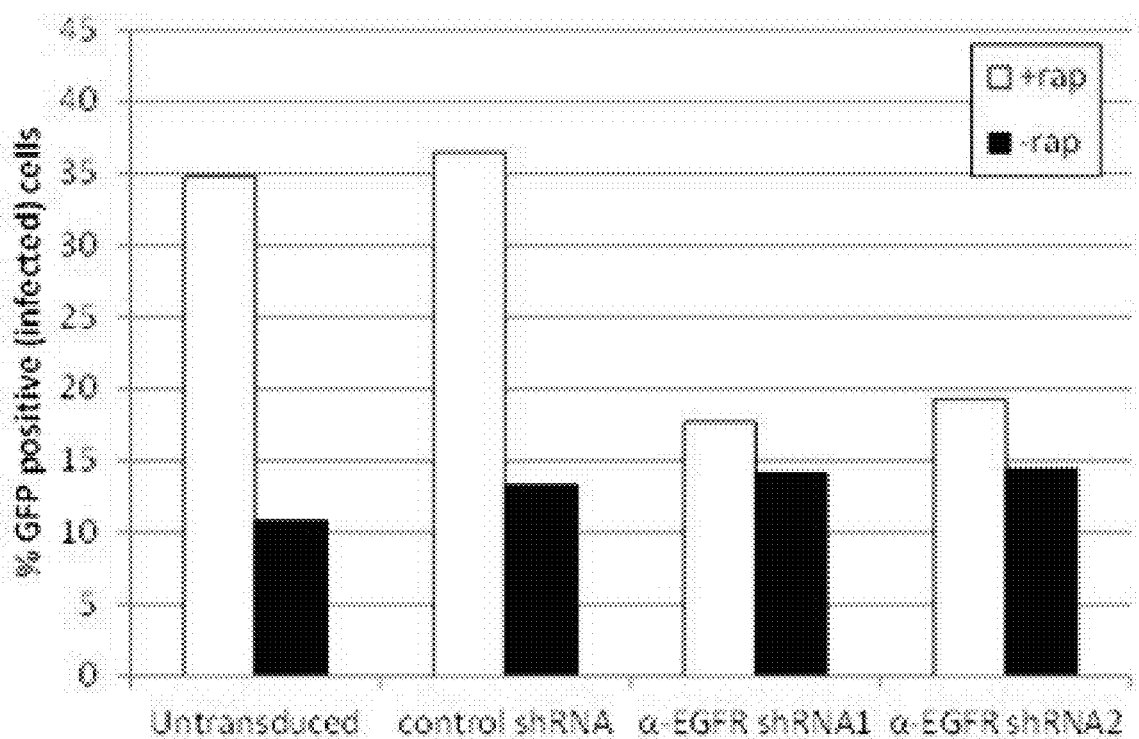
FIGS. 21A-21C. EGFR-dependent infection of Ad-178. Infection quantified by FACS, counting cells expressing adenovirus-delivered GFP gene, >30k events each.
Figure 21B:
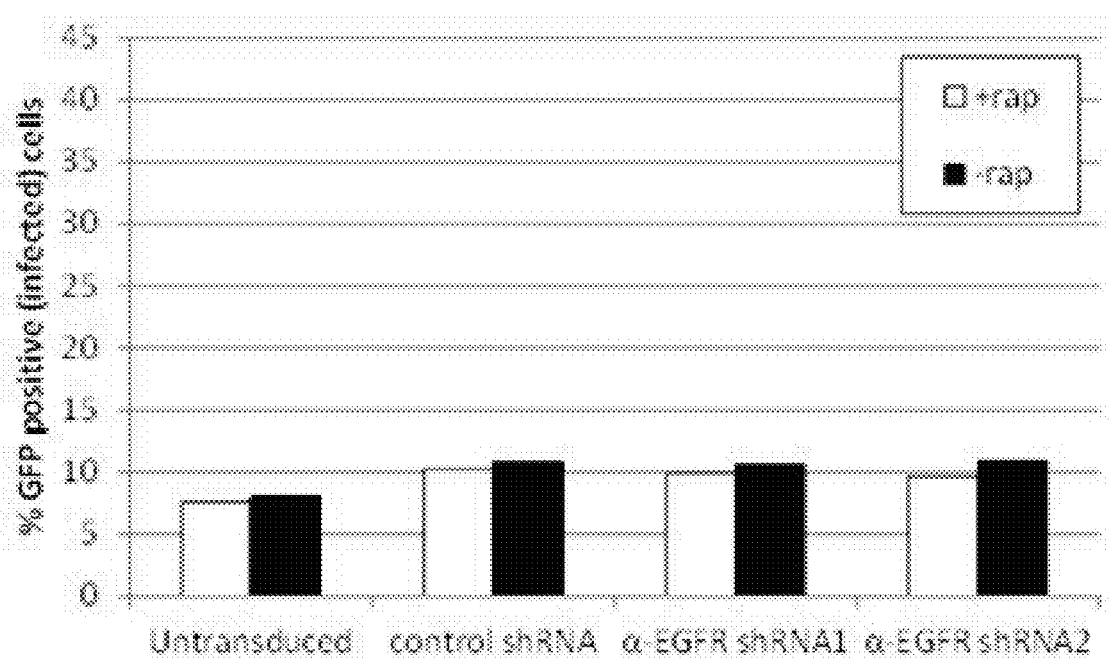
Figure 21C:
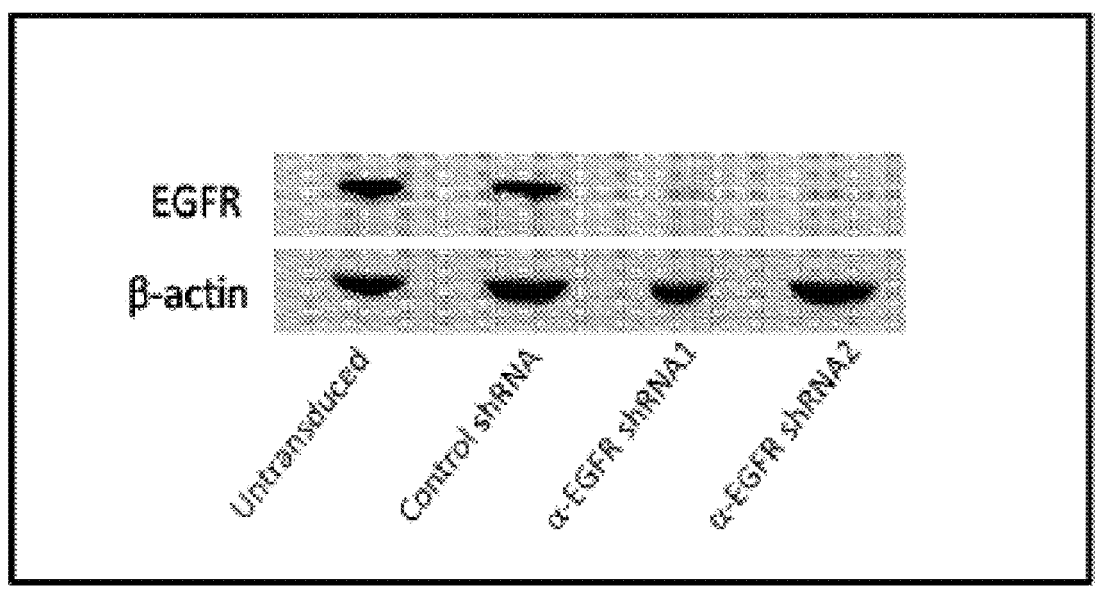
Figure 22:
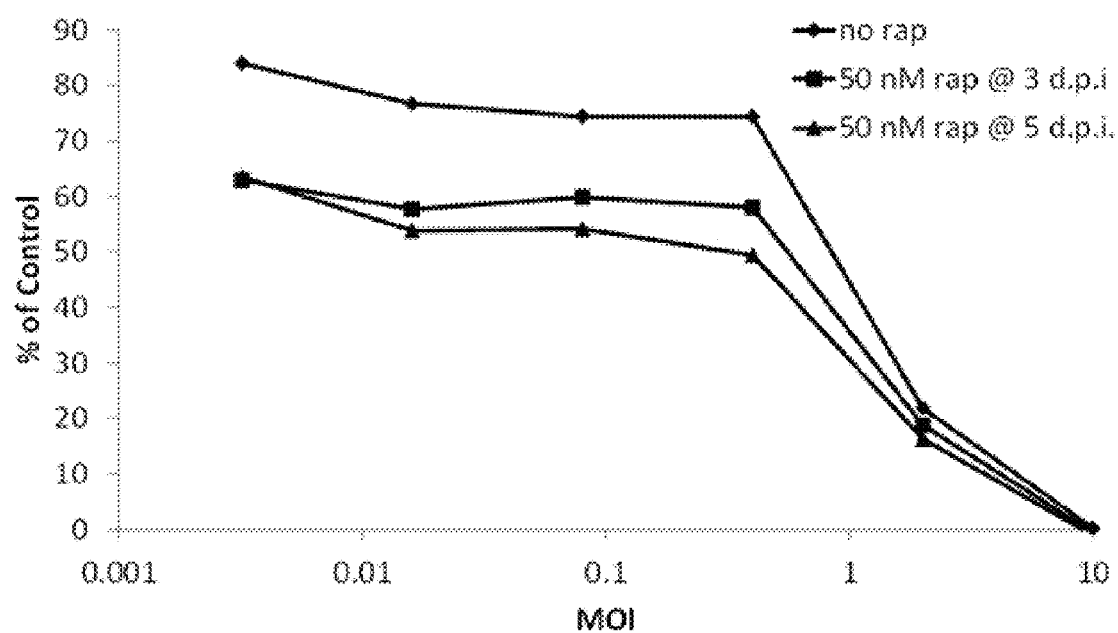
FIG. 22. Rapamycin induced EGFR-retargeting of Ad-178 enhances cell killing of HS578T. CPE assay using WST-1 reagent for % metabolic activity vs. uninfected cells 9 days post infection. 50 nM rapamycin added to cells at time points indicated in figure legend. Data points shown are averages of samples in triplicate.
Figure 23A:
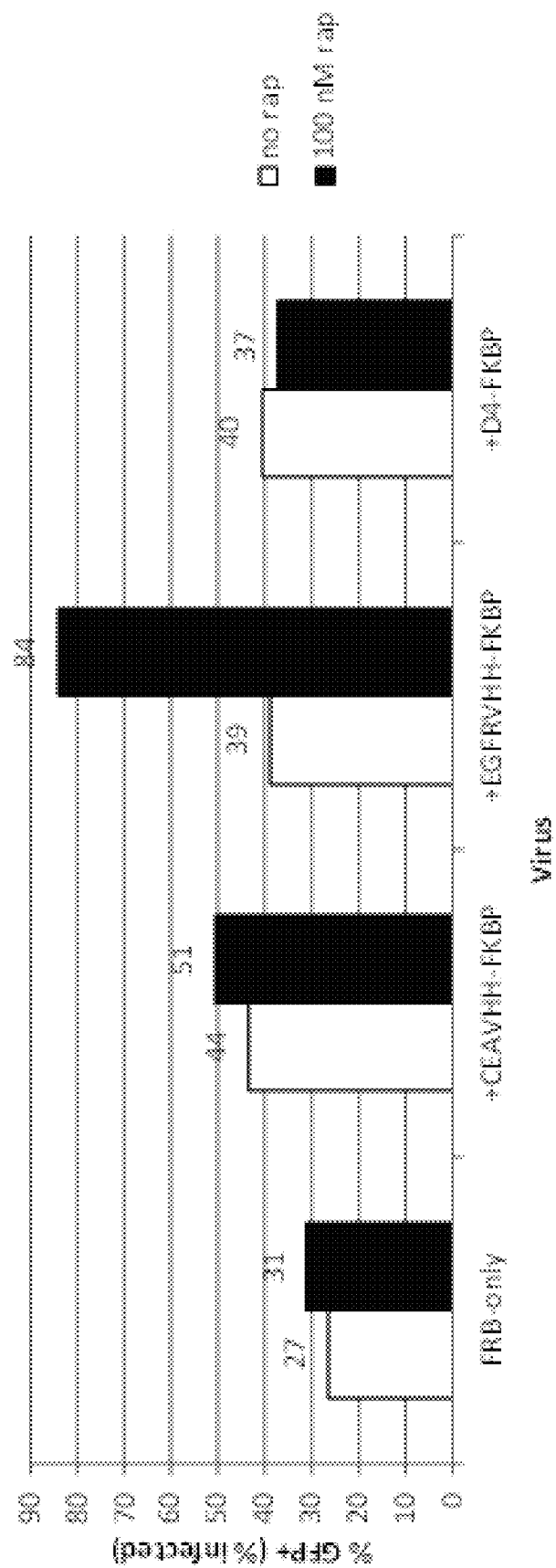
Figure 23C:
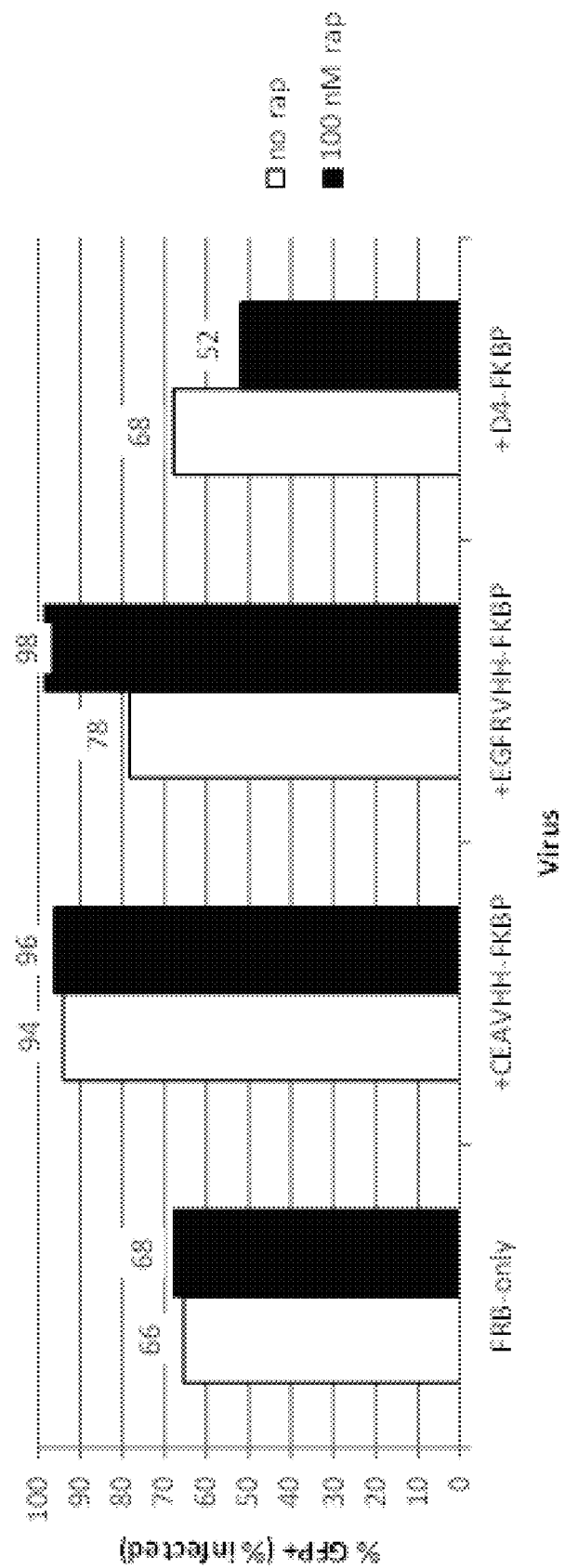
Figure 23D:
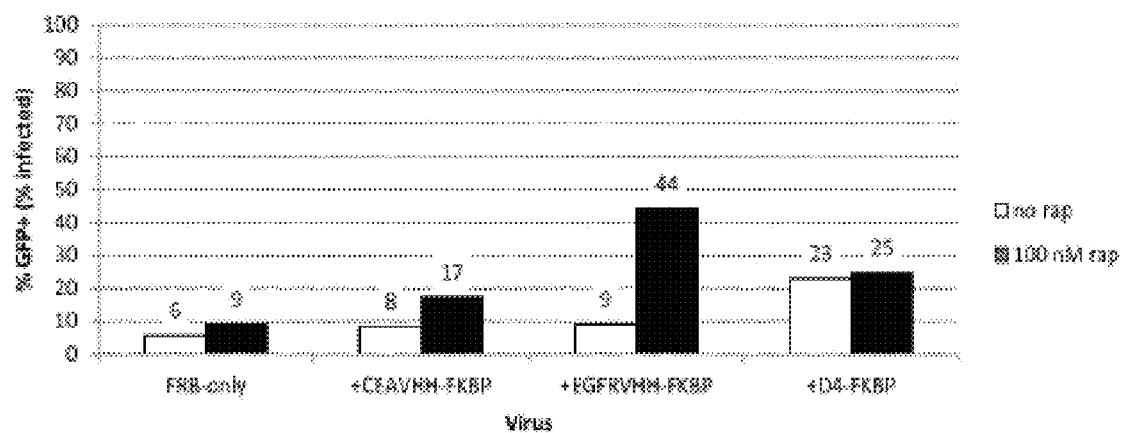
Figure 23E:
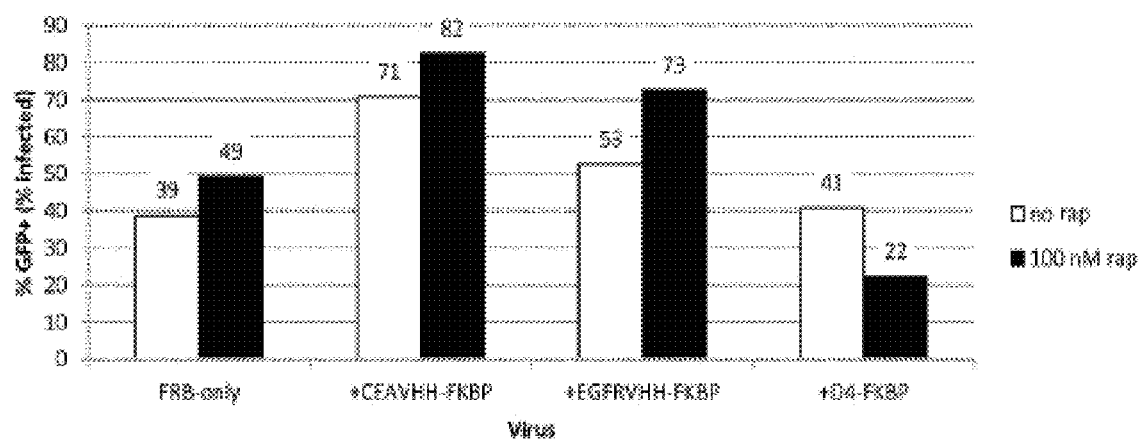
Figure 23F:
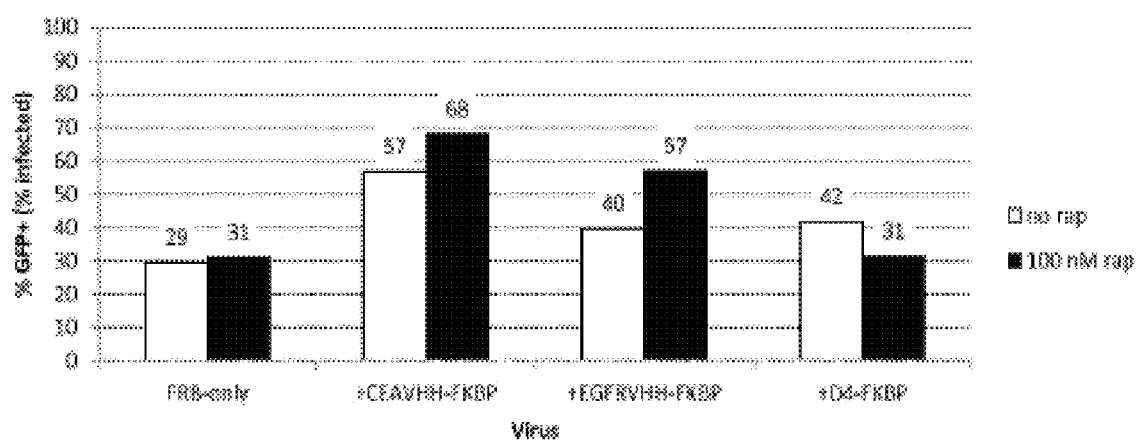
Figure 23G:
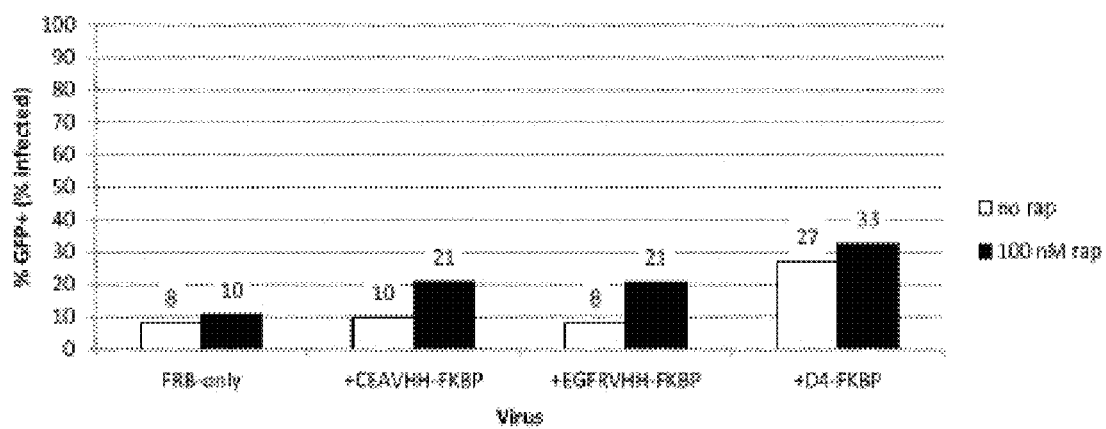
Figure 23H:
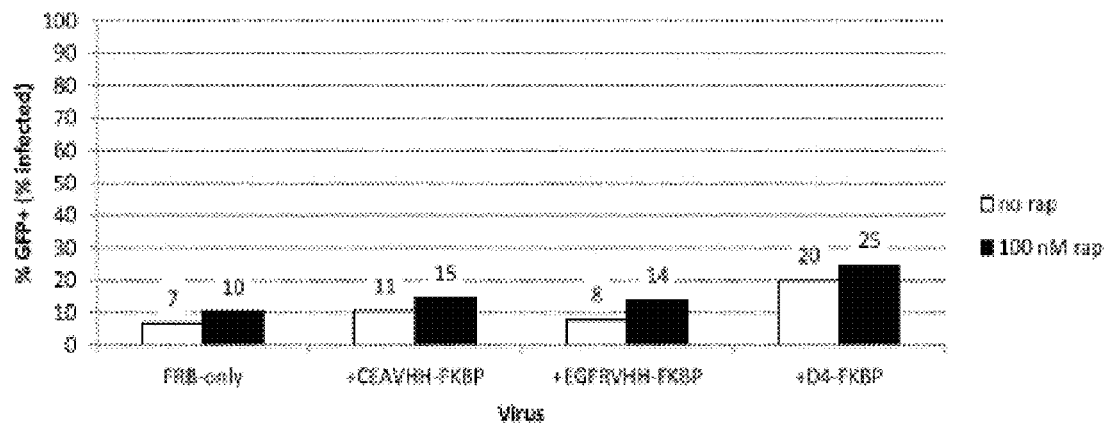
Figure 24A:
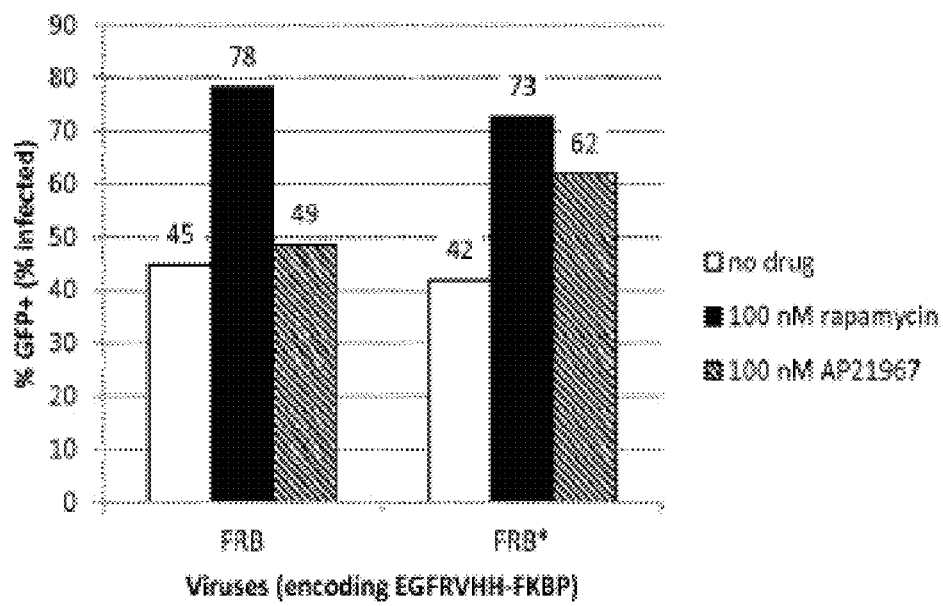
FIGS. 24A-24D. Targeted infection of cell lines using AP21967 and mutant FRB domain-containing Ad. The adenoviruses were prepared in the presence or absence of 100 nM rapamycin or 100 nM AP21967 by infection of 293 E4 cells, and supernatant was used to infect the targeted cell lines.
Figure 24B:
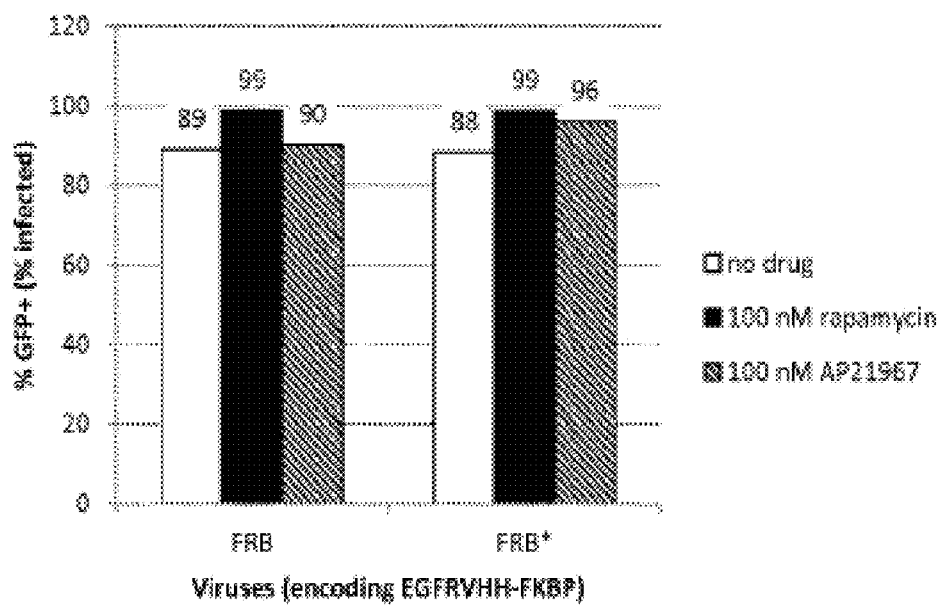
Figure 24C:
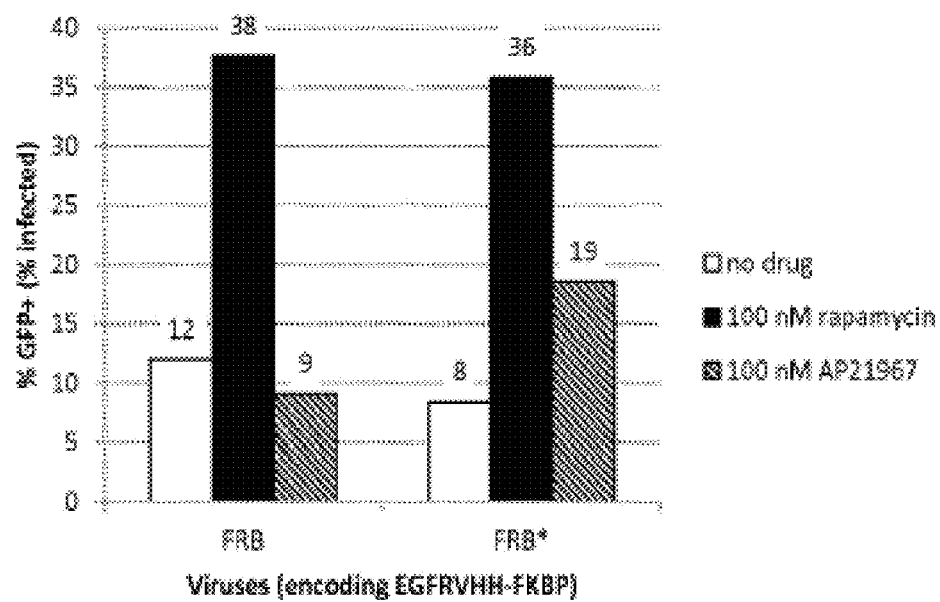
Figure 24D:
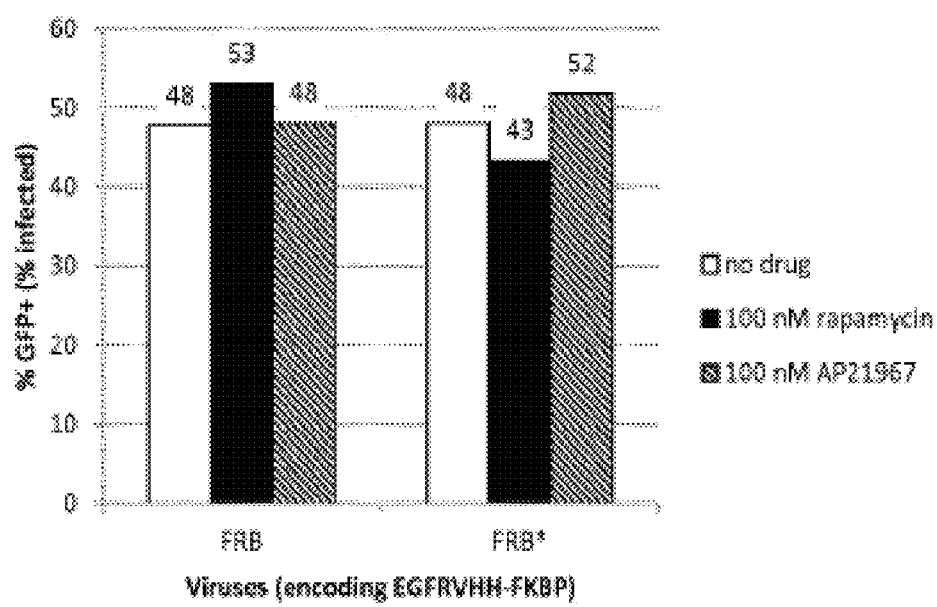
Figure 25:
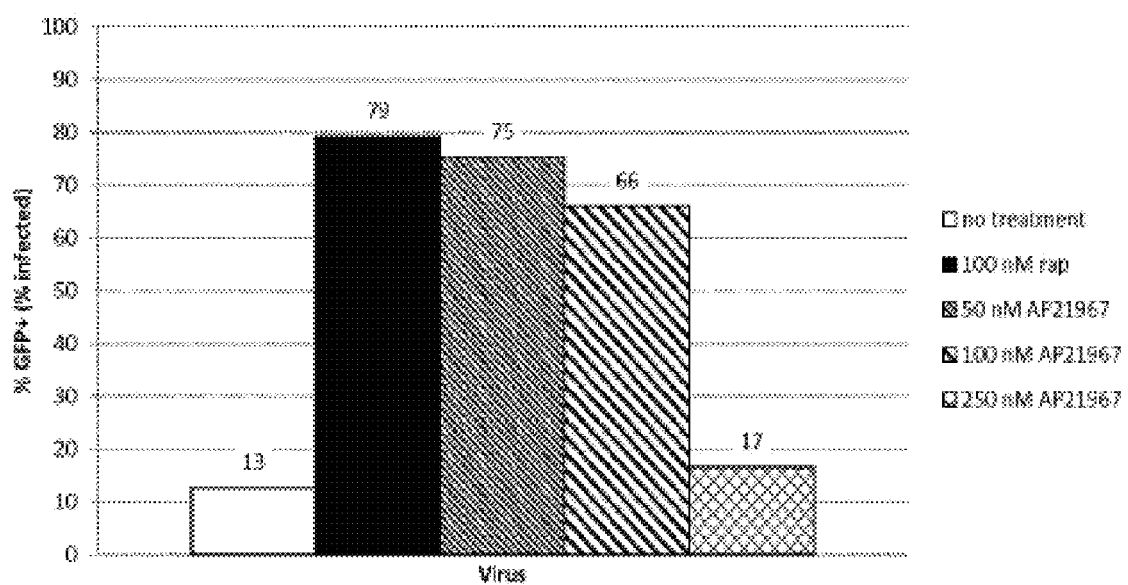
FIG. 25. Targeted infection of cell lines using AP21967 and mutant FRB domain-containing Ad. The EGFR-targeted adenovirus containing the FRB-mutant in the capsid was prepared with a range of concentration of AP21967 or 100 nM rapamycin were prepared by infection of 293 E4 cells, and supernatant was used to infect the MDA MB 453. Numbers on top of the columns represent % of GFP (i.e. infected) cells.
Figure 26:
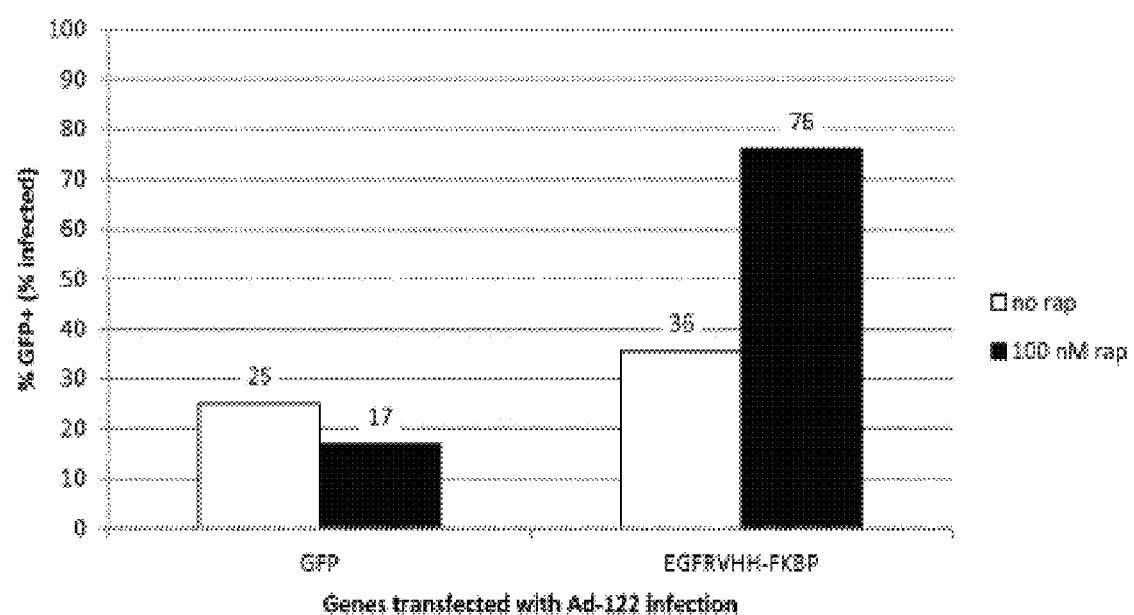
FIG. 26. Targeted infection of cell lines ectopically expressed ligand-FKBP fusion, EGFRVHH-FKBP. The ligand-FKBP fusion (or GFP as a control) was transiently expressed in 293 E4 cells, and infected with Ad-122. The virus was prepared in the presence of absence of 100 nM rapamycin, and the supernatant was used to infect the MDA MB 231. Numbers on top of the columns represent % of GFP (i.e. infected) cells.
Figure 27A:
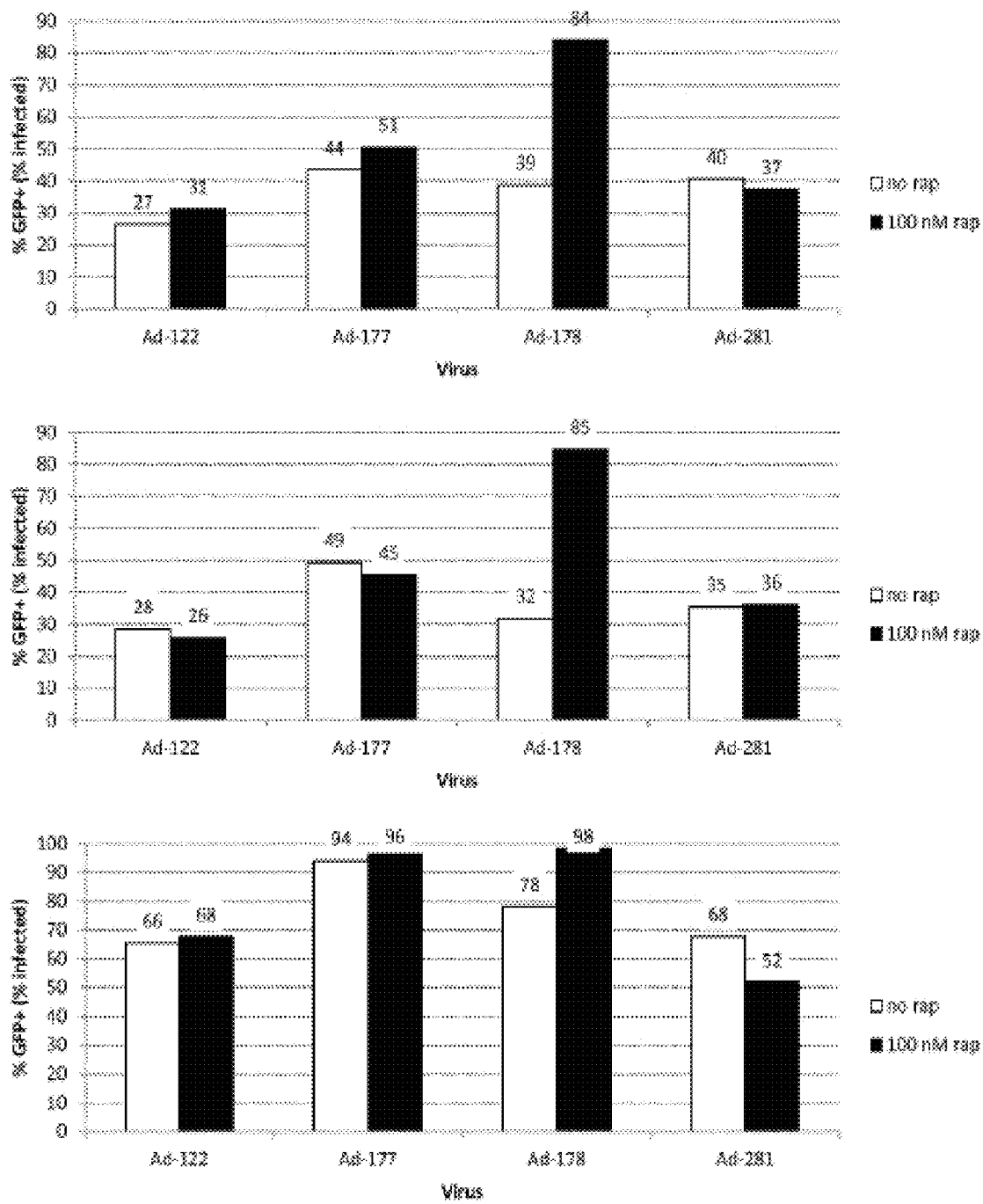
FIGS. 27A-27C. Targeted infection of cell lines by control Ad, or by Ad encoding ligands fused to FKBP. The adenoviruses were prepared in the presence or absence of 100 nM rapamycin by infection of 293 E4 cells, and supernatant was used to infect the targeted cell lines.
Figure 27B:
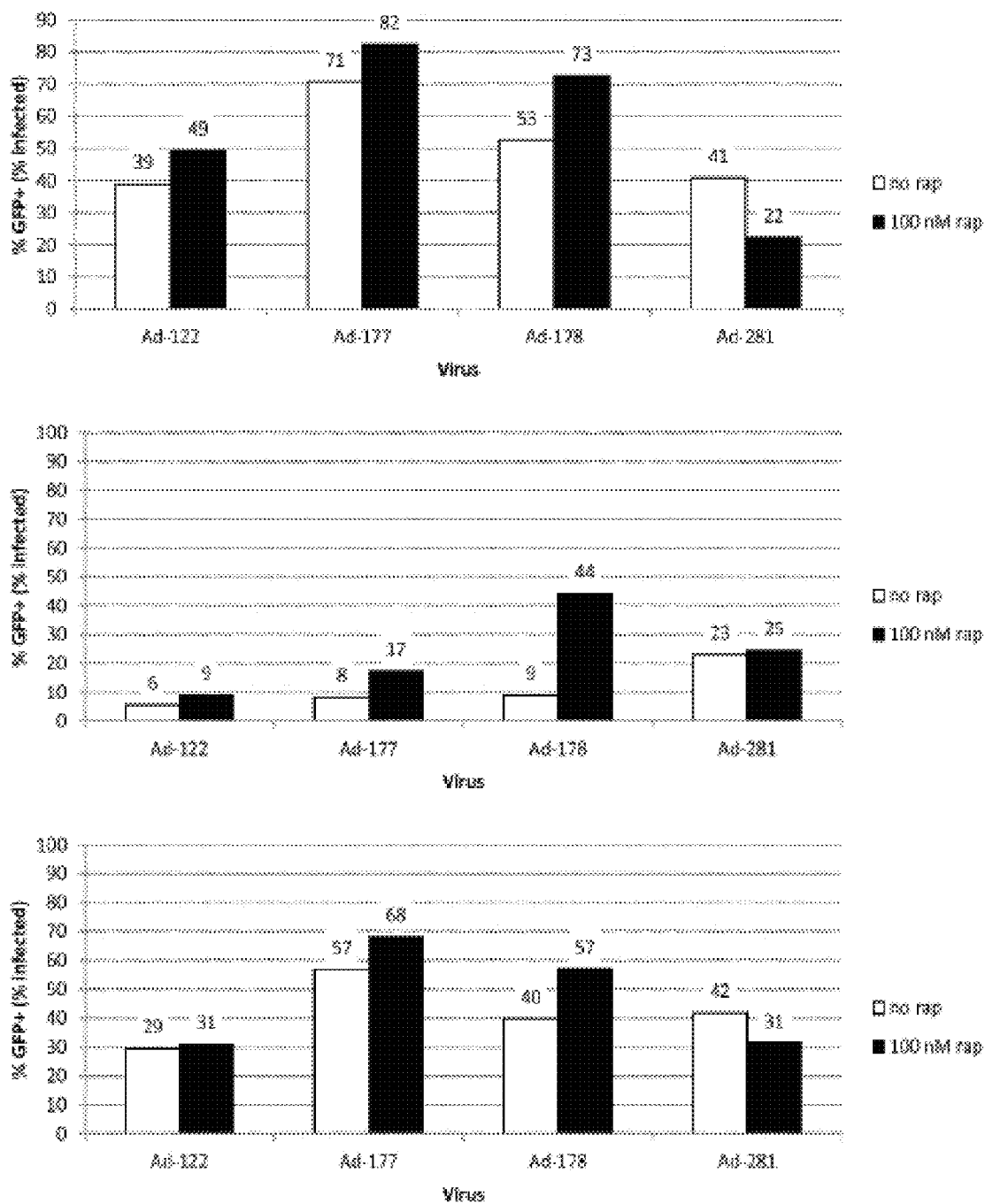
Figure 27C:
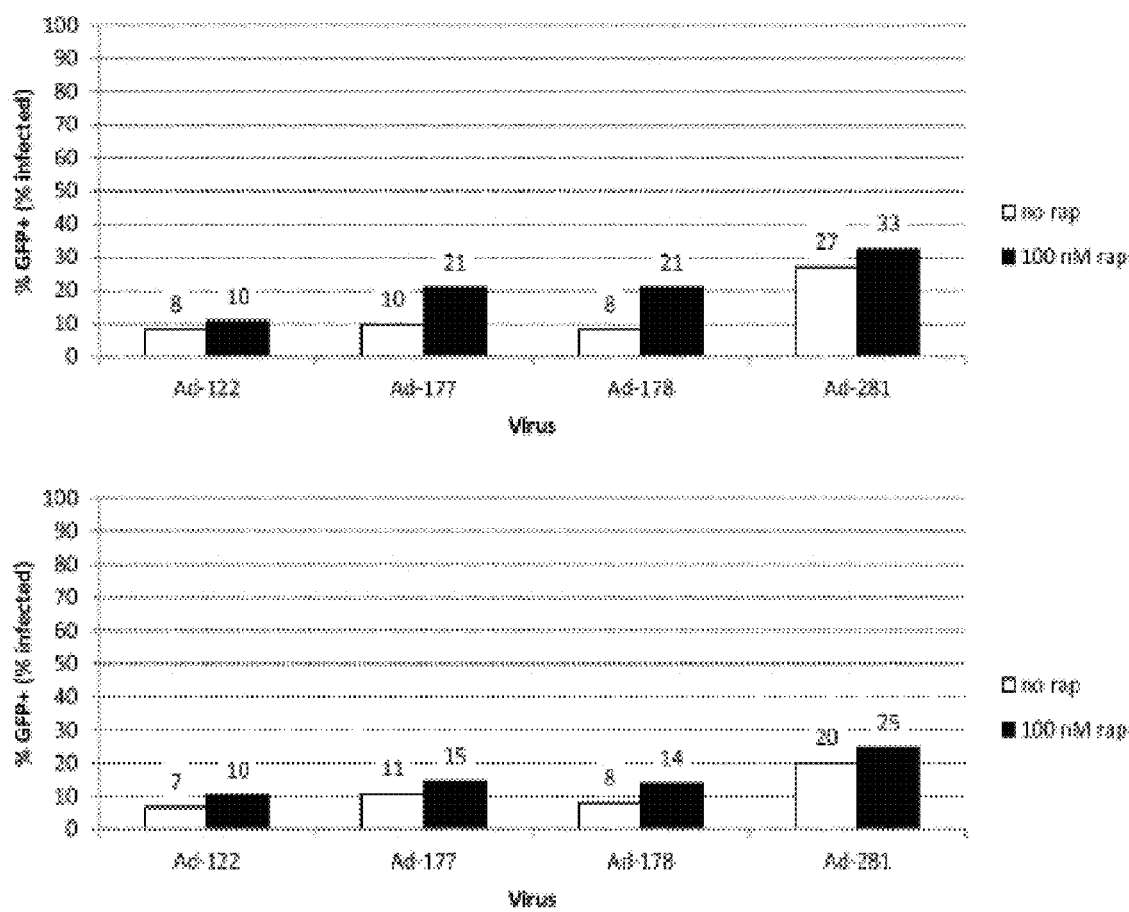

Immunofluorescence to Detect Rapamycin-Induced Colocalization of FRB-Fiber and VHH-FKBP Fusion Proteins Detection of the colocalization of proteins in cells by immunofluorescence or via fluorescently tagged proteins is one approach to evaluate if proteins have the potential for interaction. A difference of FKBP localization to FRB-fiber (or vice versa) in the presence of rap versus the absence would suggest that rap was inducing their association. 293 E4 cells grown on microscope slides for direct imaging of adenovirus expressed proteins are infected. FRB-fiber and VHH-FKBP fusion proteins are evaluated in cells which have 500 nM rap versus solvent control to evaluate any differences in localization due to presence of the drug. As controls, a virus with the Adsembly strategy is constructed that expresses CEAVHH-FKBP and wt fiber (Ad-199) as a control for FRB-dependent rap-induced colocalization of FKBP. Non-confocal IF imaging in infected 293 E4 cells shows colocalization of FRB-fiber and VHH-FKBP signals in the presence of rap (FIG. 14).

Co-Immunoprecipitation (CoIP) of FRB-Fiber and VHH-FKBP Fusion Proteins Via Rapamycin Induced Heterodimerization CoIP of FRB-fiber through IP of FKBP (and vice versa) from the lysates of infected 293 E4 cells have been performed. Viruses used are the experimental group, Ad-177 or Ad-178, to evaluate rap-induced FRB-FKBP association; Ad-122 (no FKBP, FRB-fiber) to evaluate any background of endogenous FKBP heterodimerization, and Ad-199 (CEAVHH-FKBP, wt fiber) as a negative control (for complete virus list, see Table 1). 293 E4 cells are infected with a multiplicity of infection (MOI) of 10, and media are replaced 4 hours after addition of virus. The cells are treated with 500 nM rap or solvent control (EtOH) at 24 h p.i., and are collected for lysis 36 h p.i. Total cell extract are used for IP.

To demonstrate that the FRB/FKBP interaction is biologically relevant and occurring on the surface of adenovirus particles, CoIP of the VHH-FKBP through non-fiber adenovirus capsid proteins from the lysates of infected 293 E4 cells are performed. In addition, purification of Ad-177 and Ad-178 by CsCl gradient ultracentrifugation and anion exchange with and without rap is performed to see if the VHH-FKBP is (nonimmuno)precipitated/retained through these processes in the presence of rap.

Rapamycin Induced Retargeting of Virus Tropism

The dimerization induced by rap on FKBP-retargeted viruses should enable them to infect via disparate receptors based on the affinity of the targeting moiety to a cellular receptor. That principle is demonstrated with the Ad-177, Ad-178 viruses directed to CEA and EGFR respectively. Ad-177 and Ad-178 are used to infect 293 E4 cells and treated with 500 15 nM rap or solvent control. Viruses are harvested from the media 48 h p.i. and directly used to infect a panel of cancer cell lines. Cells were infected in duplicate and at different dilutions of the infectious media (i.e.: undiluted, 2-fold, 4-fold, etc.). Infection is determined by quantifying the number of GFP positive cells by FACS and high-throughput imaging.

The FKBP-ligand fusion can also be expressed ectopically in infected cells to enable targeting of recombinant adenovirus with an inserted FRB-domain in the capsid. If an FKBP-ligand and dimerizing agent is present with the recombinant adenovirus, the targeted complex should assemble, even if the FKBP-ligand was not expressed from the adenovirus genome. We will transiently express EGFRVHH-FKBP ectopically (from a plasmid), then infect cells with Ad-122. Ad-122 alone was not targeted in the presence of rapamycin, but in the additional presence of EGFRVHH-FKBP, there was enhanced infection (FIG. 26). The ability to express the FKBP-ligand ectopically will enable rapid screening of ligand candidates or ligands in a library, without the need to assemble new recombinant adenovirus genomes. For example, in a multi-well format, each well of cells could transiently express a pool of ligand-FKBPs, each would be infected with Ad-122, and the resulting viral supes (supernatant) could be applied to cells in culture to quantify enhancement of targeting. The identity of the members in the ligand-FKBP pool can be further tested individually. Further, effective ligand-FKBP clones can be mutagenized and re-screened to enhance the effectiveness of targeted adenovirus infection.

Validate Retargeting Specificity

The effects observed from rapamycin-preparation of viruses should be confirmed that the interaction is gained via interaction with the VHH-targeting moiety to verify the system. In the cases of viruses that exhibit retargeting and different tropisms, specificity is verified by using different VHH fusions, by knocking down CAR and the cellular target of the VHH via shRNA (e.g. EGFR knockdown for Ad-178), or blocking the cellular target with exogenous antibodies or VHH (e.g. add excess exogenous EGFRVHH to block before Ad-178 infection). Alternative chemical-induced dimer systems such as orthogonal FRB/FKBP mutants that utilize rap analogs (rapalogs) may also be necessary if endogenous mTOR or FKBP interfere with virus component assembly. Alternatively other dimerization systems could be explored (Hubbard, K. E., et al., *Genes & Development,* 24(16): p. 1695-1708 (2010)).

Rapalog Induced Retargeting of Virus Tropism

Since rapamycin may exhibit undesirable biological effects, such as growth and proliferation arrest (Jacinto E, Hall M N. Tor signalling in bugs, brain and brawn. Nat Rev Mol Cell Biol. 2003; 4(2):117-26), an biologically orthogonal molecule with the same heterodimerizing capability is used to retarget adenovirus infection. The rapalog AP21967 (FIG. 7) is able to form stable heterodimers with FKBP and a mutant FRB domain (mTOR mutation T2098L), but not with the wt FRB domain (Bayle J H, Grimley J S, Stankunas K, Gestwicki J E, Wandless T J, Crabtree G R. Rapamycin analogs with differential binding specificity permit orthogonal control of protein activity. Chem Biol. 2006; 13(1):99-

107). The recombinant adenovirus encoding EGFRVHH-FKBP and the mutant FRB-modified fiber (Ad-220) was assembled and tested for targeting using either rapamycin or AP21967. Both rapamycin and AP21967 were able to retarget Ad-220, while the control virus was only targeted with rapamycin and not AP21967.

V. Material and Methods

Adsembly

Modified adenoviruses were made with the below referenced components. Gateway DONR vectors were employed. In the example of human Ad5, the E1 module was obtained by PCR and inserted into the vector pDONR P1P4 using SLIC. The pDONR P1P4 vector backbone including attL1 and attL4 recombination sites was amplified using PCR and combined with the Ad5 E1 module by SLIC. In order to generate an alternate counter-selection cassette, vector pDONR P1P4 was modified. This vector backbone including attP1 and attP4 recombination sites was amplified using PCR and combined with the PheS$_{A294G}$ mutations and a Tetracycline resistance cassette (the pLac-Tet cassette from pENTR L3-pLac-Tet-L2) to create a new DONR vector. The attR1-PheS$_{A294G}$Tet(r)-attR4 fragment from the new DONR vector was then amplified by PCR and inserted into the Adsembly DEST vector. See "MultiSite Gateway® Pro Plus", Cat#12537-100; and Sone, T. et al. *J Biotechnol.* 2008 Sep. 10; 136(3-4):113-21.

In the example of human Ad5, E3 module was inserted into the pDONR P5P3r vector by gateway BP reaction. The E4 module was inserted into pDONR P3P2 vector by gateway BP reaction. The attR5-ccdB-Cm(r)-attR2 fragment from the pDONR P5P2 vector was amplified by PCR and inserted into the Adsembly DEST vector. See "MultiSite Gateway® Pro Plus", Cat#12537-100; and Sone, T. et al. *J Biotechnol.* 2008 Sep. 10; 136(3-4):113-21.

The vector backbone for the Adsembly DEST vector is composed of parts from three different sources. The Amp(r) cassette and lacZ gene was amplified from plasmid pUC19. This was combined with the p15A origin of replication, obtained from plasmid pSB3K5-I52002, part of the BioBricksiGEM 2007 parts distribution. The p15A ori, which maintains plasmids at a lower (10-12) copy number is necessary to reduce E1 toxicity. Lastly, in order to create a self-excising virus, the mammalian expression cassette for the enzyme IScel was PCR amplified from plasmid pAdZ5-CV5-E3+. This cassette was cloned into the vector backbone to create the vector called p15A-Scel. This is the vector used to start genome assembly. In the example of human Ad5, the gene modules were all obtained from either DNA purified from wild type Ad5 virus or the plasmid pAd/CMV/V5/DEST (Invitrogen).

Regarding the DEST vector in the example of human Ad5, the E2 and L3 modules were inserted into plasmid p15A-Scel by 3-fragment SLIC. The counterselection marker expressing ccdB and Chlor(r) flanked by attR5 and attR2 sites was obtained by PCR from plasmid pDONR P5P2. The second counterselection marker (PheS-Tet), was obtained by PCR from the vector pDONR P1P4 PheS$_{A294G}$-Tet (see above). The two counter-selection markers were inserted on the right (ccdB/Cm) and left (PheS/Tet) sides of p15A-Scel E2-L4 by SLIC after cutting with unique restriction enzymes engineered to the ends of the E2 and L4 modules to create the DEST vector (pDEST E2-L5).

Regarding the multisite gateway entry vector containing adenoviral gene modules, in the example of human Ad5, the E1 module were inserted into pDONR P1P4 by SLIC. The E3 module was inserted into pDONR P5P3R by gateway BP reaction. The E4 module was inserted into pDONR P3P2 by gateway BP reaction.

Regarding Amp(r) cassette: plasmid pUC19, the p15A ori: plasmid pSB3K5-I52002 was part of the BioBricksiGEM 2007 parts distribution. Regarding the adenoviral gene modules, either the DNA purified from Ad5 particles, or plasmid pAd/CMV/V5/DEST (Invitrogen). The DONR vectors pDONR P1P4, P5P2, P5P3R, P3P2 were received from Jon Chesnut (Invitrogen). The PheS gene was derived from DH5alpha bacterial genomic DNA and subsequently mutated by quick change to create the PheS$_{A294G}$ mutant. Regarding the Tet(r) gene, the plasmid pENTR L3-pLac-Tet-L2 was received from Jon Chesnut (Invitrogen).

Regarding an embodiment of the Adsembly method, 20 fmol of a dual DEST vector, typically containing a core module flanked by two counterselection cassettes, is combined with 10 fmol of each remaining entry vector containing gene modules. In the example of Ad5, this includes combining 20 fmol of the E2-L3 dual DEST vector with 10 fmol each of an E1 module entry vector, an E3 module entry vector, and an E4 module entry vector. In some cases, increasing the amount of one or more of the entry vectors may increase efficiency (e.g. using 50 fmol of the E1 module entry vector for Ad5). These vectors are combined with 2 µl of LR Clonase II (Invitrogen) in a final volume of 10 µl. The reaction is incubated at 25° C. overnight (12-16 hours). The reaction is stopped by the addition of 1 µl of proteinase K (Invitrogen) and incubation at 37° C. for 10 minutes. Five µl of the reaction is then transformed into high competency bacteria (>1e9 cfu/µg) that are sensitive to the ccdB gene product and plated onto YEG-Cl agar plates (as described in Kast, P. Gene, 138 (1994) 109-114; when using PheS$_{A294G}$ counterselection) or other appropriate media for the counterselection used in the vector. Colonies are subsequently isolated and screened for complete genomes. Complete genomes are directly transfected into 293 E4 cells, resulting in infectious particles 5-9 days post-transfection.

Regarding PCRs, all PCRs were performed using the Phusion enzyme (NEB). PCRs to obtain the ADENOVIRAL GENE modules from Ad5 were performed with 1xHF buffer, 200 µM each dNTP, 0.5 µM each primer, and 10 ng of template. For the E2-L2 module, 3% DMSO was also added. Template was either plasmid pAd/PL-DEST (Invitrogen; for E2-L2, L3-L4, and E4 modules) or Ad5 genomic DNA (for E1 and E3 modules). PCR conditions were as follows. E2-L2 and L3-L4: 98° C. 30 sec-10 cycles of 98° C. 10 sec, 65° C. 30 sec (decrease temp 1° C. every 2 cycles), 72° C. 7 min-29 cycles of 98° C. 10 sec, 60° C. 30 sec, 72° C. 8 min-72° C. 10 min-4° C. hold. E3: 98° C. 30 sec-10 cycles of 98° C. 10 sec, 70° C. 30 sec (decrease temp 0.5° C. every cycle), 72° C. 2 min 30 sec-25 cycles of 98° C. 10 sec, 68° C. 30 sec, 72° C. 2 min 30 sec-72° C. 10 min-4° C. hold. E4: 98° C. 30 sec-6 cycles of 98° C. 10 sec, 63° C. 30 sec (decrease temp 0.5° C. every cycle), 72° C. 2 min-29 cycles of 98° C. 10 sec, 60° C. 30 sec, 72° C. 2 min-72° C. 5 min-4° C. hold. Regarding obtaining viral genomic DNA from purified virus, up to 100 µl of purified virus is added to 300 µl of lysis buffer containing 10 mM Tris pH 8, 5 mM EDTA, 200 mM NaCl, and 0.2% SDS. Mix is incubated at 60° C. for 5 min, followed by addition of 5 µl of proteinase K stock (~20 mg/mL) and further incubated at 60° C. for 1 hour. Samples are then placed on ice for 5 min, followed by spinning at 15Kxg for 15 min. Supernatant is removed and added to an equal volume of isopropanol, mixed well, and spun at 15Kxg for 15 min at 4° C. Pellet is washed with 70% ethanol and re-spun for 15 min at 4° C. The pellet is dried and resuspended for use.

Regarding SLIC, linear fragments are exonuclease treated for 20 min at room temp in the following 20 µl reaction: 50 mM Tris pH 8, 10 mM $MgCl_2$, 50 µg/mL BSA, 200 mM Urea, 5 mM DTT, and 0.5 µl T4 DNA polymerase. The reaction is stopped by addition of 1 µl 0.5 M EDTA, followed by incubation at 75° C. for 20 min. An equal amount of T4-treated DNAs are then mixed to around 20 µl in volume in a new tube. For SLIC combining 2 fragments, 10 µl of each reaction is used. For SLIC combining 3 fragments, 7 µl of each reaction is used.

Fragments are annealed by heating to 65° C. for 10 min, followed by a slow cool down decreasing the temperature 0.5° C. every 5 seconds down to 25° C. After annealing, 5 µl of the reaction is transformed and clones are screened.

Retargeted Virus Preparation

Regarding virus production, concentration and purification, 293 E4 cells are infected with infectious particles, and approximately 48 hours post-transfection when CPE is apparent, the cells are collected and isolated by centrifugation at 500×g for 5 minutes. The cells are lysed in TMN buffer (10 mM TrisCl pH 7.5, 1 mM $MgCl_2$, 150 mM NaCl) via 3× freeze/thaws, and the cell debris was removed by two rounds of centrifugation at 3K×g and 3.5K×g for 15 minutes. A cesium chloride gradient (0.5 g/mL) is used to band virus particles via ultracentrifugation at 37K×g for 18-24 hours. The band is collected and dialyzed in a 10k MWCO Slide-A-Lyzer® dialysis cassette (Thermo Scientific) in TMN with 10% glycerol overnight (12-18 h) at 4° C., then stored at −80° C. The titer of the purified virus is determined versus a titered wildtype standard by a cell-based serial dilution infection ELISA with anti-adenovirus type 5 primary antibody (ab6982, Abcam), and ImmunoPure anti-rabbit alkaline phosphatase secondary antibody (Thermo Scientific).

Regarding insertion of the FRB domain of mTOR into the adenovirus fiber, the FRB domain was inserted into the H1-loop region of the fiber gene in the Adsembly entry vector pENTR E3-L5 by SLIC. The 90aa FRB domain of mTOR (amino acids Glu2025-Gln2114) was PCR amplified from pRK5 mTOR-myc (R. Shaw) for insertion into PCR amplified pENTR E3-L5 with ends flanking the adenovirus fiber H1-loop between Thr546 and Pro547 to generate the resulting vector, pENTR E3-L5 (FRB-Fiber).

Regarding mutation of the FRB domain of mTOR to be specific for AP21967 binding, the FRB domain was mutated using standard techniques in the Adsembly entry vector pENTR E3-L5 (FRB-Fiber) and pENTR E3-L5 (ΔRID, EGFRVHH-FKBP, FRB-Fiber). The residue Thr2098 (mTOR numbering) was mutated to Leu. This resulted in the Adsembly entry vectors pENTR E3-L5 (FRB*-Fiber) and pENTR E3-L5 (ΔRID, EGFRVHH-FKBP, FRB*-Fiber).

Regarding adenovirus-encoded fluorescent reporter for infection, the sequence for GFP was inserted 5' of the adenovirus E1A gene to generate the fusion described by Zhao, L. J. et al. *J Biol Chem.* 2006 Dec. 1; 281(48):36613-23. The GFP gene was PCR amplified with the described C-linker sequence for insertion into PCR amplified pENTR E1 with ends flanking the start codon of adenovirus E1A to generate the resulting plasmid, pENTR E1 (GFP-E1A).

Regarding expression of FKBP from virus genome, the FKBP sequence was inserted by SLIC into pENTR E3-L5, replacing the adenovirus RIDα, RIDβ, and 14.7K genes. The FKBP gene was PCR amplified from pcDNA-FKBP12-Crluc (S. Gambhir) for insertion into PCR amplified pENTR E3-L5 and pENTR E3-L5 (FRB-Fiber) lacking the sequence from the start codon of RIDα to the stop codon of 14.7 to generate the resulting vectors, pENTR E3-L5 (ΔRID, FKBP) and pENTR E3-L5 (ΔRID, FKBP, FRB-Fiber). Alternative FKBP insertion locations were constructed, but did not appear to lead to accumulation of FKBP during infection via immunoblot (C-term IRES-driven expression on E1 transcript, C-term IRES-driven expression on fiber transcript, or Fiber-Furin2A-FKBP autocleavage sequence).

Regarding retargeting moiety genetic fusion with FKBP, 3D modeling in PyMol of FRB-Fiber in rapamycin-dependent complex with FKBP revealed an advantage to fuse the targeting moiety to the N-terminus of FKBP. In the case of the camelid antibody variable heavy chain (VHH) with EGFR binding specificity (EGFRVHH), EGFRVHH was gene synthesized by Blue Heron Biotech, and inserted at the N-terminus of FKBP in pENTR E3-L5 (ΔRID, FKBP) and pENTR E3-L5 (ΔRID, FKBP, FRB-Fiber) by SLIC with a GSGSGST linker sequence, to generate the plasmids pENTR E3-L5 (ΔRID, EGFRVHH-FKBP) and pENTR E3-L5 (ΔRID, EGFRVHH-FKBP, FRB-Fiber).

Retargeting Experiments

Regarding rapamycin-induced retargeting adenovirus infection via EGFR by EGFRVHH-FKBP, a virus was constructed using Adsembly with pENTR E1 (GFP-E1A), pENTR E3-L5 (ΔRID, EGFRVHH-FKBP, FRB-Fiber), pENTR E4, and pDEST E2-L5, referred to hereafter as Ad-178, to infect a panel of cancer cell lines. Ad-178 was used to infect 293 E4 cells at MOI 10. Twenty-four hours following the infection 50 nM rapamycin was added to the medium. The concentration of rapamycin was optimized by testing a range of rapamycin concentrations with Ad-178 to infect MDA MB 453. Forty-eight hours following infection, the media containing infectious particles was collected and filtered through a 0.22 µm pore filter. The filtered media was used in serial dilution to infect a panel of cancer cell lines in black-walled 96-well plates or 6-well plates, and virus similarly prepared without the addition of rapamycin was used to infect an identical set of cells in parallel as the control. The media was replace 3 hours post-infection.

Regarding rapalog-induced retargeting adenovirus infection via EGFR by EGFRVHH-FKBP, a virus was constructed using Adsembly with pENTR E1 (GFP-E1A), pENTR E3-L5 (ΔRID, EGFRVHH-FKBP, FRB*-Fiber), pENTR E4, and pDEST E2-L5, referred to hereafter as Ad5-220. Ad5-220 was used to infect 293 E4 cells at MOI 10. Twenty-four hours following the infection 100 nM AP21967 was added to the medium. Forty-eight hours following infection, the media containing infectious particles was collected and filtered through a 0.22 µm pore filter. The filtered media was used to infect cancer cell lines in 12-well plates, and viruses similarly prepared with the addition of rapamycin or without the addition of AP21967 were used to infect an identical set of cells in parallel as controls. The media was replaced 1 hour post-infection.

Regarding rapamycin-induced retargeting adenovirus infection with ectopically expressed ligand-FKBP, 293 E4 cells were transiently transfected with EGFRVHH-FKBP (or GFP as a control), and 24 hours following transfection, were infected with Ad-122 at MOI 10. Twenty-four hours following the infection 100 nM rapamycin was added to the medium. Forty-eight hours following infection, the media containing infectious particles was collected and filtered through a 0.22 µm pore filter. The filtered media was used to infect MDA MB 231 cells seeded on 12-well plates. The media was replaced 1 hour post-infection.

Regarding quantification of the infection efficiency, 96-well plates were quantified by high-content imaging by counting % GFP-positive cells using IMAGEXPRESS™ software on an 25 IMAGEXPRESS™ Micro. The infection efficiency of 6-well or 12-well plates was quantified by counting % GFP-positive cells by FACS using a FACScan (BD Biosciences).

Regarding the specificity of the EGFRVHH retargeted adenovirus to EGFR, the effective shRNA B sequence from Engelman, J. A. et al. J Clin Inv. 2006 Oct. 2; 116(10):2695-706 was cloned under the control of an H1 promoter in the pLentiX2 puro vector (Addgene), and used to generate lentivirus to mediate EGFR knockdown in MDA MB 453 breast cancer cells. MDA MB 453s were transduced with the anti-EGFR shRNA construct or a control lentivirus encoding an shRNA directed against the luciferase gene, and were selected under 2 μg/mL puromycin. Knockdown efficiency was quantified by immunoblotting for EGFR in total protein. The retargeting assay as described above was repeated on the selected MDA MB 453 in 6-well plates, and the infection efficiencies were quantified by FACS using a FACScan (BD Biosciences).

VI. Tables

TABLE 1

Summary of designed novel adenoviruses.

| Ad-Serotype | Components | | | |
|---|---|---|---|---|
| Adenovirus | E1 | E2, E3 L3 | | E4 |
| Ad-122 (SEQ ID NO: 70) | GFP-E1A | wt | FRB-fiber | wt |
| Ad-177 (SEQ ID NO: 71) | GFP-E1A | wt | ΔE3-RIDα, ΔE3-RIDβ, ΔE3-14.7K replaced with CEAVHH-FKBP fusion; FRB-fiber | wt |
| Ad-178 (SEQ ID NO: 72) | GFP-E1A | wt | ΔE3-RIDα, ΔE3-RIDβ, ΔE3-14.7K replaced with EGFRVHH-FKBP fusion; FRB-fiber | wt |
| Ad-199 (SEQ ID NO 67) | GFP-E1A | wt | ΔE3-RIDα, ΔE3-RIDβ, ΔE3-14.7K replaced with CEAVHH-FKBP fusion; wt fiber | wt |
| Ad-200 (SEQ ID NO: 68) | GFP-E1A | wt | ΔE3-RIDα, ΔE3-RIDβ, ΔE3-14.7K replaced with EGFRVHH-FKBP fusion; wt fiber | wt |
| Ad-281 (SEQ ID NO: 109) | GFP-E1A | wt | ΔE3-RIDα, ΔE3-RIDβ, ΔE3-14.7K replaced with PA D4-FKBP fusion; FRB fiber | wt |
| Ad-220 (SEQ ID NO: 110) | GFP-E1A | wt | ΔE3-RIDα, ΔE3-RIDβ, ΔE3-14.7K replaced with EGFRVHH-FKBP fusion; FRB (mTOR T2098L) fiber | wt |

TABLE 2

Examples of dimerizing agents (DA), dimerizing agent binders of the capsid dimerizing-agent binder conjugate (DABC) and dimerizing agent binders of the ligand-dimerizing agent binder conjugate (DABL).

| DA | DABC | DABL |
|---|---|---|
| rapamycin | FRB | FKBP12 |
| AP21967 | FRB (with mTOR T2098L mutation) | FKBP12 |
| abscisic acid (ABA) | PYL1 | AB1 |
| 2,4-dichlorophenoxyacetic acid (CFA) inositol hexakisphosphate (IHP) indole-3-acetic acid (Auxin/IAA) | Tir1 | IAA7 |

TABLE 3

Examples of ligands included in the ligand-dimerizing agent binder conjugate and corresponding cell surface receptors bound by such ligands.

| Retargeting Element | Uniprot Accession Number\Sequence | Receptor | Uniprot Accession Number | Receptor Notes |
|---|---|---|---|---|
| apelin | Q9ULZ1 (SEQ ID NO: 73) | APLNR | P35414 (SEQ ID NO: 10) | Widely expressed in brain, glial cells, astrocytes, neuronal subpopulations, spleen, thymus, ovary, small intestine, and colon. |
| bradykinin | P01042 (SEQ ID NO: 74) | BDKRB1, B2 | P30411 (SEQ ID NO: 11) P46663 (SEQ ID NO: 12) | BDKRB1 is expressed in tissue injury, at sites of inflammation. B2 is ubiquitously expressed, widespread in normal smooth muscle and neurons. |
| calcitonin | P01258 (SEQ ID NO: 75) | CALCR | P30988 (SEQ ID NO: 13) | Receptor found on osteoclasts. |
| conantokin peptides | e.g. P07231 (SEQ ID NO: 76) | NMDAR1, 2A, 2B, 2C, 2D | Q05586 (SEQ ID NO: 14) Q12879 (SEQ ID NO: 15) Q13224 (SEQ ID NO: 16) Q14957 (SEQ ID NO: 17) O15399 (SEQ ID NO: 18) | Found upregulated in invasive tumor cells. |
| cholecystokinin | P06307 (SEQ ID NO: 77) | CCKAR, CCKBR | P32238 (SEQ ID NO: 19) P32239 (SEQ ID NO: 20) | Receptor found in CNS and gastrointestinal tract, upregulated in some colorectal and pancreatic tumors. |

TABLE 3-continued

Examples of ligands included in the ligand-dimerizing agent binder conjugate and corresponding cell surface receptors bound by such ligands.

| Retargeting Element | Uniprot Accession Number\Sequence | Receptor | Uniprot Accession Number | Receptor Notes |
|---|---|---|---|---|
| EGF peptide, TGFα | P01133 (SEQ ID NO: 78) P01135 (SEQ ID NO: 79) | EGFR | P00533 (SEQ ID NO: 21) | Receptor ubiquitously expressed, up-regulated in numerous tumors. |
| endothelin | P05305 (SEQ ID NO: 80) | EDNRA (ETA), EDNRB (ETB) | P25101 (SEQ ID NO: 22) P24530 (SEQ ID NO: 23) | Receptors present in blood vessels, nerves, and brain tissue. |
| F3 peptide | KDEPQRRSARLSAK PAPPKPEPKPKKAP AKK (SEQ ID NO: 81) | Nucleolin | P19338 (SEQ ID NO: 24) | Receptor on cell surface of endo-thelial cells. |
| Factor XI | P03951 (SEQ ID NO: 82) | F11 receptor | Q9Y624 (SEQ ID NO: 25) | Receptor is an epithelial tight junction adhesion molecule. |
| Fc fragment of IgA | | FCAR (CD98) | P24071 (SEQ ID NO: 26) | Receptor present on the surface of myeloid lineage cells such as neutro-phils, monocytes, macrophages, and eosinophils. |
| Fc fragment of IgE | | FCER1A, FCER1G | P12319 (SEQ ID NO: 27) P20491 (SEQ ID NO: 28) | Receptors bind alpha and gamma poly-peptide with respectively with high affinity. |
| Fc fragment of IgG | | FCGR1A (CD64) | P12314 (SEQ ID NO: 29) | Receptor is monocyte/macrophage specific. |
| galanin | P22466 (SEQ ID NO: 83) | GALR1, R2, R3 | P47211 (SEQ ID NO: 30) O43603 (SEQ ID NO: 31) O60755 (SEQ ID NO: 32) | Receptors expressd in CNS and some solid tumors. |
| gastric inhib-itory poly-peptide (GIP) | P09681 (SEQ ID NO: 84) | GIPR | P48546 (SEQ ID NO: 33) | Receptors found on beta cells in pancreas. |
| gastrin re-leasing peptide (GRP), bombesin | P07492 (SEQ ID NO: 85) P21591 (SEQ ID NO: 86) | GRPR | P30550 (SEQ ID NO: 34) | Highly expressed in pancreas, also in stomach, adrenal cortex, and brain. |
| glucagon (GCG) | P01275 (SEQ ID NO: 87) | GCGR | P47871 (SEQ ID NO: 35) | Receptor found on hepatocytes. |
| LyP-1 peptide | CGNKRTRGC (SEQ ID NO: 88) | C1QBP | Q07021 (SEQ ID NO: 36) | Receptor normally found in mitochondria, but is on cell surface of lymphatic, myeloid, and cancer cells in tumors. |
| neuromedin | P08949 (SEQ ID NO: 89) | NMBR | P28336 (SEQ ID NO: 37) | Found expressed and functional in lung carcinoma cells, related to GRPR. |
| parathyroid hormone | P01270 (SEQ ID NO: 90) | PTH1R, 2R | Q03431 (SEQ ID NO: 38) P49190 (SEQ ID NO: 39) | Receptor in osteoblasts and kidney. |
| poliovirus VP3, TIGIT | Q91UD0 (SEQ ID NO: 91) Q495A1 (SEQ ID NO: 92) | PVR (CD155) | P15151 (SEQ ID NO: 40) | Receptor establishes cell-cell junctions between epithelial cells. |
| prolactin | P01236 (SEQ ID NO: 93) | PRLR | P16471 (SEQ ID NO: 41) | Receptors found in mammillary glands, ovaries, pituitary glands, heart, lung, thymus, spleen, liver, pancreas, kidney, adrenal gland, uterus, skeletal muscle, skin, and areas of CNS. |

TABLE 3-continued

Examples of ligands included in the ligand-dimerizing agent binder conjugate and corresponding cell surface receptors bound by such ligands.

| Retargeting Element | Uniprot Accession Number\Sequence | Receptor | Uniprot Accession Number | Receptor Notes |
| --- | --- | --- | --- | --- |
| protective antigen (domain 4) | P13423 (SEQ ID NO: 94) | ANTXR1 (TEM8), R2 (CMG2) | P58335 (SEQ ID NO: 42) Q9H6X2 (SEQ ID NO: 43) | TEM8 found in umbilical vein endothelial cells and tumor endothelial cells. CMG2 in prostate, thymus, ovary, testis, pancreas, colon, heart, kidney, lung, liver, peripheral blood, leukocytes placenta, skeletal muscle, small intestine, and spleen. Involved in angiogenesis. |
| protein C (PROC) | P04070 (SEQ ID NO: 95) | EPCR | Q9UNN8 (SEQ ID NO: 44) | Receptor found on endothelial cells. |
| ricin B-chain | P02879 (SEQ ID NO: 96) | terminal galactose residues | | Beta-D-galactopyranoside moieties on cell surface glycoproteins and glycolipids found on most cells. |
| secretin | P09683 (SEQ ID NO: 97) | SCTR | P47872 (SEQ ID NO: 45) | Receptor ubiquitously expressed. |
| shigatoxin B subunit | Q8HA13 (SEQ ID NO: 98) | CD77 | Q9NPC4 (SEQ ID NO: 46) | Receptor found in renal epithelial tissues, CNS neurons and endothelium, pancreas cancer, colon cancer. |
| tachykinin peptides | P20366 (SEQ ID NO: 99) Q9UHF0 (SEQ ID NO: 100) | NK1R, K2R, K3R | P25103 (SEQ ID NO: 47) P21452 (SEQ ID NO: 48) P29371 (SEQ ID NO: 49) | Receptor binds family of neuropeptides known as tachykinins |
| tetanus toxin B-(heavy) chain | P04958 (SEQ ID NO: 101) | SV2A, 2B | Q7L0J3 (SEQ ID NO: 50) Q7L112 (SEQ ID NO: 51) | Receptors found on neuronal cells. |
| thrombin (F2) | P00734 (SEQ ID NO: 102) | F2R | P25116 (SEQ ID NO: 52) | Receptor has high affinity for activated thrombin, and is found mostly in smooth muscle and heart. |
| thrombospondin-1 (TSP1) | P07996 (SEQ ID NO: 103) | CD36, CD47, integrins | P16671 (SEQ ID NO: 53) Q08722 (SEQ ID NO: 54) | CD36 found on platelets and monocytes/macrophages. CD47 is broadly distributed, abundant in some epithelia and the brain, and has been found in ovarian tumors. TSP1 can bind to fibrinogen, fibronectin, laminin, type V collagen and integrins alpha-V/beta-1, alpha-V/beta-3 and alpha-IIb/beta-3. |
| Transferrin, TfR binding peptides | P02787 (SEQ ID NO: 104) | TFRC (CD71), TFR2 | P02786 (SEQ ID NO: 55) Q9UP52 (SEQ ID NO: 56) | Receptor is found in endothelial cells and colon, and is constitutively endocytosed. It is upregulated by cancer drug arabinoside cytosine. |
| vasoactive intestinal peptide | P01282 (SEQ ID NO: 105) | VIPR1, R2 | P32241 (SEQ ID NO: 57) P41587 (SEQ ID NO: 58) | VPAC1 found in CNS, liver, lung, intestine, and T-lymphocytes. VPAC2 found in CNS, pancreas, skeletal muscle, heart, kidney, adipose tissue, testis, and stomach. |
| VEGF | P15692 (SEQ ID NO: 106) | VEGFR1, R2, R3 | P17948 (SEQ ID NO: 59) P35968 (SEQ ID NO: 60) P35916 (SEQ ID NO: 61) | VEGFR1 found in normal lung, placenta, liver, kidney, heart, and brain. Specifically expressed in vascular endothelial cells and peripheral blood monocytes. VEGFR3 is expressed in corneal epithelial cells and vascular smooth muscle cells. |

TABLE 3-continued

Examples of ligands included in the ligand-dimerizing agent binder conjugate and corresponding cell surface receptors bound by such ligands.

| Retargeting Element | Uniprot Accession Number\Sequence | Receptor | Uniprot Accession Number | Receptor Notes |
|---|---|---|---|---|
| von Willebrand factor | P04275 (SEQ ID NO: 107) | (GPIbA, GPIbB, GP9, and GP5) in concert | P07359 (SEQ ID NO: 62) P13224 (SEQ ID NO: 63) P14770 (SEQ ID NO: 64) P40197 (SEQ ID NO: 65) | Receptor complex found on platelets. |
| scFvs | | Any* | | Can be designated by directed evolution of antibodies. |
| VHH | | Any* | | Can be designated by directed evolution of antibodies. |

VII. Embodiments

Embodiment 1. A recombinant nucleic acid encoding a capsid-dimerizing agent binder conjugate and a ligand-dimerizing agent binder conjugate.

Embodiment 2. The recombinant nucleic acid of embodiment 1, wherein said capsid-dimerizing agent binder conjugate comprises a capsid protein and a dimerizing agent binder.

Embodiment 3. The recombinant nucleic acid of embodiment 2, wherein said capsid protein is operably linked to said dimerizing agent binder.

Embodiment 4. The recombinant nucleic acid of embodiment 3, wherein said capsid protein is an adenoviral capsid protein.

Embodiment 5. The recombinant nucleic acid of embodiment 4, wherein said adenoviral capsid protein is a fiber protein.

Embodiment 6. The recombinant nucleic acid of embodiment 3, wherein said dimerizing agent binder is a FRB protein.

Embodiment 7. The recombinant nucleic acid of embodiment 1, wherein said ligand-dimerizing agent binder conjugate comprises a ligand and a dimerizing agent binder.

Embodiment 8. The recombinant nucleic acid of embodiment 7, wherein said ligand is operably linked to said dimerizing agent binder.

Embodiment 9. The recombinant nucleic acid of embodiment 7, wherein said ligand is capable of binding a cell.

Embodiment 10. The recombinant nucleic acid of embodiment 9, wherein said cell is a tumor cell.

Embodiment 11. The recombinant nucleic acid of embodiment 7, wherein said ligand is an antibody.

Embodiment 12. The recombinant nucleic acid of embodiment 11, wherein said antibody is a single domain antibody.

Embodiment 13. The recombinant nucleic acid of embodiment 7, wherein said dimerizing agent binder is an immunophilin protein.

Embodiment 14. The recombinant nucleic acid of embodiment 13, wherein said immunophilin protein is a FKBP protein.

Embodiment 15. The recombinant nucleic acid of embodiment 14, wherein said FKBP protein is a human FKBP protein.

Embodiment 16. The recombinant nucleic acid of embodiment 15, wherein said human FKBP protein is FKBP12.

Embodiment 17. A recombinant adenovirus comprising a recombinant nucleic acid of one of embodiments 1-16.

Embodiment 18. The recombinant adenovirus of embodiment 17, wherein said adenovirus is a replication incompetent adenovirus.

Embodiment 19. The recombinant adenovirus of embodiment 17, wherein said adenovirus is a replication competent adenovirus.

Embodiment 20. A recombinant adenovirus comprising a capsid-dimerizing agent binder conjugate.

Embodiment 21. The recombinant adenovirus of embodiment 20, wherein said capsid-dimerizing agent binder conjugate is bound to a dimerizing agent.

Embodiment 22. The recombinant adenovirus of embodiment 21, wherein said dimerizing agent is a compound.

Embodiment 23. The recombinant adenovirus of embodiment 22, wherein said compound is rapamycin.

Embodiment 24. The recombinant adenovirus of embodiment 21, wherein said dimerizing agent is an anti-cancer drug.

Embodiment 25. The recombinant adenovirus of embodiment 21, wherein said dimerizing agent is further bound to a ligand-dimerizing agent binder conjugate.

Embodiment 26. A cell comprising a recombinant adenovirus of any one of embodiments 20-25.

Embodiment 27. A method of forming an adenoviral cancer cell targeting construct, said method comprising: (i) infecting a cell with a recombinant adenovirus of embodiment 17, thereby forming an adenoviral infected cell; (ii) allowing said adenoviral infected cell to express said recombinant nucleic acid, thereby forming a ligand-dimerizing agent binder conjugate and a recombinant adenovirus comprising a capsid-dimerizing agent binder conjugate; (iii) contacting said recombinant adenovirus and said ligand-dimerizing agent binder conjugate with a dimerizing agent; (iv) allowing said recombinant adenovirus and said ligand-dimerizing agent binder conjugate to bind to said dimerizing agent, thereby forming said adenoviral cancer cell targeting construct.

Embodiment 28. A method of targeting a cell, said method comprising contacting a cell with a recombinant adenovirus of any one of embodiments 20-25.

Embodiment 29. The method of embodiment 28, wherein said cell is a cancer cell.

Embodiment 30. A method of targeting a cancer cell in a cancer patient, said method comprising: (i) administering to a cancer patient a recombinant adenovirus of embodiment 17; (ii) allowing said recombinant adenovirus to infect a cell in said cancer patient, thereby forming an adenoviral infected cell; (iii) allowing said adenoviral infected cell to express said recombinant nucleic acid, thereby forming a ligand-dimerizing agent binder conjugate and a recombinant adenovirus comprising a capsid-dimerizing agent binder conjugate; (iv) administering to said cancer patient a dimerizing agent; (v) allowing said recombinant adenovirus and said ligand-dimerizing agent binder conjugate to bind to said dimerizing agent, thereby forming an adenoviral cancer cell targeting construct; (vi) allowing said adenoviral cancer cell targeting construct to bind to a cancer cell, thereby targeting said cancer cell in said cancer patient.

Embodiment 31. The method of embodiment 30, wherein said cell is a cancer cell.

Embodiment 32. The method of embodiment 30, wherein said cell is a non-cancer cell.

Embodiment 33. A method of targeting a cell, said method comprising: (i) contacting a first cell with a recombinant adenovirus of embodiment 17; (ii) allowing said recombinant adenovirus to infect said first cell, thereby forming an adenoviral infected cell; (iii) allowing said adenoviral infected cell to express said recombinant nucleic acid, thereby forming a ligand-dimerizing agent binder conjugate and a recombinant adenovirus comprising a capsid-dimerizing agent binder conjugate; (iv) contacting said ligand-dimerizing agent binder conjugate and said recombinant adenovirus with a dimerizing agent; (v) allowing said recombinant adenovirus and said ligand-dimerizing agent binder conjugate to bind to said dimerizing agent, thereby forming an adenoviral cell targeting construct; (vi) allowing said adenoviral cell targeting construct to bind to a second cell, thereby targeting said cell.

Embodiment 34. The method of embodiment 33, wherein said first cell and said second cell form part of an organism.

Embodiment 35. The method of embodiment 33, wherein said first cell and said second cell form part of tissue culture vessel.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US09913866B2). An electronic copy of the "Sequence Listing" will also be available from the USPTO upon request and payment of the fee set forth in 37 CFR 1.19(b)(3).

The invention claimed is:

1. A recombinant adenovirus comprising a recombinant nucleic acid encoding a capsid-dimerizing agent binder conjugate and a ligand-dimerizing agent binder conjugate, wherein the capsid-dimerizing agent binder conjugate comprises an adenoviral fiber protein and a FRB protein inserted into the H1 loop of the adenoviral fiber protein, and the ligand-dimerizing agent binder conjugate comprises a ligand and a FKBP protein,
wherein the FRB protein is encoded by the nucleotide sequence of SEQ ID NO: 69 and the FKBP protein is at least 90% identical to the FKBP protein encoded by SEQ ID NO: 66,
and wherein said insertion of the FRB protein into the H1 loop of the adenoviral fiber protein does not inhibit replication and assembly of the adenovirus.

2. The recombinant adenovirus of claim 1, wherein the ligand is capable of binding a tumor cell.

3. The recombinant adenovirus of claim 1, wherein the ligand is an antibody.

4. The recombinant adenovirus claim 3, wherein the antibody is a single domain antibody.

5. The recombinant adenovirus of claim 1, wherein the FKBP protein is a human FKBP protein.

6. The recombinant adenovirus of claim 5, wherein the human FKBP protein is FKBP12.

7. A recombinant adenovirus comprising a capsid-dimerizing agent binder conjugate, wherein the capsid-dimerizing agent binder conjugate comprises an adenoviral fiber protein and a FRB protein inserted into the H1 loop of the adenoviral fiber protein, wherein the FRB protein is encoded by the nucleotide sequence of SEQ ID NO: 69, and wherein said insertion of the FRB protein into the H1 loop of the adenoviral fiber protein does not inhibit replication and assembly of the adenovirus.

8. The recombinant adenovirus of claim 7, wherein the capsid-dimerizing agent binder conjugate is bound to a dimerizing agent.

9. The recombinant adenovirus of claim 8, wherein the dimerizing agent is further bound to a ligand-dimerizing agent binder conjugate, wherein the ligand-dimerizing agent binder conjugate comprises a ligand and a FKBP protein at least 90% identical to the FKBP protein encoded by SEQ ID NO: 66.

10. The recombinant adenovirus of claim 8, wherein the dimerizing agent is rapamycin or a rapalog.

* * * * *